US009283051B2

(12) United States Patent
Garcia et al.

(10) Patent No.: US 9,283,051 B2
(45) Date of Patent: Mar. 15, 2016

(54) SYSTEM AND METHOD FOR ESTIMATING A TREATMENT VOLUME FOR ADMINISTERING ELECTRICAL-ENERGY BASED THERAPIES

(71) Applicant: Virginia Tech Intellectual Properties, Inc., Blacksburg, VA (US)

(72) Inventors: Paulo A. Garcia, Blacksburg, VA (US); Rafael V. Davalos, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 291 days.

(21) Appl. No.: 14/012,832

(22) Filed: Aug. 28, 2013

(65) Prior Publication Data
US 2013/0345697 A1 Dec. 26, 2013

Related U.S. Application Data

(63) Continuation-in-part of application No. 12/491,151, filed on Jun. 24, 2009, now Pat. No. 8,992,517, which is a continuation-in-part of application No. 12/432,295, filed on Apr. 29, 2009.
(Continued)

(51) Int. Cl.
*A61B 18/12* (2006.01)
*A61B 19/00* (2006.01)
(Continued)

(52) U.S. Cl.
CPC ............ *A61B 19/50* (2013.01); *A61B 18/1477* (2013.01); *A61B 18/18* (2013.01);
(Continued)

(58) Field of Classification Search
CPC .. A61B 18/1492; A61B 18/14; A61B 18/082; A61B 2018/00577; A61B 2018/0016; A61B 2018/1425; A61B 19/50
See application file for complete search history.

(56) References Cited

U.S. PATENT DOCUMENTS 1,653,819 A 12/1927 Northcott et al.
4,016,886 A 4/1977 Doss et al.
(Continued)

FOREIGN PATENT DOCUMENTS

DE 863111tr 1/1953
DE 4000893tr 7/1991
(Continued)

OTHER PUBLICATIONS

Co-pending Application No. PCT/US2010/029243, filed Mar. 30, 2010, published as WO 2010/117806 on Oct. 14, 2010.
(Continued)

*Primary Examiner* — Michael Peffley
(74) *Attorney, Agent, or Firm* — New River Valley IP Law, P.C.; Michele L. Mayberry

(57) ABSTRACT

The invention provides for a system for estimating a 3-dimensional treatment volume for a device that applies treatment energy through a plurality of electrodes defining a treatment area, the system comprising a memory, a display device, a processor coupled to the memory and the display device, and a treatment planning module stored in the memory and executable by the processor. In one embodiment, the treatment planning module is adapted to generate an estimated first 3-dimensional treatment volume for display in the display device based on the ratio of a maximum conductivity of the treatment area to a baseline conductivity of the treatment area. The invention also provides for a method for estimating 3-dimensional treatment volume, the steps of which are executable through the processor. In embodiments, the system and method are based on a numerical model which may be implemented in computer readable code which is executable through a processor.

16 Claims, 23 Drawing Sheets

Related U.S. Application Data

(60) Provisional application No. 61/694,144, filed on Aug. 28, 2012, provisional application No. 61/171,564, filed on Apr. 22, 2009, provisional application No. 61/167,997, filed on Apr. 9, 2009, provisional application No. 61/075,216, filed on Jun. 24, 2008, provisional application No. 61/125,840, filed on Apr. 29, 2008.

(51) Int. Cl.
*A61B 18/18* (2006.01)
*C12N 13/00* (2006.01)
*A61B 18/14* (2006.01)
*A61B 18/00* (2006.01)

(52) U.S. Cl.
CPC ........ *C12N 13/00* (2013.01); *A61B 2018/0016* (2013.01); *A61B 2018/00613* (2013.01); *A61B 2018/1425* (2013.01); *A61B 2019/504* (2013.01)

(56) References Cited

U.S. PATENT DOCUMENTS

| | | | |
|---|---|---|---|
| 4,226,246 A | 10/1980 | Fragnet | |
| 4,262,672 A | 4/1981 | Kief | |
| 4,407,943 A | 10/1983 | Cole et al. | |
| 4,416,276 A | 11/1983 | Newton et al. | |
| 4,810,963 A | 3/1989 | Blake-Coleman et al. | |
| 4,822,470 A | 4/1989 | Chang | |
| 4,907,601 A | 3/1990 | Frick | |
| 4,946,793 A | 8/1990 | Marshall, III | |
| 5,019,034 A | 5/1991 | Weaver et al. | |
| 5,052,391 A | 10/1991 | Silberstone et al. | |
| 5,058,605 A | 10/1991 | Slovak | |
| 5,098,843 A | 3/1992 | Calvin | |
| 5,134,070 A | 7/1992 | Casnig | |
| 5,173,158 A | 12/1992 | Schmukler | |
| 5,192,312 A | 3/1993 | Orton | |
| 5,193,537 A | 3/1993 | Freeman | |
| 5,273,525 A | 12/1993 | Hofmann | |
| 5,283,194 A | 2/1994 | Schmukler | |
| 5,318,563 A | 6/1994 | Malis et al. | |
| 5,328,451 A | 7/1994 | Davis et al. | |
| 5,389,069 A | 2/1995 | Weaver | |
| 5,403,311 A | 4/1995 | Abele et al. | |
| 5,425,752 A | 6/1995 | Vu Nguyen | |
| 5,439,440 A | 8/1995 | Hofmann | |
| 5,458,625 A | 10/1995 | Kendall | |
| 5,533,999 A | 7/1996 | Hood et al. | |
| 5,536,240 A | 7/1996 | Edwards et al. | |
| 5,575,811 A | 11/1996 | Reid et al. | |
| 5,626,146 A | 5/1997 | Barber et al. | |
| 5,634,899 A | 6/1997 | Shapland et al. | |
| 5,674,267 A | 10/1997 | Mir et al. | |
| 5,702,359 A | 12/1997 | Hofmann et al. | |
| 5,718,246 A | 2/1998 | Vona | |
| 5,720,921 A | 2/1998 | Meserol | |
| 5,778,894 A | 7/1998 | Dorogi et al. | |
| 5,782,882 A | 7/1998 | Lerman et al. | |
| 5,800,378 A | 9/1998 | Edwards et al. | |
| 5,810,762 A | 9/1998 | Hofmann | |
| 5,836,905 A | 11/1998 | Lemelson et al. | |
| 5,843,026 A | 12/1998 | Edwards et al. | |
| 5,843,182 A | 12/1998 | Goldstein | |
| 5,873,849 A | 2/1999 | Bernard | |
| 5,919,142 A | 7/1999 | Boone et al. | |
| 5,947,889 A | 9/1999 | Hehrlein | |
| 5,983,131 A | 11/1999 | Weaver et al. | |
| 5,991,697 A | 11/1999 | Nelson et al. | |
| 5,999,847 A | 12/1999 | Elstrom | |
| 6,009,347 A | 12/1999 | Hofmann | |
| 6,010,613 A | 1/2000 | Walters et al. | |
| 6,016,452 A | 1/2000 | Kasevich | |
| 6,029,090 A | 2/2000 | Herbst | |
| 6,041,252 A | 3/2000 | Walker et al. | |
| 6,055,453 A | 4/2000 | Hofmann et al. | |
| 6,068,650 A | 5/2000 | Hofmann et al. | |
| 6,074,389 A | 6/2000 | Levine et al. | |
| 6,085,115 A | 7/2000 | Weaver et al. | |
| 6,090,106 A | 7/2000 | Goble et al. | |
| 6,102,885 A | 8/2000 | Bass | |
| 6,106,521 A | 8/2000 | Blewett et al. | |
| 6,109,270 A | 8/2000 | Mah et al. | |
| 6,116,330 A | 9/2000 | Salyer | |
| 6,122,599 A | 9/2000 | Mehta | |
| 6,132,419 A | 10/2000 | Hofmann | |
| 6,159,163 A | 12/2000 | Strauss et al. | |
| 6,208,893 B1 | 3/2001 | Hofmann | |
| 6,210,402 B1 | 4/2001 | Olsen et al. | |
| 6,212,433 B1 | 4/2001 | Behl | |
| 6,216,034 B1 | 4/2001 | Hofmann et al. | |
| 6,219,577 B1 | 4/2001 | Brown, III et al. | |
| 6,241,702 B1 | 6/2001 | Lundquist et al. | |
| 6,241,725 B1 | 6/2001 | Cosman | |
| 6,261,831 B1 | 7/2001 | Agee | |
| 6,278,895 B1 | 8/2001 | Bernard | |
| 6,287,293 B1 | 9/2001 | Jones et al. | |
| 6,300,108 B1 | 10/2001 | Rubinsky et al. | |
| 6,326,177 B1 | 12/2001 | Schoenbach et al. | |
| 6,347,247 B1 | 2/2002 | Dev et al. | |
| 6,349,233 B1 | 2/2002 | Adams | |
| 6,351,674 B2 | 2/2002 | Silverstone | |
| 6,387,671 B1 | 5/2002 | Rubinsky et al. | |
| 6,403,348 B1 | 6/2002 | Rubinsky et al. | |
| 6,470,211 B1 | 10/2002 | Ideker et al. | |
| 6,482,619 B1 | 11/2002 | Rubinsky et al. | |
| 6,488,680 B1 | 12/2002 | Francischelli et al. | |
| 6,493,592 B1 | 12/2002 | Leonard et al. | |
| 6,500,173 B2 | 12/2002 | Underwood et al. | |
| 6,503,248 B1 | 1/2003 | Levine | |
| 6,526,320 B2 | 2/2003 | Mitchell | |
| 6,562,604 B2 | 5/2003 | Rubinsky et al. | |
| 6,607,529 B1 | 8/2003 | Jones et al. | |
| 6,611,706 B2 | 8/2003 | Avrahami et al. | |
| 6,613,211 B1 | 9/2003 | Mccormick et al. | |
| 6,627,421 B1 | 9/2003 | Unger et al. | |
| 6,653,091 B1 | 11/2003 | Dunn et al. | |
| 6,669,691 B1 | 12/2003 | Taimisto | |
| 6,678,558 B1 | 1/2004 | Dimmer et al. | |
| 6,692,493 B2 | 2/2004 | Mcgovern et al. | |
| 6,697,669 B2 | 2/2004 | Dev et al. | |
| 6,697,670 B2 | 2/2004 | Chomenky et al. | |
| 6,702,808 B1 | 3/2004 | Kreindel | |
| 6,795,728 B2 | 9/2004 | Chornenky et al. | |
| 6,801,804 B2 | 10/2004 | Miller et al. | |
| 6,865,416 B2 | 3/2005 | Dev et al. | |
| 6,892,099 B2 | 5/2005 | Jaafar et al. | |
| 6,912,417 B1 | 6/2005 | Bernard et al. | |
| 6,927,049 B2 | 8/2005 | Rubinsky et al. | |
| 6,962,587 B2 | 11/2005 | Johnson et al. | |
| 6,972,014 B2 | 12/2005 | Eum et al. | |
| 6,994,706 B2 | 2/2006 | Chornenky et al. | |
| 7,012,061 B1 | 3/2006 | Reiss et al. | |
| 7,053,063 B2 | 5/2006 | Rubinsky et al. | |
| 7,054,685 B2 | 5/2006 | Dimmer et al. | |
| 7,063,698 B2 | 6/2006 | Whayne et al. | |
| 7,113,821 B1 | 9/2006 | Sun et al. | |
| 7,130,697 B2 | 10/2006 | Chornenky et al. | |
| 7,211,083 B2 | 5/2007 | Chornenky et al. | |
| 7,232,437 B2 * | 6/2007 | Berman ................ A61B 18/22 600/374 |
| 7,267,676 B2 | 9/2007 | Chornenky et al. | |
| 7,291,146 B2 | 11/2007 | Steinke et al. | |
| 7,344,533 B2 | 3/2008 | Pearson et al. | |
| 7,399,747 B1 | 7/2008 | Clair et al. | |
| 7,655,004 B2 | 2/2010 | Long | |
| 7,674,249 B2 | 3/2010 | Ivorra et al. | |
| 7,680,543 B2 | 3/2010 | Azure | |
| 7,718,409 B2 | 5/2010 | Rubinsky et al. | |
| 7,742,795 B2 | 6/2010 | Stone et al. | |
| 7,937,143 B2 | 5/2011 | Demarais et al. | |
| 7,951,582 B2 | 5/2011 | Gazit et al. | |
| 7,955,827 B2 | 6/2011 | Rubinsky et al. | |

(56) References Cited

U.S. PATENT DOCUMENTS

| | | | |
|---|---|---|---|
| 8,048,067 B2* | 11/2011 | Davalos | A61B 18/12 606/32 |
| 8,114,070 B2 | 2/2012 | Rubinsky et al. | |
| 8,162,918 B2 | 4/2012 | Ivorra et al. | |
| 8,221,411 B2* | 7/2012 | Francischelli | A61B 18/1442 606/41 |
| 8,267,927 B2* | 9/2012 | Dalal | A61B 18/1477 606/34 |
| 8,267,936 B2 | 9/2012 | Hushka et al. | |
| 8,282,631 B2 | 10/2012 | Davalos et al. | |
| 8,298,222 B2 | 10/2012 | Rubinsky et al. | |
| 8,348,921 B2 | 1/2013 | Ivorra et al. | |
| 8,425,505 B2 | 4/2013 | Long | |
| 8,454,594 B2 | 6/2013 | Demarais et al. | |
| 8,465,484 B2 | 6/2013 | Davalos et al. | |
| 8,518,031 B2 | 8/2013 | Boyden et al. | |
| 8,603,087 B2 | 12/2013 | Rubinsky et al. | |
| 8,814,860 B2 | 8/2014 | Davalos et al. | |
| 8,835,166 B2 | 9/2014 | Phillips et al. | |
| 8,926,606 B2 | 1/2015 | Davalos et al. | |
| 8,992,517 B2 | 3/2015 | Davalos et al. | |
| 2001/0044596 A1 | 11/2001 | Jaafar | |
| 2001/0046706 A1 | 11/2001 | Rubinsky et al. | |
| 2001/0051366 A1 | 12/2001 | Rubinsky et al. | |
| 2002/0010491 A1 | 1/2002 | Schoenbach et al. | |
| 2002/0055731 A1 | 5/2002 | Atala et al. | |
| 2002/0077676 A1 | 6/2002 | Schroeppel et al. | |
| 2002/0082543 A1 | 6/2002 | Park et al. | |
| 2002/0099323 A1 | 7/2002 | Dev et al. | |
| 2002/0115208 A1 | 8/2002 | Mitchell et al. | |
| 2002/0119437 A1 | 8/2002 | Grooms et al. | |
| 2002/0137121 A1 | 9/2002 | Rubinsky et al. | |
| 2002/0138117 A1 | 9/2002 | Son | |
| 2002/0183684 A1 | 12/2002 | Dev et al. | |
| 2002/0193831 A1 | 12/2002 | Smith | |
| 2003/0009110 A1 | 1/2003 | Tu et al. | |
| 2003/0060856 A1 | 3/2003 | Chornenky et al. | |
| 2003/0088189 A1 | 5/2003 | Tu et al. | |
| 2003/0096407 A1 | 5/2003 | Atala et al. | |
| 2003/0130711 A1 | 7/2003 | Pearson et al. | |
| 2003/0166181 A1 | 9/2003 | Rubinsky et al. | |
| 2003/0170898 A1 | 9/2003 | Gundersen et al. | |
| 2003/0194808 A1 | 10/2003 | Rubinsky et al. | |
| 2003/0199050 A1 | 10/2003 | Mangano et al. | |
| 2003/0208200 A1 | 11/2003 | Palanker et al. | |
| 2003/0225360 A1 | 12/2003 | Eppstein et al. | |
| 2004/0009459 A1 | 1/2004 | Anderson et al. | |
| 2004/0019371 A1 | 1/2004 | Jaafar et al. | |
| 2004/0059389 A1 | 3/2004 | Chornenky et al. | |
| 2004/0146877 A1 | 7/2004 | Diss et al. | |
| 2004/0153057 A1 | 8/2004 | Davison | |
| 2004/0176855 A1 | 9/2004 | Badylak | |
| 2004/0193097 A1 | 9/2004 | Hofmann et al. | |
| 2004/0236376 A1 | 11/2004 | Miklavcic et al. | |
| 2004/0243107 A1 | 12/2004 | Macoviak et al. | |
| 2004/0267189 A1 | 12/2004 | Mavor et al. | |
| 2005/0013870 A1 | 1/2005 | Freyman et al. | |
| 2005/0043726 A1 | 2/2005 | Mchale et al. | |
| 2005/0049541 A1 | 3/2005 | Behar et al. | |
| 2005/0165393 A1 | 7/2005 | Eppstein | |
| 2005/0171523 A1 | 8/2005 | Rubinsky et al. | |
| 2005/0171574 A1 | 8/2005 | Rubinsky et al. | |
| 2005/0182462 A1 | 8/2005 | Chornenky et al. | |
| 2005/0261672 A1 | 11/2005 | Deem et al. | |
| 2005/0282284 A1 | 12/2005 | Rubinsky et al. | |
| 2005/0288730 A1 | 12/2005 | Deem et al. | |
| 2006/0004356 A1 | 1/2006 | Bilski et al. | |
| 2006/0015147 A1 | 1/2006 | Persson et al. | |
| 2006/0024359 A1 | 2/2006 | Walker et al. | |
| 2006/0025760 A1 | 2/2006 | Podhajsky | |
| 2006/0079883 A1 | 4/2006 | Elmouelhi et al. | |
| 2006/0121610 A1 | 6/2006 | Rubinsky et al. | |
| 2006/0142801 A1 | 6/2006 | Demarais et al. | |
| 2006/0182684 A1 | 8/2006 | Beliveau | |
| 2006/0212078 A1 | 9/2006 | Demarais et al. | |

| | | |
|---|---|---|
| 2006/0217703 A1 | 9/2006 | Chornenky et al. |
| 2006/0235474 A1 | 10/2006 | Demarais |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0118069 A1 | 5/2007 | Persson et al. |
| 2007/0129711 A1 | 6/2007 | Altshuler et al. |
| 2007/0156135 A1 | 7/2007 | Rubinsky et al. |
| 2007/0230757 A1 | 10/2007 | Trachtenberg et al. |
| 2007/0287950 A1 | 12/2007 | Kjeken et al. |
| 2008/0015571 A1 | 1/2008 | Rubinsky et al. |
| 2008/0021371 A1 | 1/2008 | Rubinsky et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0071262 A1 | 3/2008 | Azure |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0132884 A1 | 6/2008 | Rubinsky et al. |
| 2008/0132885 A1 | 6/2008 | Rubinsky et al. |
| 2008/0200912 A1 | 8/2008 | Long |
| 2008/0208052 A1 | 8/2008 | LePivert et al. |
| 2008/0214986 A1 | 9/2008 | Ivorra et al. |
| 2008/0269586 A1 | 10/2008 | Rubinsky et al. |
| 2009/0024075 A1 | 1/2009 | Schroeppel et al. |
| 2009/0029407 A1 | 1/2009 | Gazit et al. |
| 2009/0062788 A1 | 3/2009 | Long et al. |
| 2009/0105703 A1 | 4/2009 | Shadduck |
| 2009/0198231 A1 | 8/2009 | Esser et al. |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0281477 A1 | 11/2009 | Mikus et al. |
| 2009/0292342 A1 | 11/2009 | Rubinsky et al. |
| 2009/0318905 A1 | 12/2009 | Bhargav et al. |
| 2009/0326436 A1 | 12/2009 | Rubinsky et al. |
| 2010/0004623 A1 | 1/2010 | Hamilton et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0087813 A1 | 4/2010 | Long |
| 2010/0130975 A1 | 5/2010 | Long |
| 2010/0152725 A1 | 6/2010 | Pearson et al. |
| 2010/0160850 A1 | 6/2010 | Ivorra et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256630 A1 | 10/2010 | Hamilton, Jr. et al. |
| 2010/0261994 A1 | 10/2010 | Davalos et al. |
| 2010/0331758 A1 | 12/2010 | Davalos et al. |
| 2011/0034209 A1 | 2/2011 | Rubinsky et al. |
| 2011/0064671 A1 | 3/2011 | Bynoe |
| 2011/0106221 A1 | 5/2011 | Neal, II et al. |
| 2011/0118732 A1 | 5/2011 | Rubinsky et al. |
| 2011/0217730 A1 | 9/2011 | Gazit et al. |
| 2012/0034131 A1 | 2/2012 | Rubinsky et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0109122 A1 | 5/2012 | Arena et al. |
| 2012/0179091 A1 | 7/2012 | Ivorra et al. |
| 2012/0226218 A1 | 9/2012 | Phillips et al. |
| 2012/0265186 A1 | 10/2012 | Burger et al. |

(56) References Cited

U.S. PATENT DOCUMENTS

| | | |
|---|---|---|
| 2012/0277741 A1 | 11/2012 | Davalos et al. |
| 2013/0090646 A1 | 4/2013 | Moss et al. |
| 2013/0108667 A1 | 5/2013 | Soikum et al. |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0039489 A1 | 2/2014 | Davalos et al. |
| 2014/0088578 A1 | 3/2014 | Rubinsky et al. |
| 2014/0163551 A1 | 6/2014 | Maor et al. |
| 2015/0088120 A1 | 3/2015 | Garcia et al. |
| 2015/0164584 A1 | 6/2015 | Davalos et al. |
| 2015/0173824 A1 | 6/2015 | Davalos et al. |
| 2015/0289923 A1 | 10/2015 | Davalos et al. |
| 2015/0327944 A1 | 11/2015 | Davalos et al. |

FOREIGN PATENT DOCUMENTS

| | | | |
|---|---|---|---|
| EP | 0378132 | A | 7/1990 |
| EP | 0528891 | B1 | 7/2000 |
| EP | 0935482 | B1 | 5/2005 |
| WO | 9104014 | | 4/1991 |
| WO | 9639531 | A | 12/1996 |
| WO | 9814238 | A | 4/1998 |
| WO | 0020554 | A | 4/2000 |
| WO | 0107583 | A | 2/2001 |
| WO | 0107584 | A | 2/2001 |
| WO | 0107585 | A | 2/2001 |
| WO | 0110319 | A | 2/2001 |
| WO | 0148153 | A | 7/2001 |
| WO | 0148153 | A1 | 7/2001 |
| WO | 0181533 | A | 11/2001 |
| WO | 02078527 | A | 10/2002 |
| WO | 02089686 | A | 11/2002 |
| WO | 02100459 | A | 12/2002 |
| WO | 03099382 | A | 12/2003 |
| WO | 2004037341 | A2 | 5/2004 |
| WO | 2005065284 | A | 7/2005 |
| WO | 2007137303 | | 7/2009 |
| WO | 2009134876 | A | 11/2009 |
| WO | 2010117806 | A1 | 10/2010 |
| WO | 2010118387 | A | 10/2010 |
| WO | 2010151277 | A | 12/2010 |
| WO | 2011047387 | A | 4/2011 |
| WO | 2012071526 | A | 5/2012 |
| WO | 2012088149 | A | 6/2012 |
| WO | 2015175570 | A1 | 11/2015 |

OTHER PUBLICATIONS

Co-Pending U.S. Appl. No. 12/491,151, filed Jun. 24, 2009.
Co-Pending U.S. Appl. No. 13/332,133, filed Dec. 20, 2011.
Co-Pending U.S. Appl. No. 13/550,307, filed Jul. 16, 2012.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 23, 2013.
Co-Pending U.S. Appl. No. 14/012,832, filed Aug. 28, 2013.
Co-Pending U.S. Appl. No. 14/017,210, filed Sep. 3, 2013.
Co-pending European Application No. 10 824 248.8, Invitation Pursuant to rule 62a(1) EPC (Sep. 25, 2013).
Corovic, S., et al., "Analytical and numerical quantification and comparison of the local electric field in the tissue for different electrode configurations," Biomed Eng Online, 6, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Crowley, Electrical Breakdown of Biomolecular Lipid Membranes as an Electromechanical Instability, Biophysical Journal, vol. 13, pp. 711-724, 1973.

Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, et al., Theoretical Analysis of the Thermal Effects During in Vivo Tissue Electroporation, Bioelectrochemistry, vol. 61, pp. 99-107, 2003.
Davalos, et al., A Feasibility Study for Electrical Impedance Tomography as a Means to Monitor T issue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04. 046 (2008).
Davalos, R.V., et al., "Electrical impedance tomography for imaging tissue electroporation," IEEE Transactions on Biomedical Engineering, 51, 761-767, 2004.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd, J. et al., In-Vivo Results of a New Focal Tissue Ablation Technique: Irreversible Electroporaton, IEEE Trans. Biomed. Eng. 53 (2006) p. 1409-1415.
Edd, J.F, et al., 2007, "Mathematical modeling of irreversible electroporation fortreatment planning.", Technology in Cancer Research and Treatment., 6:275-286.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Extended European Search Report. May 11, 2012. PCT/US2009042100 from EP 09739678.2.
Faroja, M., et al., "Irreversible Electroporation Ablation: Is the entire Damage Nonthermal?", Radiology, 266(2), 462-470 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.
Garcia et al., "Irreversible electroporation (IRE) to treat brain cancer." ASME Summer Bioengineering Conference, Marco Island, FL, Jun. 25-29, 2008.

(56) References Cited

OTHER PUBLICATIONS

Garcia P.A., et al., "7.0-T Magnetic Resonance Imaging Characterization of Acute Blood-Brain-Barrier Disruption Achieved with Intracranial Irreversible Electroporation", PLOS One, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Garcia, P. et al. Intracranial nonthermal irreversible electroporation: in vivo analysis. J Membr Biol 236, 127-136 (2010).
Gauger, et al., A Study of Dielectric Membrane Breakdown in the Fucus Egg, J. Membrane Biol., vol. 48, No. 3, pp. 249-264, 1979.
Gehl, et al., In Vivo Electroporation of Skeletal Muscle: Threshold, Efficacy and Relation to Electric Field Distribution, Biochimica et Biphysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Glidewell, et al., The Use of Magnetic Resonance Imaging Data and the Inclusion of Anisotropic Regions in Electrical Impedance Tomography, Biomed, Sci. Instrum. 1993; 29: 251-7.
Gothelf, et al., Electrochemotherapy: Results of Cancer Treatment Using Enhanced Delivery of Bleomycin by Electroporation, Cancer Treatment Reviews 2003: 29: 371-387.
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions on Biomedical Engineering, vol. 42, No. 9, Sep. 1995.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Heller, et al., Clinical Applications of Electrochemotherapy, Advanced Drug Delivery Reviews, vol. 35, pp. 119-129, 1999.
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS One, Aug. 2012, 7:8, e42817.
Ho, et al., Electroporation of Cell Membranes: A Review, Critical Reviews in Biotechnology, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Ivanuša, et al., MRI Macromolecular Contrast Agents as Indicators of Changed Tumor Blood Flow, Radiol. Oncol. 2001; 35(2): 139-47.
Jaroszeski, et al., In Vivo Gene Delivery by Electroporation, Advanced Drug Delivery Review, vol. 35, pp. 131-137, 1999.
Jossinet et al., Electrical Impedance Endo-Tomography: Imaging Tissue From Inside, IEEE Transactions on Medical Imaging, vol. 21, No. 6, Jun. 2002, pp. 560-565.
Kinosita, et al., Hemolysis of Human Erythrocytes by a Transient Electric Field, Proc. Natl. Acad. Sci. USA, vol. 74, No. 5, pp. 1923-1927, 1977.
Lee, E. W. et al. Advanced Hepatic Ablation Technique for Creating Complete Cell Death : Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.
Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
Mahmood, F., et al., "Diffusion-Weighted MRI for Verification of Electroporation-Based Treatments", Journal of Membrane Biology 240: 131-138 (2011).
Mahnic-Kalamiza, S., et al., "Educational application for visualization and analysis of electric field strength in multiple electrode electroporation," BMC Med Educ, vol. 12, p. 102, 2012.
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS One, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.

(56) References Cited

OTHER PUBLICATIONS

Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Therapeutic Perspectives of In Vivo Cell Electropermeabilization, Bioelectrochemistry, vol. 53, pp. 1-10, 2000.
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-1085. Epub 2012 Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Okino, et al., Effects of High-Voltage Electrical Impulse and an Anticancer Drug on in Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Pavselj, N. et al. The course of tissue permeabilization studied on a mathematical model of a subcutaneous tumor in small animals. IEEE Trans Biomed Eng 52, 1373-1381 (2005).
PCT International Preliminary Report on Patentability of Corresponding International Application No. PCT/2011/062067, dated May 28, 2013.
PCT International Preliminary Report on Patentability of Corresponding International Application No. PCT/2011/066239, dated Jun. 25, 2013.
PCT International Search Report (Aug. 2, 2011), Written Opinion (Aug. 2, 2011), and International Preliminary Report on Patentability (Apr. 17, 2012) of PCT/US10/53077.
PCT International Search Report (Aug. 22, 2012), and Written Opinion (Aug. 22, 2012) of PCT/US11/66239.
PCT International Search Report (Aug. 26, 2005), Written Opinion (Aug. 26, 2005), and International Preliminary Report on Patentability (Jun. 26, 2006) of PCT/US2004/043477.
PCT International Search Report (Jan. 19, 2010), Written Opinion (Jan. 19, 2010), and International Preliminary Report on Patentability (Jan. 4, 2010) of PCT/US09/62806, 15 pgs.
PCT International Search Report (Jul. 15, 2010), Written Opinion (Jul. 15, 2010), and International Preliminary Report on Patentability (Oct. 11, 2011) from PCT/US2010/030629.
PCT International Search Report (Jul. 9, 2009), Written Opinion (Jul. 9, 2009), and International Preliminary Report on Patentability (Nov. 2, 2010) of PCT/US2009/042100.
PCT International Search Report and Written Opinion (Jul. 25, 2012) of PCT/US2011/062067.
PCT International Search Report, 4 pgs, (Jul. 30, 2010), Written Opinion, 7 pgs, (Jul. 30, 2010), and International Preliminary Report on Patentability, 8 pgs, (Oct. 4, 2011) from PCT/US2010/029243.
Phillips, M., Maor, E. & Rubinsky, B. Non-Thermal Irreversible Electroporation for Tissue Decellularization. J. Biomech. Eng, doi:10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Precision Office TUNA System, When Patient Satisfaction is Your Goal, VidaMed 2001.
Rajagopal, V. and S.G. Rockson, Coronary restenosis: a review of mechanisms and management, The American Journal of Medicine, 2003, 115(7): p. 547-553.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Salford, L.G., et al., "A new brain tumour therapy combining bleomycin with in vivo electropermeabilization", Biochem. Biophys. Res. Commun., 194(2): 938-943 (1993).
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.

(56) References Cited

OTHER PUBLICATIONS

Sharma, A., et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al, Percutaneous ethanol injection therapy for hepatocellular carcinoma: results in 146 patients. AJR, 1993, 160: p. 1023-8.
Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson, K. R., et al., "Investigation of the Safety of Irreversible Electroporation in Humans" J. Vascular Int. Radiol. 22 (5), 611-621 (2011).
Vidamed, Inc., Transurethral Needle Ablation (TUNA): Highlights from Worldwide Clinical Studies, Vidamed's Office TUNA System, 2001.
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weisstein: Cassini Ovals. From MathWorld—A. Wolfram Web Resource; Apr. 30, 2010; http://mathworld.wolfram.com/ (updated May 18, 2011).
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Barber, Electrical Impedance Tomography Applied Potential Tomography, Advances in Biomedical Engineering, Beneken and Thevenin, eds., IOS Press, pp. 165-173, 1993.
Co-Pending U.S. Appl. No. 12/432,295, Response to Non-Final Office Action, dated Apr. 28, 2014, 14 pages.
Co-Pending U.S. Appl. No. 12/491,151, Non-Final Rejection dated Apr. 4, 2014, 12 pages.
A.I. Daud et al., "Phase I Trial of Interleukin-12 Plasmid Electroporation in Patients With Metastatic Melanoma," Journal of Clinical Oncology, 26, pp. 5896-5903, 2008.
Co-Pending U.S. Appl. No. 12/432,295, Response to Jun. 16, 2014 Final Rejection filed Oct. 16, 2014, 13 pages.
Co-Pending Application No. PCT/US15/30429, filed May 12, 2015.
Co-Pending U.S. Appl. No. 12/432,295, Non-Final Office Action dated Jun. 23, 2015, 12 pages.
Co-Pending U.S. Appl. No. 12/432,295, Supplemental Response After RCE, filed Nov. 17, 2014, 9 pages.
Co-Pending U.S. Appl. No. 14/686,380, filed Apr. 14, 2015.
Golberg, A. and Rubinsky, B., "A statistical model for multidimensional irreversible electroporation cell death in tissue." Biomed Eng Online, 9, 13 pages, 2010.
Neal II et al., "A Case Report on the Successful Treatment of a Large Soft-Tissue Sarcoma with Irreversible Electroporation," Journal of Clinical Oncology, 29, pp. 1-6, 2011.
Co-Pending U.S. Appl. No. 12/432,295, Final Rejection dated Jun. 16, 2014, 14 pages.

Co-Pending U.S. Appl. No. 12/491,151, Response to Apr. 4, 2014 Non-Final Rejection dated Aug. 22, 2014, 12 pages.
Co-Pending U.S. Appl. No. 12/491,151, Official Notice of Allowance dated Nov. 6, 2014, 15 pages.
Co-Pending U.S. Appl. No. 14/558,631, filed Dec. 2, 2014.
Co-Pending U.S. Appl. No. 14/627,046, filed Feb. 20, 2015.
Agerholm-Larsen, B., et al., "Preclinical Validation of Electrochemotherapy as an Effective Treatment for Brain Tumors", Cancer Research 71: 3753-3762 (2011).
Al-Sakere, B. et al., 2007, "Tumor ablation with irreversible electroporation." PLoS One 2.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Bancroft, et al., Design of a Flow Perfusion Bioreactor System for Bone Tissue-Engineering Applications, Tissue Engineering, vol. 9, No. 3, 2003, p. 549-554.
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Ben-David, E.,et al., "Characterization of Irreversible Electroporation Ablation in In Vivo Procine Liver" Am. J. Roentgenol. 198(1), W62-W68 (2012).
Blad, et al., Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Boone, K., Barber, D. & Brown, B. Review—Imaging with electricity: report of the European Concerted Action on Impedance Tomography. J. Med. Eng. Technol. 21, 201-232 (1997).
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W.,et al., "The Electrical Discharge of the Electric Eel, Electrophorous Electricus," Zoologica, 1937, 22(1), pp. 1-32.

(56) References Cited

OTHER PUBLICATIONS

Cook, et al., ACT3: A High-Speed, High-Precision Electrical Impedance Tomograph, IEEE Transactions on Biomedical Engineering, vol. 41, No. 8, Aug. 1994.
Co-Pending U.S. Appl. No. 10/571,162, filed Oct. 18, 2006 (published as 2007/0043345 on Feb. 22, 2007).
Co-Pending U.S. Appl. No. 12/432,295, filed Apr. 29, 2009.
Co-Pending U.S. Appl. No. 12/432,295, Final Rejection dated Mar. 21, 2012, 14 pages.
Co-Pending U.S. Appl. No. 12/432,295, Non-Final Office Action dated Nov. 26, 2013, 15 pages.
Co-Pending U.S. Appl. No. 12/432,295, Non-Final Rejection dated Nov. 10, 2011, 10 pages.
Co-Pending U.S. Appl. No. 12/432,295, Requirement for Restriction/Election dated Aug. 9, 2011, 7 pages.
Co-Pending U.S. Appl. No. 12/432,295, Response to Non-Final Rejection dated Jan. 23, 2012, 9 pages.
Co-Pending U.S. Appl. No. 12/432,295, Response to Requirement for Restriction/Election dated Sep. 2, 2011, 2 pages.
Co-Pending U.S. Appl. No. 12/432,295, Response with RCE to Final Rejection dated Jul. 23, 2012, 13 pages.
Co-Pending U.S. Appl. No. 12/491,151, Final Rejection dated Apr. 20, 2012, 8 pages.
Co-Pending U.S. Appl. No. 12/491,151, Non-Final Rejection dated Dec. 28, 2011, 7 pages.
Co-Pending U.S. Appl. No. 12/491,151, Requirement for Restriction/Election dated Dec. 2, 2011, 6 pages.
Co-Pending U.S. Appl. No. 12/491,151, Response to Non-Final Rejection dated Mar. 28, 2012, 10 pages.
Co-Pending U.S. Appl. No. 12/491,151, Response to Requirement for Restriction/Election dated Dec. 13, 2011, 2 pages.
Co-Pending U.S. Appl. No. 12/491,151, Response with RCE to Final Rejection dated Aug. 20, 2012, 14 pages.
Co-Pending U.S. Appl. No. 12/491,151, Supplemental Amendment dated Dec. 17, 2012, 6 pages.
Co-Pending U.S. Appl. No. 12/609,779, filed Oct. 30, 2009.
Co-Pending U.S. Appl. No. 12/751,826, filed Mar. 31, 2010 (published as 2010/0250209 on Sep. 30, 2010).
Co-Pending U.S. Appl. No. 12/751,854, filed Mar. 31, 2010 (published as 2010/0249771 on Sep. 30, 2010).
Co-Pending U.S. Appl. No. 12/757,901, filed Apr. 9, 2010.
Co-Pending U.S. Appl. No. 12/906,923, filed Oct. 18, 2010.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US10/53077, filed Oct. 18, 2010.
Co-Pending Application No. PCT/US11/62067, filed Nov. 23, 2011.
Co-Pending Application No. PCT/US11/66239, filed Dec. 20, 2011.
Co-Pending U.S. Appl. No. 12/432,295, Response to Jun. 23, 2015 Non Final Office Action dated Oct. 23, 2015, 46 pages.
Alberts et al., "Molecular Biology of the Cell," 3rd edition, Garland Science, New York, 1994, 1 page.
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Asami et al., "Dielectric properties of mouse lymphocytes and erythrocytes." Biochimica et Biophysica Acta (BBA)—Molecular Cell Research, 1010 (1989) pp. 49-55.
Ball, C., K.R. Thomson, and H. Kavnoudias, "Irreversible electroporation: a new challenge in "out of-operating theater" anesthesia." Anesth Analg, 2010. 110(5): p. 1305-9.
Baptista et al., "The Use of Whole Organ Decellularization for the Generation of a Vascularized Liver Organoid," Heptatology, vol. 53, No. 2, pp. 604-617 (2011).

Bower et al., "Irreversible electroporation of the pancreas: definitive local therapy without systemic effects." Journal of surgical oncology, 2011. 104(1): p. 22-28.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Clark et al., "The electrical properties of resting and secreting pancreas." The Journal of Physiology, vol. 189, pp. 247-260 (1967).
Co-Pending U.S. Appl. No. 14/808,679, filed Jul. 24, 2015.
Co-Pending Application No. PCT/US15/30429, International Search Report and Written Opinion dated Oct. 16, 2015, 19 pages.
Dahl et al., "Nuclear shape, mechanics, and mechanotransduction." Circulation Research vol. 102, pp. 1307-1318 (2008).
Eppich et al., "Pulsed electric fields for selection of hematopoietic cells and depletion of tumor cell contaminants." Nature Biotechnology 18, pp. 882-887 (2000).
Ermolina et al., "Study of normal and malignant white blood cells by time domain dielectric spectroscopy." IEEE Transactions on Dielectrics and Electrical Insulation, 8 (2001) pp. 253-261.
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gimsa et al., "Dielectric spectroscopy of single human erythrocytes at physiological ionic strength: dispersion of the cytoplasm." Biophysical Journal, vol. 71, pp. 495-506 (1996).
Helczynska et al., "Hypoxia promotes a dedifferentiated phenotype in ductal breast carcinoma in situ." Cancer Research, vol. 63, pp. 1441-1444 (2003).
Ibey et al., "Selective cytotoxicity of intense nanosecond-duration electric pulses in mammalian cells." Biochimica Et Biophysica Acta-General Subjects, vol. 1800, pp. 1210-1219 (2010).
Jarm et al., "Antivascular effects of electrochemotherapy: implications in treatment of bleeding metastases." Expert Rev Anticancer Ther. vol. 10, pp. 729-746 (2010).
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)-Biomembranes, 471 (1977) pp. 227-242.
Kinosita et al. , "Electroporation of cell membrane visualized under a pulsed-laser fluorescence microscope." Biophysical Journal, vol. 53, pp. 1015-1019 (1988).
Kirson et al., "Alternating electric fields arrest cell proliferation in animal tumor models and human brain tumors." Proceedings of the National Academy of Sciences vol. 104, pp. 10152-10157 (2007).

(56) References Cited

OTHER PUBLICATIONS

Kotnik and Miklavcic, "Theoretical evaluation of voltage inducement on internal membranes of biological cells exposed to electric fields." Biophysical Journal, vol. 90(2), pp. 480-491 (2006).
Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).
Lebar et al., "Inter-pulse interval between rectangular voltage pulses affects electroporation threshold of artificial lipid bilayers." IEEE Transactions on NanoBioscience, vol. 1 (2002) pp. 116-120.
Maček Lebar and Miklavčič, "Cell electropermeabilization to small molecules in vitro: control by pulse parameters." Radiology and Oncology, vol. 35(3), pp. 193-202 (2001).
Malpica et al., "Grading ovarian serous carcinoma using a two-tier system." The American Journal of Surgical Pathology, vol. 28, pp. 496-504 (2004).
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Mulhall et al., "Cancer, pre-cancer and normal oral cells distinguished by dielectrophoresis." Analytical and Bioanalytical Chemistry, vol. 401, pp. 2455-2463 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Paszek et al., "Tensional homeostasis and the malignant phenotype." Cancer Cell, vol. 8, pp. 241-254 (2005).
Polak et al., "On the Electroporation Thresholds of Lipid Bilayers: Molecular Dynamics Simulation Investigations." The Journal of Membrane Biology, vol. 246, pp. 843-850 (2013).
Pucihar et al., "Numerical determination of transmembrane voltage induced on irregularly shaped cells." Annals of Biomedical Engineering, vol. 34, pp. 642-652 (2006).
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." The Journal of Urology, 180 (2008) pp. 2668-2674.
Sabuncu et al., "Dielectrophoretic separation of mouse melanoma clones." Biomicrofluidics, vol. 4, 7 pages (2010).
Salmanzadeh et al., "Investigating dielectric properties of different stages of syngeneic murine ovarian cancer cells" Biomicrofluidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Saur et al., "CXCR4 expression increases liver and lung metastasis in a mouse model of pancreatic cancer." Gastroenterology, vol. 129, pp. 1237-1250 (2005).
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Szot et al., "3D in vitro bioengineered tumors based on collagen I hydrogels." Biomaterials vol. 32, pp. 7905-7912 (2011).
Verbridge et al., "Oxygen-Controlled Three-Dimensional Cultures to Analyze Tumor Angiogenesis." Tissue Engineering, Part A vol. 16, pp. 2133-2141 (2010).
Weaver et al., "A brief overview of electroporation pulse strength-duration space: A region where additional intracellular effects are expected." Bioelectrochemistry vol. 87, pp. 236-243 (2012).
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Zhang, Y., et al., MR imaging to assess immediate response to irreversible electroporation for targeted ablation of liver tissues: preclinical feasibility studies in a rodent model. Radiology, 2010. 256(2): p. 424-32.
Co-Pending Application No. PCT/US2015/030429, Published on Nov. 19, 2015 as WO 2015/175570.
Co-Pending U.S. Appl. No. 12/432,295, Final Office Action dated Nov. 25, 2015, 14 pages.
Co-Pending U.S. Appl. No. 12/432,295, Response to Nov. 25, 2015 Final Office Action, filed Jan. 25, 2016, 12 pages.

\* cited by examiner

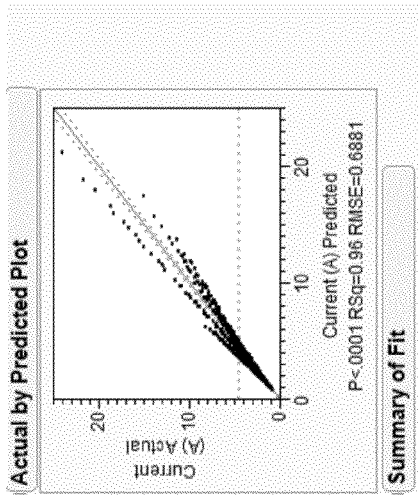
FIG. 8C
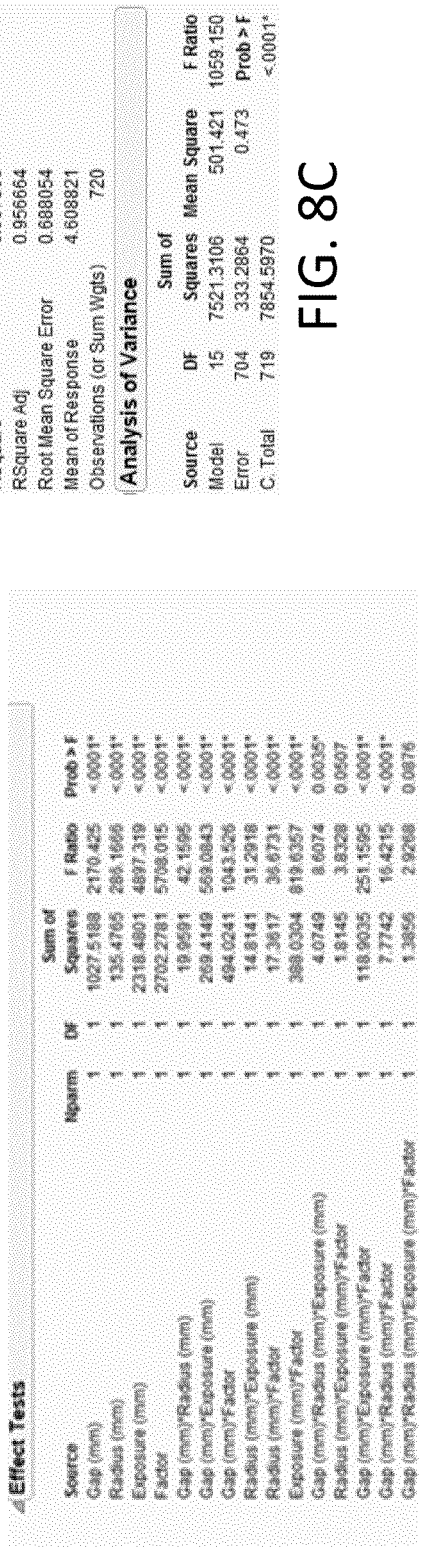
FIG. 8A
FIG. 8B

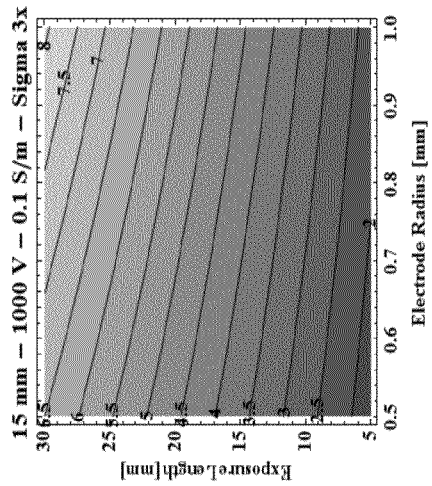
FIG. 9A
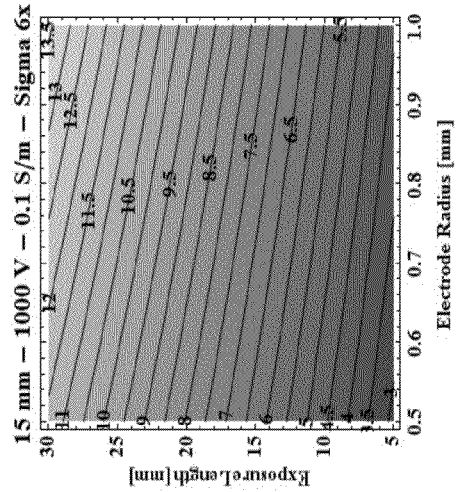
FIG. 9C
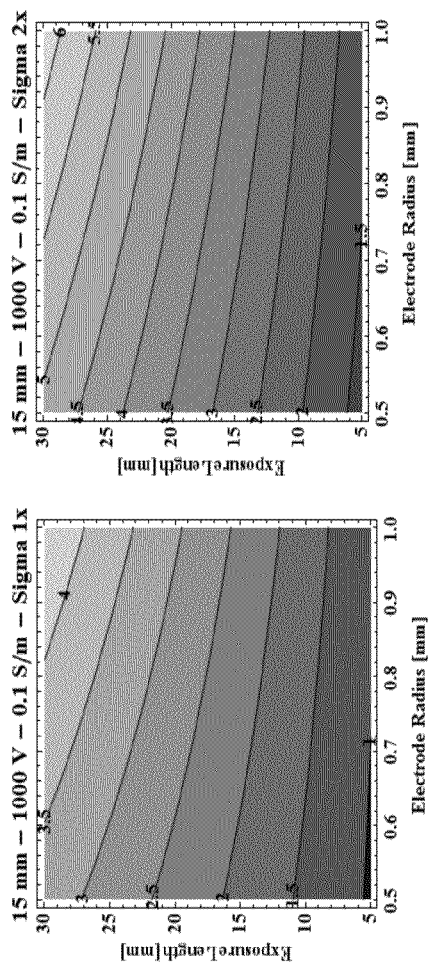
FIG. 9B
FIG. 9A
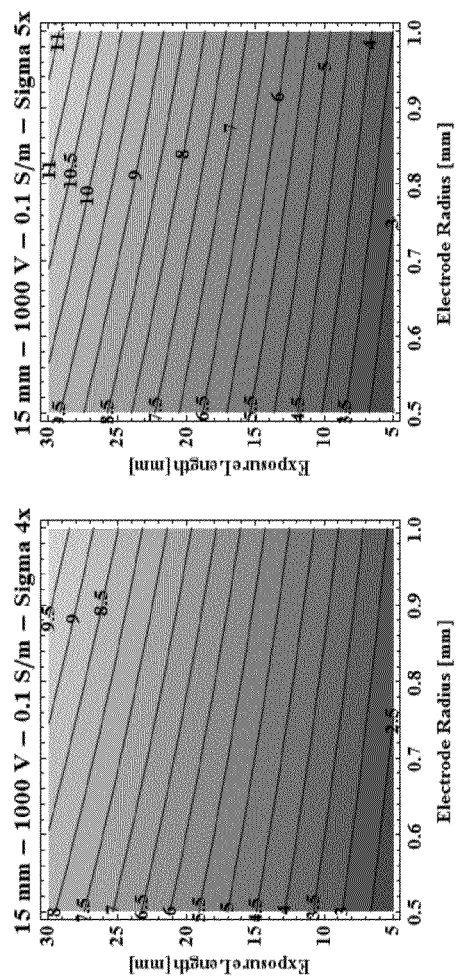
FIG. 9D
FIG. 9C
FIG. 9E

| Potato Experiment #1: | | | | Static Conductivity | | Dynamic Conductivity | | Static Conductivity | | Dynamic Conductivity | |
|---|---|---|---|---|---|---|---|---|---|---|---|
| Timing | Voltage (V) | Current (A) Onset | Current (A) End | Onset σ(S/m) | End σ(S/m) | Onset σ(S/m) | End σ(S/m) | Onset $\sigma_{applied}/\sigma_{25V}$ | End $\sigma_{applied}/\sigma_{25V}$ | Onset $\sigma_{applied}/\sigma_{25V}$ | End $\sigma_{applied}/\sigma_{25V}$ |
| Pre-IRE | 24 | - | 0.018 | - | 0.021 | - | 0.020 | - | 1.0 | - | 1.0 |
| Pre-IRE | 48 | - | 0.036 | - | 0.021 | - | 0.020 | - | 1.0 | - | 1.0 |
| Pre-IRE | 72 | - | 0.061 | - | 0.023 | - | 0.023 | - | 1.1 | - | 1.2 |
| Pre-IRE | 96 | 0.108 | 0.126 | 0.031 | 0.036 | 0.034 | 0.041 | 1.5 | 1.7 | 1.7 | 2.1 |
| Pre-IRE | 123 | 0.165 | 0.232 | 0.037 | 0.052 | 0.043 | 0.063 | 1.8 | 2.5 | 2.1 | 3.2 |
| IRE | 984 | 15.4 (1st) | 19.2 (90th) | 0.430 | 0.536 | 0.589 | 0.737 | 20.9 | 26.0 | 29.5 | 36.9 |
| Post-IRE | 24 | 0.384 | 0.348 | 0.440 | 0.399 | 0.602 | 0.545 | 21.3 | 19.3 | 30.2 | 27.3 |
| Post-IRE | 48 | 0.78 | 0.72 | 0.447 | 0.412 | 0.612 | 0.564 | 21.7 | 20.0 | 30.6 | 28.2 |
| Post-IRE | 72 | 1.2 | 1.14 | 0.458 | 0.435 | 0.628 | 0.596 | 22.2 | 21.1 | 31.4 | 29.8 |
| Post-IRE | 96 | 1.54 | 1.48 | 0.441 | 0.424 | 0.604 | 0.580 | 21.4 | 20.6 | 30.2 | 29.0 |
| Post-IRE | 120 | 1.92 | 1.86 | 0.440 | 0.426 | 0.602 | 0.583 | 21.3 | 20.7 | 30.2 | 29.2 |

FIG. 10A

Potato Experiment # 2:

| Timing | Voltage (V) | Current (A) Onset | Current (A) End | Static Conductivity Onset σ (S/m) | Static Conductivity End σ (S/m) | Dynamic Conductivity Onset σ (S/m) | Dynamic Conductivity End σ (S/m) | Static Conductivity Onset σ_applied/σ_25V | Static Conductivity End σ_applied/σ_25V | Dynamic Conductivity Onset σ_applied/σ_25V | Dynamic Conductivity End σ_applied/σ_25V |
|---|---|---|---|---|---|---|---|---|---|---|---|
| Pre-IRE | 21 | - | 0.018 | - | 0.024 | - | - | - | 1.0 | - | 1.0 |
| Pre-IRE | 48 | - | 0.036 | - | 0.021 | - | - | - | 0.9 | - | 0.8 |
| Pre-IRE | 72 | 0.071 | 0.079 | 0.027 | 0.030 | 0.026 | 0.029 | 1.2 | 1.3 | 1.2 | 1.4 |
| Pre-IRE | 96 | 0.134 | 0.17 | 0.038 | 0.049 | 0.043 | 0.058 | 1.6 | 2.1 | 1.9 | 2.5 |
| Pre-IRE | 120 | 0.24 | 0.336 | 0.055 | 0.077 | 0.066 | 0.097 | 2.3 | 3.3 | 2.9 | 4.2 |
| IRE | 996 | 14.6 (1st) | 19 (90th) | 0.403 | 0.524 | 0.550 | 0.719 | 17.1 | 22.3 | 24.1 | 31.5 |
| Post-IRE | 24 | 0.4 | 0.36 | 0.458 | 0.412 | 0.627 | 0.563 | 19.4 | 17.5 | 27.4 | 24.7 |
| Post-IRE | 48 | 0.79 | 0.74 | 0.452 | 0.424 | 0.619 | 0.579 | 19.2 | 18.0 | 27.1 | 25.4 |
| Post-IRE | 72 | 1.15 | 1.11 | 0.439 | 0.424 | 0.600 | 0.579 | 18.6 | 18.0 | 26.3 | 25.4 |
| Post-IRE | 96 | 1.6 | 1.52 | 0.458 | 0.435 | 0.627 | 0.595 | 19.4 | 18.5 | 27.4 | 26.0 |
| Post-IRE | 123 | 1.96 | 1.92 | 0.438 | 0.429 | 0.599 | 0.586 | 18.6 | 18.2 | 26.2 | 25.7 |

FIG. 10B

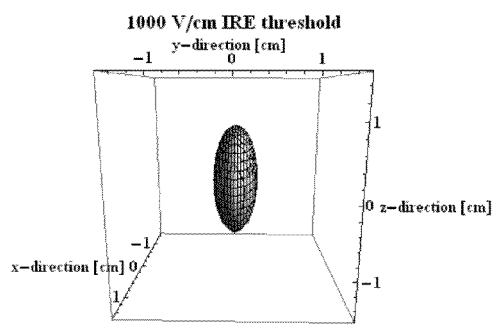 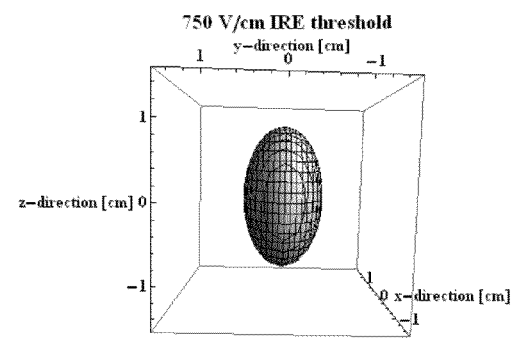
FIG. 13A  FIG. 13B
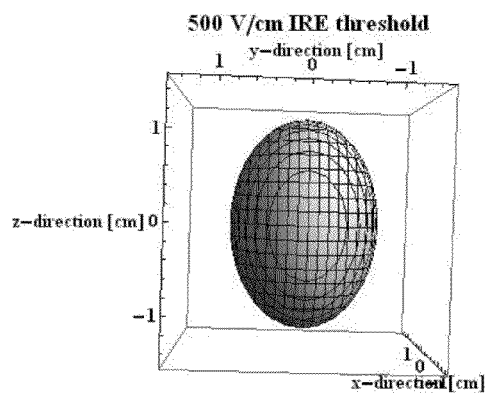
FIG. 13C

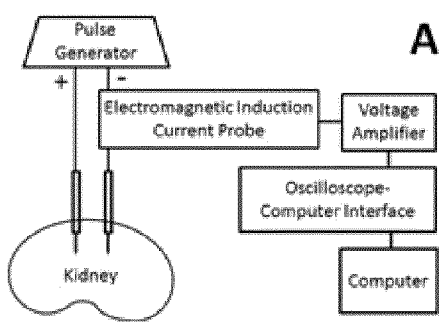
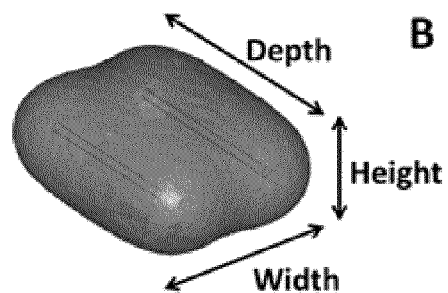
FIG. 14A
FIG. 14B
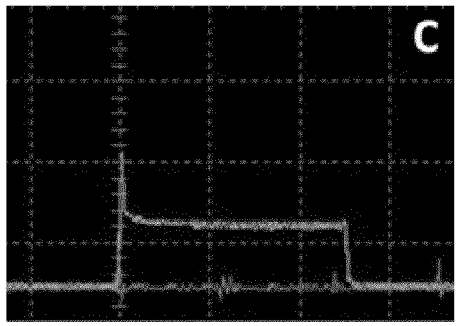
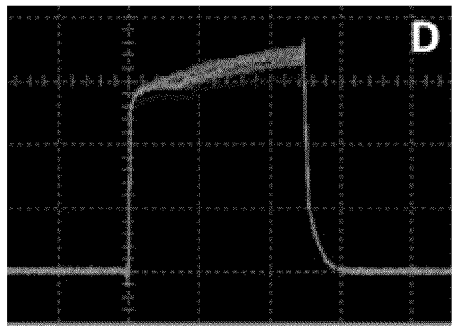
FIG. 14C
FIG. 14D

SYSTEM AND METHOD FOR ESTIMATING A TREATMENT VOLUME FOR ADMINISTERING ELECTRICAL-ENERGY BASED THERAPIES

CROSS-REFERENCE TO RELATED APPLICATIONS

The present application is a Continuation-in-Part (CIP) application of parent application U.S. application Ser. No. 12/491,151, filed on Jun. 24, 2009, which published as U.S. Patent Application Publication No. 2010/0030211 on Feb. 4, 2010 and issued as U.S. Pat. No. 8,992,517 on Mar. 31, 2015, which parent application relies on and claims the benefit of the filing dates of U.S. Provisional Patent Application Nos. 61/171,564, filed Apr. 22, 2009, 61/167,997, filed Apr. 9, 2009, and 61/075,216, filed Jun. 24, 2008, and which parent application is a Continuation-in-Part application of U.S. patent application Ser. No. 12/432,295, filed on Apr. 29, 2009, which published as U.S. Patent Application Publication No. 2009/0269317 on Oct. 29, 2009, which relies on and claims the benefit of the filing date of U.S. Provisional Patent Application No. 61/125,840, filed on Apr. 29, 2008. This application also relies on and claims the benefit of the filing date of U.S. Provisional Application No. 61/694,144, filed on Aug. 28, 2012. The disclosures of these patent applications are hereby incorporated by reference in their entireties.

FIELD OF THE INVENTION

The present invention is related to medical therapies involving the administering of electrical treatment energy. More particularly, embodiments of the present invention provide systems and methods for estimating a target ablation zone for a medical treatment device that applies electrical treatment energy through a plurality of electrodes defining a target treatment area.

DESCRIPTION OF RELATED ART

Electroporation-based therapies (EBTs) are clinical procedures that utilize pulsed electric fields to induce nanoscale defects in cell membranes. Typically, pulses are applied through minimally invasive needle electrodes inserted directly into the target tissue, and the pulse parameters are tuned to create either reversible or irreversible defects. Reversible electroporation facilitates the transport of molecules into cells without directly compromising cell viability. This has shown great promise for treating cancer when used in combination with chemotherapeutic agents or plasmid DNA (M. Marty et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006; A. I. Daud et al., "Phase I Trial of Interleukin-12 Plasmid Electroporation in Patients With Metastatic Melanoma," Journal of Clinical Oncology, 26, 5896-5903, Dec. 20, 2008). Alternatively, irreversible electroporation (IRE) has been recognized as non-thermal tissue ablation modality that produces a tissue lesion, which is visible in real-time on multiple imaging platforms (R. V. Davalos, L. M. Mir, and B. Rubinsky, "Tissue ablation with irreversible electroporation," Ann Biomed Eng, 33, 223-31, February 2005; R. V. Davalos, D. M. Otten, L. M. Mir, and B. Rubinsky, "Electrical impedance tomography for imaging tissue electroporation," IEEE Transactions on Biomedical Engineering, 51, 761-767, 2004; L. Appelbaum, E. Ben-David, J. Sosna, Y. Nissenbaum, and S. N. Goldberg, "US Findings after Irreversible Electroporation Ablation: Radiologic-Pathologic Correlation," Radiology, 262, 117-125, Jan. 1, 2012). Because the mechanism of cell death does not rely on thermal processes, IRE spares major nerve and blood vessel architecture and is not subject to local heat sink effects (B. Al-Sakere, F. Andre, C. Bernat, E. Connault, P. Opolon, R. V. Davalos, B. Rubinsky, and L. M. Mir, "Tumor ablation with irreversible electroporation," PLoS ONE, 2, e1135, 2007). These unique benefits have translated to the successful treatment of several surgically "inoperable" tumors (K. R. Thomson et al., "Investigation of the safety of irreversible electroporation in humans," J Vasc Intery Radiol, 22, 611-21, May 2011; R. E. Neal II et al., "A Case Report on the Successful Treatment of a Large Soft-Tissue Sarcoma with Irreversible Electroporation," Journal of Clinical Oncology, 29, 1-6, 2011; P. A. Garcia et al., "Non-thermal irreversible electroporation (N-TIRE) and adjuvant fractionated radiotherapeutic multimodal therapy for intracranial malignant glioma in a canine patient," Technol Cancer Res Treat, 10, 73-83, 2011).

In EBTs, the electric field distribution is the primary factor for dictating defect formation and the resulting volume of treated tissue (J. F. Edd and R. V. Davalos, "Mathematical modeling of irreversible electroporation for treatment planning," Technology in Cancer Research and Treatment, 6, 275-286, 2007 ("Edd and Davalos, 2007"); D. Miklavcic, D. Semrov, H. Mekid, and L. M. Mir, "A validated model of in vivo electric field distribution in tissues for electrochemotherapy and for DNA electrotransfer for gene therapy," Biochimica et Biophysica Acta, 1523, 73-83, 2000). The electric field is influenced by both the geometry and positioning of the electrodes as well as the dielectric tissue properties. Because the pulse duration (~100 μs) is much longer than the pulse rise/fall time (~100 ns), static solutions of the Laplace's equation incorporating only electric conductivity are sufficient for predicting the electric field distribution. In tissues with uniform conductivity, solutions can be obtained analytically for various needle electrode configurations if the exposure length is much larger than the separation distance (S. Corovic, M. Pavlin, and D. Miklavcic, "Analytical and numerical quantification and comparison of the local electric field in the tissue for different electrode configurations," Biomed Eng Online, 6, 2007; R. Neal II et al., "Experimental Characterization and Numerical Modeling of Tissue Electrical Conductivity during Pulsed Electric Fields for Irreversible Electroporation Treatment Planning," Biomedical Engineering, IEEE Transactions on, PP, 1-1, 2012 ("Neal et al., 2012")). This is not often the case in clinical applications where aberrant masses with a diameter on the order of 1 cm are treated with an electrode exposure length of similar dimensions. Additionally, altered membrane permeability due to electroporation influences the tissue conductivity in a non-linear manner. Therefore numerical techniques may be used to account for any electrode configuration and incorporate a tissue-specific function relating the electrical conductivity to the electric field distribution (i.e. extent of electroporation).

Conventional devices for delivering therapeutic energy such as electrical pulses to tissue include a handle and one or more electrodes coupled to the handle. Each electrode is connected to an electrical power source. The power source allows the electrodes to deliver the therapeutic energy to a targeted tissue, thereby causing ablation of the tissue.

Once a target treatment area is located within a patient, the electrodes of the device are placed in such a way as to create a treatment zone that surrounds the treatment target area. In some cases, each electrode is placed by hand into a patient to create a treatment zone that surrounds a lesion. The medical professional who is placing the electrodes typically watches an imaging monitor while placing the electrodes to approximate the most efficient and accurate placement.

However, if the electrodes are placed by hand in this fashion, it is very difficult to predict whether the locations selected will ablate the entire treatment target area because the treatment region defined by the electrodes vary greatly depending on such parameters as the electric field density, the voltage level of the pulses being applied, size of the electrode and the type of tissue being treated. Further, it is often difficult or sometimes not possible to place the electrodes in the correct location of the tissue to be ablated because the placement involves human error and avoidance of obstructions such as nerves, blood vessels and the like.

Conventionally, to assist the medical professional in visualizing a treatment region defined by the electrodes, an estimated treatment region is generated using a numerical model analysis such as complex finite element analysis. One problem with such a method is that even a modest two dimensional treatment region may take at least 30 minutes to several hours to complete even in a relatively fast personal computer. This means that it would be virtually impossible to try to obtain on a real time basis different treatment regions based on different electrode positions.

Therefore, it would be desirable to provide an improved system and method to predict a treatment region in order to determine safe and effective pulse protocols for administering electrical energy based therapies, such IRE.

SUMMARY OF THE INVENTION

The inventors of the present invention have made the surprising discovery that by monitoring current delivery through the electrodes placed for treatment, it is possible to determine the extent of electroporation in the tissue and accurately predict the treatment volume. In addition to current measurements, the prediction can also rely on prior knowledge of the tissue-specific conductivity function and electric field threshold for either reversible electroporation or cell death in the case of IRE.

The inventors have characterized this non-linear conductivity behavior in ex vivo porcine kidney tissue. ("Neal et al., 2012"). Using this information, the inventors performed a comprehensive parametric study on electrode exposure length, electrode spacing, voltage-to-distance ratio, and ratio between the baseline conductivity pre-IRE and maximum conductivity post-IRE. Current measurements from all 1440 possible parameter combinations were fitted to a statistical (numerical) model accounting for interaction between the pulse parameters and electrode configuration combinations. The resulting equation is capable of relating pre- and post-treatment current measurements to changes in the electric field distribution for any desired treatment protocol, such as for IRE.

The present invention provides a system for estimating a 3-dimensional treatment volume based on the numerical models developed. Various embodiments of this system are summarized below to provide an illustration of the invention.

In one embodiment, the invention provides a system for estimating a 3-dimensional treatment volume for a medical treatment device that applies treatment energy through a plurality of electrodes defining a treatment area. The system comprises a memory, a display device, a processor coupled to the memory and the display device, and a treatment planning module stored in the memory and executable by the processor. In embodiments, the treatment planning module is adapted to generate an estimated first 3-dimensional treatment volume for display in the display device based on the ratio of a maximum conductivity of the treatment area to a baseline conductivity of the treatment area.

In embodiments of the invention, the treatment planning module can be configured such that it is capable of deriving the baseline conductivity and maximum conductivity of the treatment area based on a relationship of current as a function of W, X, Y and Z, in which:

W=voltage to distance ratio;
X=edge to edge distance between electrodes;
Y=exposure length of electrode.
Z=maximum conductivity/baseline conductivity.

In embodiments, the treatment planning module is operably configured such that it is capable of deriving baseline conductivity using a pre-treatment pulse.

In embodiments of the invention, the treatment planning module generates the estimated first 3-dimensional treatment volume using a numerical model analysis.

In embodiments of the invention, the numerical model analysis includes one or more of finite element analysis (FEA), Modified Analytical Solutions to the Laplace Equation, and other Analytical Equations (e.g., Ellipsoid, Cassini curve) that fit the shape of a specific Electric Field isocontour from the FEA models either by a look-up table or interpolating analytical approximations.

In embodiments of the invention, the treatment planning module generates the estimated first 3-dimensional treatment volume using a set of second 3-dimensional ablation volumes according to different W, X, Y and Z values, which have been predetermined by a numerical model analysis.

The treatment planning module can generate the estimated first 3-dimensional treatment volume using a set of second 3-dimensional ablation volumes according to different W, X, Y and Z values, which have been pre-determined by a numerical model analysis; and generating a set of interpolated third 3-dimensional volumes based on the predetermined set of second 3-dimensional ablation volumes.

In embodiments of the invention, the treatment planning module derives by curve fitting of one or more of: a mathematical function of x values of the ablation volume as a function of any one or more of W, X, Y and/or Z; a mathematical function of y values of the ablation volume as a function of any one or more of W, X, Y and/or Z; and a mathematical function of z values of the ablation volume as a function of any one or more of W, X, Y and/or Z.

In embodiments, the treatment planning module generates the estimated first 3-dimensional treatment volume using the three mathematical functions.

In embodiments of the invention, the treatment planning module is capable of measuring a baseline and maximum conductivity of the treatment area pre-treatment; capable of generating a fourth 3-dimensional treatment volume based on the measured baseline and maximum conductivity; and capable of displaying both the first and fourth 3-dimensional treatment volumes in the display device.

In embodiments, the treatment planning module superimposes one of the first and fourth 3-dimensional treatment volumes over the other to enable a physician to compare an estimated result to an actual estimated result.

Embodiments of the invention include a method for estimating a 3-dimensional treatment volume for a medical treatment device that applies treatment energy through a plurality of electrodes define a treatment area, wherein the steps of the method are executable through a processor, the method comprising: a) Determining the baseline electric conductivity; b) Determining the maximum electric conductivity; and c) Generating an estimated first 3-dimensional treatment volume based on the ratio of the maximum conductivity of the treatment area to the baseline conductivity of the treatment area.

Included within the scope of the invention is a method for estimating a target ablation zone for a medical treatment device that applies electrical treatment energy through a plurality of electrodes defining a target treatment area, the method comprising: determining a baseline electrical flow characteristic (EFC) in response to delivery of a test signal to tissue of a subject to be treated; determining, based on the baseline EFS, a second EFC representing an expected EFC during delivery of the electrical treatment energy to the target treatment area; and estimating the target ablation zone for display in the display device based on the second EFC. Such methods can include where the step of determining a baseline EFC includes determining an electrical conductivity.

In embodiments of the invention, the baseline electric conductivity can be determined by: i) Initiating a low voltage pre-IRE pulse through a probe; ii) Measuring the current of the low voltage pre-IRE pulse through the probe; iii) Optionally, scaling the current measured in step ii. to match a voltage-to-distance ratio value; and iv) Solving for factor in the following equation provided in Example 1 to determine the baseline electric conductivity $$I = \text{factor} \cdot [aW + bX + cY + dZ + e(W-\overline{W})(X-\overline{X}) + f(W-\overline{W})(Y-\overline{Y}) + g(W-\overline{W})(Z-\overline{Z}) + h(X-\overline{X})(Y-\overline{Y}) + i(X-\overline{X})(Z-\overline{Z}) + j(Y-\overline{Y})(Z-\overline{Z}) + k(W-\overline{W})(X-\overline{X})(Y-\overline{Y}) + l(X-\overline{X})(Y-\overline{Y})(Z-\overline{Z}) + m(W-\overline{W})(Y-\overline{Y})(Z-\overline{Z}) + n(W-\overline{W})(X-\overline{X})(Z-\overline{Z}) + o(W-\overline{W})(X-\overline{X})(Y-\overline{Y})(Z-\overline{Z}) + p].$$

In embodiments of the invention, at least one high voltage IRE pulse is initiated through the probe, such as after step b, to provide an IRE treatment.

In embodiments of the invention, the maximum electric conductivity is determined after the IRE treatment by: i) Providing a low voltage post-IRE pulse through the probe; ii) Measuring the current of the low voltage post-IRE pulse through the probe; iii) Optionally, scaling the current measured in step ii. to match a voltage-to-distance value; and iv) Solving for factor in the following equation provided in Example 1 to determine the maximum electric conductivity post-IRE $$I = \text{factor} \cdot [aW + bX + cY + dZ + e(W-\overline{W})(X-\overline{X}) + f(W-\overline{W})(Y-\overline{Y}) + g(W-\overline{W})(Z-\overline{Z}) + h(X-\overline{X})(Y-\overline{Y}) + i(X-\overline{X})(Z-\overline{Z}) + j(Y-\overline{Y})(Z-\overline{Z}) + k(W-\overline{W})(X-\overline{X})(Y-\overline{Y}) + l(X-\overline{X})(Y-\overline{Y})(Z-\overline{Z}) + m(W-\overline{W})(Y-\overline{Y})(Z-\overline{Z}) + n(W-\overline{W})(X-\overline{X})(Z-\overline{Z}) + o(W-\overline{W})(X-\overline{X})(Y-\overline{Y})(Z-\overline{Z}) + p].$$

In another embodiment, the invention provides a system for estimating a target ablation zone for a medical treatment device that applies electrical treatment energy through a plurality of electrodes defining a target treatment area, the system comprising a memory, a display device, a processor coupled to the memory and the display device; and a treatment planning module stored in the memory and executable by the processor, the treatment planning module adapted to receive a baseline electrical flow characteristic (EFC) in response to delivery of a test signal to tissue of a subject to be treated, determine a second EFC representing an expected EFC during delivery of the electrical treatment energy to the target treatment area, and estimating the target ablation zone for display in the display device based on the second EFC.

In embodiments of the invention, the EFC includes an electrical conductivity.

In embodiments of the invention, the second EFC includes a maximum conductivity expected during the delivery of the electrical treatment energy to the target treatment area; and the treatment planning module estimates the target ablation zone based on the ratio of the second EFC to the baseline EFC.

In embodiments, the treatment planning module estimates the second EFC to be a multiple of the baseline EFC which is greater than 1 and less than 6.

The treatment planning module is capable of estimating the second EFC to be a multiple of the baseline EFC which is greater than 3 and less than 4.

Additionally or alternatively, the treatment planning module delivers the test signal that includes a high frequency AC signal in the range of 500 kHz and 10 MHz.

In embodiments of the invention, the treatment planning module delivers the test signal that includes an excitation AC voltage signal of 1 mV to 10 mV. The test voltage that can be applied can be in the range of from about 1 mV to about 125 V, such as from 1 V to 5 V, or from 3 V to 50 V, such as from 10 V to 100 V, or 50-125 V.

The treatment planning module in embodiments delivers the test signal that includes a low voltage non-electroporating pre-IRE pulse of 10 V/cm to 100 V/cm.

The treatment planning module in embodiments delivers the test signal that includes a low voltage non-electroporating pre-IRE pulse of 25 V/cm to 75 V/cm.

In embodiments of the invention, the treatment planning module delivers the test signal that includes the high frequency AC signal and a DC pulse.

In embodiments of the invention, the treatment planning module determines a third EFC that represents an actual EFC during delivery of the electrical treatment energy for confirmation of the estimated target ablation zone.

In embodiments of the invention, the treatment planning module determines the second EFC based on W, X and Y, in which:

W=voltage to distance ratio;
X=edge to edge distance between electrodes;
Y=exposure length of electrode.

In embodiments of the invention the treatment planning module estimates the target ablation zone based on a set of predetermined ablation zones according to different W, X, Y and Z values.

The treatment planning module can estimate the target ablation zone by curve fitting: a mathematical function of x values of the ablation volume as a function of any one or more of W, X, Y and/or Z; a mathematical function of y values of the ablation volume as a function of any one or more of W, X, Y and/or Z; and/or a mathematical function of z values of the ablation volume as a function of any one or more of W, X, Y and/or Z.

BRIEF DESCRIPTION OF THE DRAWINGS

The accompanying drawings illustrate certain aspects of embodiments of the present invention, and should not be used to limit or define the invention. Together with the written description the drawings serve to explain certain principles of the invention.

FIGS. 8A and 8B are tables showing Whole Model Parameter Estimates and Effect Tests, respectively.

FIG. 8C is a graph showing a plot of Actual Current vs. Predicted Current.

FIGS. 9A-9E are graphs showing the representative (15 mm gap) correlation between current vs. exposure length and electrode radius for maximum conductivities (1×-6×, respectively).

FIG. 10A is a table showing experimental validation of the code for determining the tissue/potato dynamic from in vitro measurements, referred to as potato experiment #1.

FIG. 10B is a table showing experimental validation of the code for determining the tissue/potato dynamic from in vitro measurements, referred to as potato experiment #2.

FIGS. 12A-12C are graphs showing representative contour plots of the electric field strength at 1.0 cm from the origin using an edge-to-edge voltage-to-distance ratio of 1500 V/cm assuming z=1, wherein FIG. 12A is a plot of the x-direction, FIG. 12B is a plot of the y-direction, and FIG. 12C is a plot of the z-direction.

FIGS. 13A-13C are 3D plots representing zones of ablation for a 1500 V/cm ratio, electrode exposure of 2 cm, and electrode separation of 1.5 cm, at respectively a 1000 V/cm IRE threshold (FIG. 13A), 750 V/cm IRE threshold (FIG. 13B), and 500 V/cm IRE threshold (FIG. 13C) using the equation for an ellipsoid.

FIG. 14A is a schematic diagram showing an experimental setup of an embodiment of the invention.

FIG. 14B is a schematic diagram showing dimension labeling conventions.

FIG. 14C is a waveform showing 50 V pre-pulse electrical current at 1 cm separation, grid=0.25 A, where the lack of rise in intrapulse conductivity suggests no significant membrane electroporation during pre-pulse delivery.

FIG. 14D is a waveform showing electrical current for pulses 40-50 of 1750 V at 1 cm separation, grid=5 A, where progressive intrapulse current rise suggests continued conductivity increase and electroporation.

FIGS. 20A-D are representations of the Electric Field [V/cm] Distributions from the 3D Non-Electroporated (Baseline) Models of FIG. 19, wherein FIG. 20A represents the x-y plane mid-electrode length, FIG. 20B represents the x-z plane mid-electrode diameter, FIG. 20C represents the y-z plane mid-electrode diameter, and FIG. 20D represents the y-z plane between electrodes.

FIGS. 22A-22D are representations of the Electric Field [V/cm] Distributions from the 3D Electroporated Models with 1.5-cm Electrodes at a Separation of 2.0 cm and 3000 V (cross-sections) assuming $\sigma_{max}/\sigma_0$=3.6, wherein FIG. 22A represents the x-y plane mid-electrode length, FIG. 22B represents the x-z plane mid-electrode diameter, FIG. 22C represents the y-z plane mid-electrode diameter, and FIG. 22D represents the y-z plane between electrodes.

DETAILED DESCRIPTION OF VARIOUS EMBODIMENTS OF THE INVENTION

Reference will now be made in detail to various exemplary embodiments of the invention. Embodiments described in the description and shown in the figures are illustrative only and are not intended to limit the scope of the invention. Changes may be made in the specific embodiments described in this specification and accompanying drawings that a person of ordinary skill in the art will recognize are within the scope and spirit of the invention.

Throughout the present teachings, any and all of the features and/or components disclosed or suggested herein, explicitly or implicitly, may be practiced and/or implemented in any combination, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Figure 1:
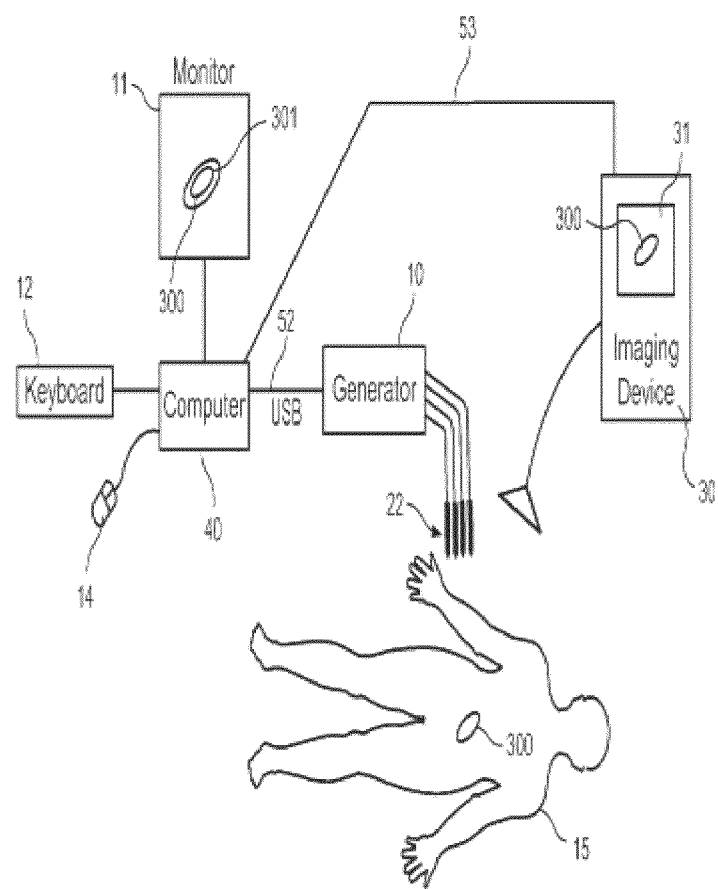
FIG. 1 is a schematic diagram of a representative system of the invention.
Figure 2:
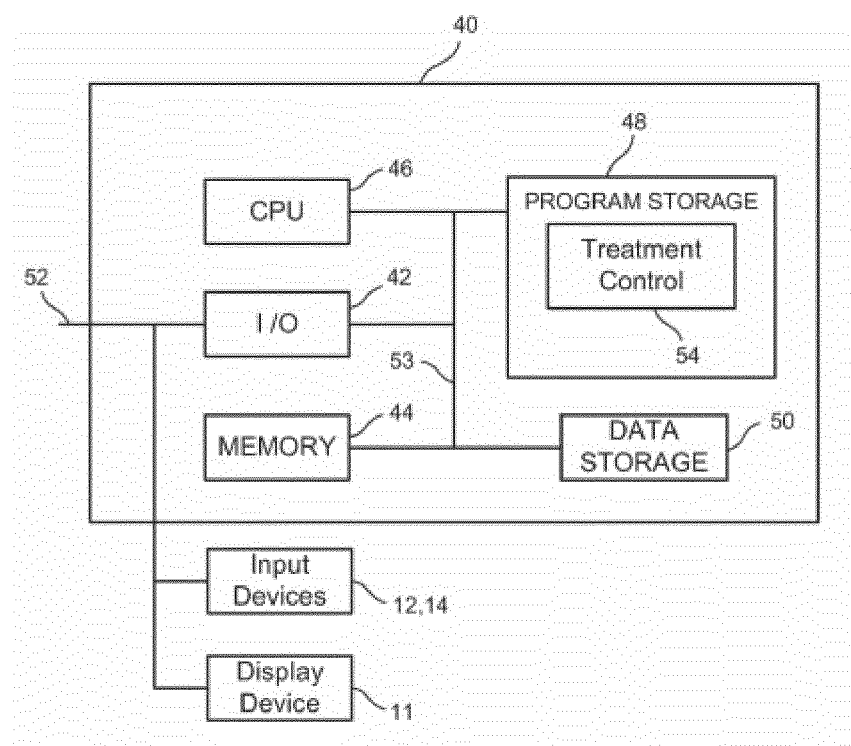
FIG. 2 is a schematic diagram of a representative treatment control computer of the invention.

One embodiment of the present invention is illustrated in FIGS. 1 and 2. Representative components that can be used with the present invention can include one or more of those that are illustrated in FIG. 1. For example, in embodiments, one or more probes 22 can be used to deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator can have any number of receptacles for receiving more or less than six probes.

For example, a treatment protocol according to the invention could include a plurality of electrodes. According to the desired treatment pattern, the plurality of electrodes can be disposed in various positions relative to one another. In a particular example, a plurality of electrodes can be disposed in a relatively circular pattern with a single electrode disposed in the interior of the circle, such as at approximately the center. Any configuration of electrodes is possible and the arrangement need not be circular but any shape periphery can be used depending on the area to be treated, including any regular or irregular polygon shape, including convex or concave polygon shapes. The single centrally located electrode can be a ground electrode while the other electrodes in the plurality can be energized. Any number of electrodes can be in the plurality such as from about 1 to 20. Indeed, even 3 electrodes can form a plurality of electrodes where one ground electrode is disposed between two electrodes capable of being energized, or 4 electrodes can be disposed in a manner to provide two electrode pairs (each pair comprising one ground and one electrode capable of being energized). During treatment, methods of treating can involve energizing the electrodes in any sequence, such as energizing one or more electrode simultaneously, and/or energizing one or more electrode in a particular sequence, such as sequentially, in an alternating pattern, in a skipping pattern, and/or energizing multiple electrodes but less than all electrodes simultaneously, for example.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein in its entirety. The pulse generator 10 is connected to a treatment control computer 40 having input devices such as keyboard 12 and a pointing device 14, and an output device such as a display device 11 for viewing an image of a target treatment area such as a lesion 300 surrounded by a safety margin 301. The therapeutic energy delivery device 22 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

The present invention includes computer software (treatment planning module 54) which assists a user to plan for, execute, and review the results of a medical treatment procedure, as will be discussed in more detail below. For example, the treatment planning module 54 assists a user to plan for a medical treatment procedure by enabling a user to more accurately position each of the probes 22 of the therapeutic energy delivery device 20 in relation to the lesion 300 in a way that will generate the most effective treatment zone. The treatment planning module 54 can display the anticipated treatment zone based on the position of the probes and the treatment parameters. The treatment planning module 54 can display the progress of the treatment in real time and can display the results of the treatment procedure after it is completed. This information can be displayed in a manner such that it can be used for example by a treating physician to determine whether the treatment was successful and/or whether it is necessary or desirable to re-treat the patient.

For purposes of this application, the terms "code", "software", "program", "application", "software code", "computer readable code", "software module", "module" and "software program" are used interchangeably to mean software instructions that are executable by a processor. The "user" can be a physician or other medical professional. The treatment planning module 54 executed by a processor outputs various data including text and graphical data to the monitor 11 associated with the generator 10.

Referring now to FIG. 2, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment planning module 54 which includes a user interface module that interacts with the user in planning for, executing and reviewing the result of a treatment. Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communications link 52. In a preferred embodiment, the communication link 52 is a USB link. In one embodiment, the imaging device 30 is a standalone device which is not connected to the computer 40. In the embodiment as shown in FIG. 1, the computer 40 is connected to the imaging device 30 through a communications link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the grid (not shown) of the display device (monitor) 11 of the computer running the treatment planning module 54. This embodiment would provide an accurate representation of the lesion image on the grid, and may eliminate the step of manually inputting the dimensions of the lesion in order to create the lesion image on the grid. This embodiment would also be useful to provide an accurate representation of the lesion image if the lesion has an irregular shape.

It should be noted that the software can be used independently of the pulse generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment. Additionally, the software can be used for hypothetical illustration of zones of ablation for training purposes to the user on therapies that deliver electrical energy. For example, the data can be evaluated by a human to determine or estimate favorable treatment protocols for a particular patient rather than programmed into a device for implementing the particular protocol.

Figure 3:
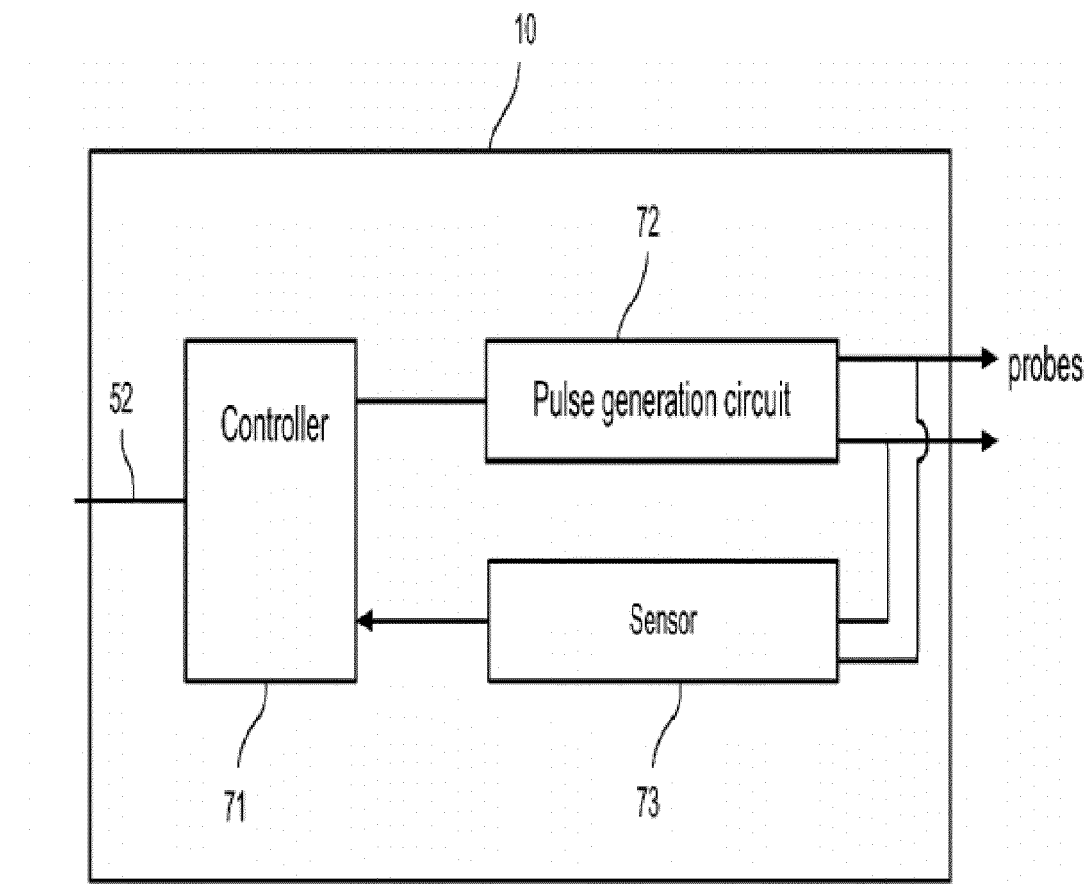
FIG. 3 is schematic diagram illustrating details of the generator shown in the system of FIG. 1, including elements for detecting an over-current condition.

FIG. 3 illustrates one embodiment of a circuitry to detect an abnormality in the applied pulses such as a high current, low current, high voltage or low voltage condition. This circuitry is located within the generator 10 (see FIG. 1). A USB connection 52 carries instructions from the user computer 40 to a controller 71. The controller can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes are shown. However, the generator 10 can accommodate any number of probes/electrodes (e.g., from 1-10, such as 6 probes) and energizing multiple electrodes simultaneously for customizing the shape of the ablation zone. In the embodiment shown, the pulses are applied one pair of electrodes at a time, and then switched to another pair. The pulse generation circuit 72 includes a switch, preferably an electronic switch, that switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes. The treatment planning module 54 can further include a feature that tracks the treatment progress and provides the user with an option to automatically retreat for low or missing pulses, or over-current pulses (see discussion below). Also, if the generator stops prematurely for any reason, the treatment planning module 54 can restart at the same point where it terminated, and administer the missing treatment pulses as part of the same treatment. In other embodiments, the treatment planning module 54 is able to detect certain errors during treatment, which include, but are not limited to, "charge failure", "hardware failure", "high current failure", and "low current failure".

General treatment protocols for the destruction (ablation) of undesirable tissue through electroporation are known. They involve the insertion (bringing) electroporation electrodes to the vicinity of the undesirable tissue and in good electrical contact with the tissue and the application of electrical pulses that cause irreversible electroporation of the cells throughout the entire area of the undesirable tissue. The cells whose membrane was irreversible permeabilized may be removed or left in situ (not removed) and as such may be gradually removed by the body's immune system. Cell death is produced by inducing the electrical parameters of irreversible electroporation in the undesirable area.

Electroporation protocols involve the generation of electrical fields in tissue and are affected by the Joule heating of the electrical pulses. When designing tissue electroporation protocols it is important to determine the appropriate electrical parameters that will maximize tissue permeabilization without inducing deleterious thermal effects. It has been shown that substantial volumes of tissue can be electroporated with reversible electroporation without inducing damaging thermal effects to cells and has quantified these volumes (Davalos, R. V., B. Rubinsky, and L. M. Mir, Theoretical analysis of the thermal effects during in vivo tissue electroporation. Bioelectrochemistry, 2003. Vol. 61(1-2): p. 99-107).

The electrical pulses used to induce irreversible electroporation in tissue are typically larger in magnitude and duration from the electrical pulses required for reversible electroporation. Further, the duration and strength of the pulses for irreversible electroporation are different from other methodologies using electrical pulses such as for intracellular electro-manipulation or thermal ablation. The methods are very different even when the intracellular (nano-seconds) electro-manipulation is used to cause cell death, e.g. ablate the tissue of a tumor or when the thermal effects produce damage to cells causing cell death.

Typical values for pulse length for irreversible electroporation are in a range of from about 5 microseconds to about 62,000 milliseconds or about 75 microseconds to about 20,000 milliseconds or about 100 microseconds±10 microseconds. This is significantly longer than the pulse length generally used in intracellular (nano-seconds) electro-manipulation which is 1 microsecond or less—see published U.S. application 2002/0010491 published Jan. 24, 2002.

The pulse is typically administered at voltage of about 100 V/cm to 7,000 V/cm or 200 V/cm to 2000 V/cm or 300V/cm to 1000 V/cm about 600 V/cm for irreversible electroporation. This is substantially lower than that used for intracellular electro-manipulation which is about 10,000 V/cm, see U.S. application 2002/0010491 published Jan. 24, 2002.

The voltage expressed above is the voltage gradient (voltage per centimeter). The electrodes may be different shapes and sizes and be positioned at different distances from each other. The shape may be circular, oval, square, rectangular or irregular etc. The distance of one electrode to another may be 0.5 to 10 cm, 1 to 5 cm, or 2-3 cm. The electrode may have a surface area of 0.1-5 sq. cm or 1-2 sq. cm.

The size, shape and distances of the electrodes can vary and such can change the voltage and pulse duration used. Those skilled in the art will adjust the parameters in accordance with this disclosure to obtain the desired degree of electroporation and avoid thermal damage to surrounding cells.

Additional features of protocols for electroporation therapy are provided in U.S. Patent Application Publication No. US 2007/0043345 A1, the disclosure of which is hereby incorporated by reference in its entirety.

The present invention provides systems and methods for estimating a 3-dimensional treatment volume for a medical treatment device that applies treatment energy through a plurality of electrodes defining a treatment area. The systems and methods are based in part on calculation of the ratio of a maximum conductivity of the treatment area to a baseline conductivity of the treatment area, and may be used to determine effective treatment parameters for electroporation-based therapies. The present inventors have recognized that the baseline and maximum conductivities of the tissue should be determined before the therapy in order to determine safe and effective pulse protocols.

The numerical models and algorithms of the invention, as provided in the Examples, such as Equation 3 of Example 1 can be implemented in a system for estimating a 3-dimensional treatment volume for a medical treatment device that applies treatment energy through a plurality of electrodes defining a treatment area. In one embodiment, the numerical models and algorithms are implemented in an appropriate computer readable code as part of the treatment planning module 54 of the system of the invention. Computing languages available to the skilled artisan for programming the treatment planning module 54 include general purpose computing languages such as the C and related languages, and statistical programming languages such as the "S" family of languages, including R and S-Plus. The computer readable code may be stored in a memory 44 of the system of the invention. A processor 46 is coupled to the memory 44 and a display device 11 and the treatment planning module 54 stored in the memory 44 is executable by the processor 46. The treatment planning module 54, through the implemented numerical models, is adapted to generate an estimated first 3-dimensional treatment volume for display in the display device 11 based on the ratio of a maximum conductivity of the treatment area to a baseline conductivity of the treatment area (Z).

In one embodiment, the invention provides for a system for estimating a 3-dimensional treatment volume for a medical treatment device that applies treatment energy through a plurality of electrodes 22 defining a treatment area, the system comprising a memory 44, a display device 11, a processor 46 coupled to the memory 44 and the display device 11, and a treatment planning module 54 stored in the memory 44 and executable by the processor 46, the treatment planning module 54 adapted to generate an estimated first 3-dimensional treatment volume for display in the display device 11 based on the ratio of a maximum conductivity of the treatment area to a baseline conductivity of the treatment area.

The foregoing description provides additional instructions and algorithms for a computer programmer to implement in computer readable code a treatment planning module 54 that may be executable through a processor 46 to generate an estimated 3-dimensional treatment volume for display in the display device 11 based on the ratio of a maximum conductivity of the treatment area to a baseline conductivity of the treatment area.

The treatment planning module 54 may derive the baseline conductivity and maximum conductivity of the treatment area based on a relationship of current as a function of W, X, and Y, in which:

W=voltage to distance ratio;
X=edge to edge distance between electrodes; and
Y=exposure length of electrode.

The treatment planning module 54 may derive the baseline conductivity using a pre-treatment pulse.

The treatment planning module 54 may generate the estimated first 3-dimensional treatment volume using a numerical model analysis such as described in the Examples. The numerical model analysis may include finite element analysis (FEA).

The treatment planning module 54 may generate the estimated first 3-dimensional treatment volume using a set of second 3-dimensional ablation volumes according to different W, X, Y and Z values, which have been predetermined by the numerical model analysis.

The treatment planning module 54 may generate the estimated first 3-dimensional treatment volume using a set of second 3-dimensional ablation volumes according to different W, X, Y and Z values, which have been pre-determined by a numerical model analysis; and generating a set of interpolated third 3-dimensional volumes based on the predetermined set of second 3-dimensional ablation volumes.

The treatment planning module 54 may derive by curve fitting: a mathematical function of x values of the ablation volume as a function of any one or more of W, X, Y and/or Z; a mathematical function of y values of the ablation volume as a function of any one or more of W, X, Y and/or Z; and/or a mathematical function of z values of the ablation volume as a function of any one or more of W, X, Y and/or Z.

The treatment planning module 54 may generate the estimated first 3-dimensional treatment volume using the three mathematical functions.

The treatment planning module 54 may: measure a baseline and maximum conductivity of the treatment area; generate a fourth 3-dimensional treatment volume based on the measured baseline and maximum conductivity; and optionally display one or both the first and fourth 3-dimensional treatment volumes in the display device 11.

The treatment planning module 54 may superimpose one of the first and fourth 3-dimensional treatment volumes over the other so as to enable a physician to compare an estimated result to an actual estimated result.

In another embodiment, the invention provides a system for estimating a target ablation zone for a medical treatment device that applies electrical treatment energy through a plurality of electrodes 22 defining a target treatment area, the system comprising a memory 44, a display device 11, a processor 46 coupled to the memory 44 and the display device 11; and a treatment planning module 54 stored in the memory 44 and executable by the processor 46, the treatment planning module 54 adapted to receive a baseline electrical flow characteristic (EFC) in response to delivery of a test signal to tissue of a subject 15 to be treated, determine a second EFC representing an expected EFC during delivery of the electrical treatment energy to the target treatment area, and estimating the target ablation zone for display in the display device 11 based on the second EFC. The EFC may include an electrical conductivity.

The second EFC may include a maximum conductivity expected during the delivery of the electrical treatment energy to the target treatment area; and the treatment planning module estimates the target ablation zone based on the ratio of the second EFC to the baseline EFC.

The treatment planning module 54 may estimate the second EFC to be a multiple of the baseline EFC which is greater than 1 and less than 6.

The treatment planning module 54 may estimate the second EFC to be a multiple of the baseline EFC which is greater than 3 and less than 4.

The treatment planning module 54 may deliver the test signal that includes a high frequency AC signal in the range of 500 kHz and 10 MHz.

The treatment planning module 54 may deliver the test signal that includes an excitation AC voltage signal of 1 to 10 mV, such as from 1 mV to 125 V, including for example from about 1 to 5 V, or from about 10-50 V, or from about 100-125 V.

The treatment planning module may deliver the test signal that includes a low voltage non-electroporating pre-IRE pulse of 10 V/cm to 100 V/cm.

The treatment planning module may deliver the test signal that includes a low voltage non-electroporating pre-IRE pulse of 25 V/cm to 75 V/cm.

The treatment planning module 54 may deliver the test signal that includes the high frequency AC signal and a DC pulse.

The treatment planning module 54 may determines a third EFC that represents an actual EFC during delivery of the electrical treatment energy for confirmation of the estimated target ablation zone.

The treatment planning module 54 may determine the second EFC based on W, X and Y, in which: W=voltage to distance ratio; X=edge to edge distance between electrodes; Y=exposure length of electrode.

The treatment planning module 54 may be operably configured to estimate the target ablation zone based on a set of predetermined ablation zones according to different W, X, Y and Z values.

The treatment planning module may estimate the target ablation zone by curve fitting: a mathematical function of x values of the ablation volume as a function of any one or more of W, X, Y and/or Z; a mathematical function of y values of the ablation volume as a function of any one or more of W, X, Y and/or Z; and/or a mathematical function of z values of the ablation volume as a function of any one or more of W, X, Y and/or Z.

Figure 4:
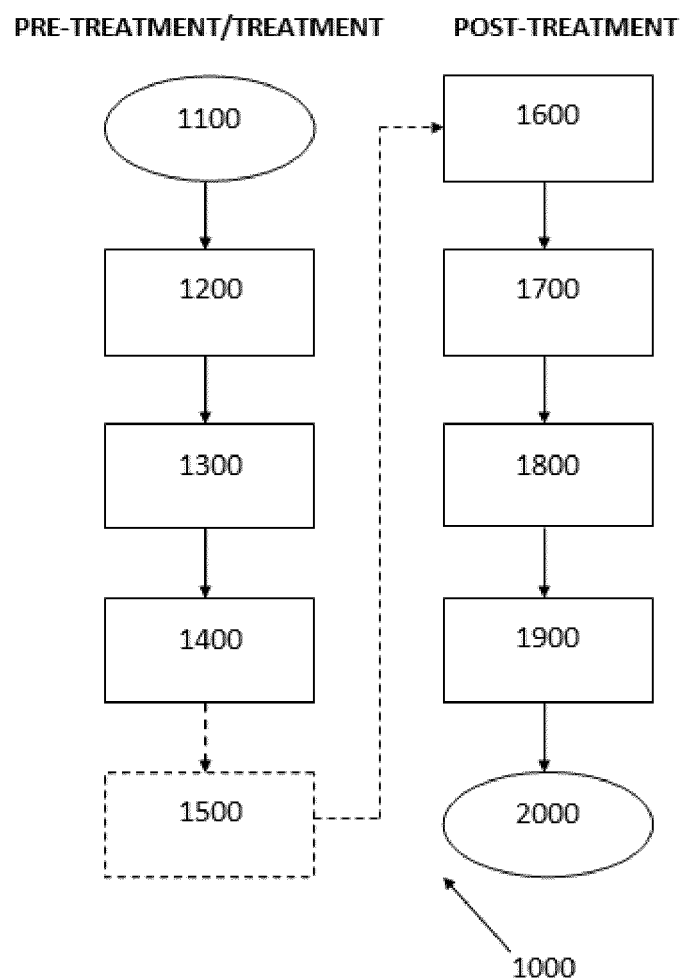
FIG. 4 is a flow chart illustrating a method, e.g., algorithm, of the invention.

The treatment planning module 54 is programmed to execute the algorithms disclosed herein through the processor 46. In one embodiment, the treatment planning module 54 is programmed to execute the following algorithm 1000, as shown in FIG. 4, in computer readable code through the processor 46:

Initiating a low voltage pre-IRE pulse through a probe 1100;

Measuring the current of the low voltage pre-IRE pulse through probe 1200;

Optionally, scaling the current measured in step 1200 to match a voltage-to-distance ratio value 1300;

Solving 1400 for factor in the following equation provided in Example 1 to determine the baseline electric conductivity $$I = \text{factor} \cdot [aW + bX + cY + dZ + e(W-\overline{W})(X-\overline{X}) + f(W-\overline{W})(Y-\overline{Y}) + g(W-\overline{W})(Z-\overline{Z}) + h(X-\overline{X})(Y-\overline{Y}) + i(X-\overline{X})(Z-\overline{Z}) + j(Y-\overline{Y})(Z-\overline{Z}) + k(W-\overline{W})(X-\overline{X})(Y-\overline{Y}) + l(X-\overline{X})(Y-\overline{Y})(Z-\overline{Z}) + m(W-\overline{W})(Y-\overline{Y})(Z-\overline{Z}) + n(W-\overline{W})(X-\overline{X})(Z-\overline{Z}) + o(W-\overline{W})(X-\overline{X})(Y-\overline{Y})(Z-\overline{Z}) + p]$$

Providing at least one high voltage IRE pulse through the probe to provide an IRE treatment 1500;

Providing a low voltage post-IRE pulse through the probe 1600;

Measuring the current of the low voltage post-IRE pulse through probe 1700;

Optionally, scaling the current measured in step 1700 to match a voltage-to-distance value 1800;

Solving 1900 for factor in the following equation provided in Example 1 to determine the maximum electric conductivity post-IRE $$I = \text{factor} \cdot [aW + bX + cY + dZ + e(W-\overline{W})(X-\overline{X}) + f(W-\overline{W})(Y-\overline{Y}) + g(W-\overline{W})(Z-\overline{Z}) + h(X-\overline{X})(Y-\overline{Y}) + i(X-\overline{X})(Z-\overline{Z}) + j(Y-\overline{Y})(Z-\overline{Z}) + k(W-\overline{W})(X-\overline{X})(Y-\overline{Y}) + l(X-\overline{X})(Y-\overline{Y})(Z-\overline{Z}) + m(W-\overline{W})(Y-\overline{Y})(Z-\overline{Z}) + n(W-\overline{W})(X-\overline{X})(Z-\overline{Z}) + o(W-\overline{W})(X-\overline{X})(Y-\overline{Y})(Z-\overline{Z}) + p]$$

Generating an estimated first 3-dimensional treatment volume based on the ratio of the maximum conductivity of the treatment area to the baseline conductivity of the treatment area 2000.

The steps in the algorithm 1000 shown in FIG. 4 need not be followed exactly as shown. For example, it may be desirable to eliminate one or both scaling steps 1300, 1800. It may also be desirable to introduce or substitute steps, such as, for example, providing a mathematical function of x, y, z values of the 3-dimensional treatment volume as a function of any one or more of W, X, Y, and/or Z by curve fitting, and estimating the 3-dimensional treatment volume using the three mathematical functions, or introducing additional steps disclosed herein.

For example, specific method embodiments of the invention include a method for estimating a target ablation zone for a medical treatment device that applies electrical treatment energy through a plurality of electrodes defining a target treatment area, the method comprising: determining a baseline electrical flow characteristic (EFC) in response to delivery of a test signal to tissue of a subject to be treated; determining, based on the baseline EFS, a second EFC representing an expected EFC during delivery of the electrical treatment energy to the target treatment area; and estimating the target ablation zone for display in the display device based on the second EFC.

Such methods can include where the step of determining a baseline EFC includes determining an electrical conductivity.

Additionally or alternatively, such methods can include where the step of determining a second EFC includes determining an expected maximum electrical conductivity during delivery of the electrical treatment energy to the target treatment area; and the step of estimating includes estimating the target ablation zone based on the ratio of the second EFC to the baseline EFC.

Even further, the treatment planning module in method and system embodiments can estimate the second EFC to be a multiple of the baseline EFC which is greater than 1 and less than 6. For example, the treatment planning module can estimate the second EFC to be a multiple of the baseline EFC which is greater than 3 and less than 4.

Methods of the invention are provided wherein the treatment planning module delivers the test signal that includes a high frequency AC signal in the range of 500 kHz and 10 MHz. Alternatively or in addition methods can include wherein the treatment planning module delivers the test signal that includes the high frequency AC signal and a DC pulse.

In method embodiments of the invention, the treatment planning module determines a third EFC that represents an actual EFC during delivery of the electrical treatment energy for confirmation of the estimated target ablation zone.

Methods of the invention can comprise displaying results of treatment in a manner which indicates whether treatment was successful or whether further treatment is needed. Method steps can include further delivering electrical treatment energy to a target tissue or object in response to data obtained in the determining and/or estimating steps of methods of the invention.

According to embodiments, a method is provided for estimating a target ablation zone, the method comprising: determining a baseline electrical flow characteristic (EFC) in response to delivery of a test signal to a target area of an object; determining, based on the baseline EFS, a second EFC representing an expected EFC during delivery of the electrical treatment energy to the target area; estimating the target ablation zone for display in the display device based on the second EFC. For example, according to such methods the object can be a biological object, such as tissue, a non-biological object, such as a phantom, or any object or material such as plant material.

Systems and methods of the invention can comprise a treatment planning module adapted to estimate the target ablation zone based in part on electrode radius and/or a step of estimating the target ablation zone based in part on electrode radius.

In embodiments of the methods, the treatment planning module determines the second EFC based on W, X and Y, in which: W=voltage to distance ratio; X=edge to edge distance between electrodes; and Y=exposure length of electrode.

The treatment planning module of method embodiments can estimate the target ablation zone based on a set of predetermined ablation zones according to different W, X and Y values.

Method embodiments further include that the treatment planning module estimates the target ablation zone by curve fitting: a mathematical function of x values of the ablation volume as a function of any one or more of W, X and/or Y; a mathematical function of y values of the ablation volume as a function of any one or more of W, X and/or Y; and a mathematical function of z values of the ablation volume as a function of any one or more of W, X and/or Y.

The system may be further configured to include software for displaying a Graphical User Interface in the display device with various screens for input and display of information, including those for Information, Probe Selection, Probe Placement Process, and Pulse Generation as described in International Patent Application Publication WO 2010/117806 A1, the disclosure of which is hereby incorporated by reference in its entirety.

Additional details of the algorithms and numerical models disclosed herein will be provided in the following Examples, which are intended to further illustrate rather than limit the invention.

In Example 1, the present inventors provide a numerical model that uses an asymmetrical Gompertz function to describe the response of porcine renal tissue to electroporation pulses. However, other functions could be used to represent the electrical response of tissue under exposure to pulsed electric fields such as a sigmoid function, ramp, and/or interpolation table. This model can be used to determine baseline conductivity of tissue based on any combination of electrode exposure length, separation distance, and non-electroporating electric pulses. In addition, the model can be scaled to the baseline conductivity and used to determine the maximum electric conductivity after the electroporation-based treatment. By determining the ratio of conductivities pre- and post-treatment, it is possible to predict the shape of the electric field distribution and thus the treatment volume based on electrical measurements. An advantage of this numerical model is that it is easy to implement in computer software code in the system of the invention and no additional electronics or numerical simulations are needed to determine the electric conductivities. The system and method of the invention can also be adapted for other electrode geometries (sharp electrodes, bipolar probes), electrode diameter, and other tissues/tumors once their response to different electric fields has been fully characterized.

The present inventors provide further details of this numerical modeling as well as experiments that confirm this numerical modeling in Example 2. In developing this work, the present inventors were motivated to develop an IRE treatment planning method and system that accounts for real-time voltage/current measurements. As a result of this work, the system and method of the invention requires no electronics or electrodes in addition to the NANOKNIFE® System, a commercial embodiment of a system for electroporation-based therapies. The work shown in Example 2 is based on parametric study using blunt tip electrodes, but can be customized to any other geometry (sharp, bipolar). The numerical modeling in Example 2 provides the ability to determine a baseline tissue conductivity based on a low voltage pre-IRE pulse (non-electroporating~50 V/cm), as well as the maximum tissue conductivity based on high voltage IRE pulses (during electroporation) and low voltage post-IRE pulse (non-electroporating~50 V/cm). Two numerical models were developed that examined 720 or 1440 parameter combinations. Results on IRE lesion were based on in vitro measurements. A major finding of the modeling in Example 2 is that the electric field distribution depends on conductivity ratio pre- and post-IRE. Experimental and clinical IRE studies may be used to determine this ratio. As a result, one can determine e-field thresholds for tissue and tumor based on measurements. The 3-D model of Example 2 captures depth, width, and height e-field distributions.

In Example 3, as a further extension of the inventors work, the inventors show prediction of IRE treatment volume based on 1000 V/cm, 750 v/cm, and 500 V/cm IRE thresholds as well as other factors as a representative case of the numerical modeling of the invention.

In Example 4, the inventors describe features of the Specific Conductivity and procedures for implementing it in the invention.

In Example 5, the inventors describe in vivo experiments as a reduction to practice of the invention.

In Example 6, the inventors describe how to use the ratio of maximum conductivity to baseline conductivity in modifying the electric field distribution and thus the Cassini oval equation.

In Example 7, the inventors describe the Cassini oval equation and its implementation in the invention.

EXAMPLES

Example 1

Materials and Methods

The tissue was modeled as a 10-cm diameter spherical domain using a finite element package (Comsol 4.2a, Stockholm, Sweden). Electrodes were modeled as two 1.0-mm diameter blunt tip needles with exposure lengths (Y) and edge-to-edge separation distances (X) given in Table 1. The electrode domains were subtracted from the tissue domain, effectively modeling the electrodes as boundary conditions.

TABLE 1

Electrode configuration and relevant electroporation-based treatment values used in study.

| | PARAMETER VALUES | MEAN |
|---|---|---|
| W [V/cm] | 500, 1000, 1500, 2000, 2500, 3000 | 1750 |
| X [cm] | 0.5, 1.0, 1.5, 2.0, 2.5 | 1.5 |
| Y [cm] | 0.5, 1.0, 1.5, 2.0, 2.5, 3.0 | 1.75 |
| Z [cm] | 1.0, 1.25, 1.5, 2.0, 3.0, 4.0, 5.0, 6.0 | 2.968 75 |

The electric field distribution associated with the applied pulse is given by solving the Laplace equation:

$$\nabla \cdot (\sigma(|E|)\nabla \phi) = 0 \quad (1)$$

where $\sigma$ is the electrical conductivity of the tissue, E is the electric field in V/cm, and $\phi$ is the electrical potential (Edd and Davalos, 2007). Boundaries along the tissue in contact with the energized electrode were defined as $\phi = V_o$, and boundaries at the interface of the other electrode were set to ground. The applied voltages were manipulated to ensure that the voltage-to-distance ratios (W) corresponded to those in Table 1. The remaining boundaries were treated as electrically insulating, $\partial \phi / \partial n = 0$.

Figure 5:
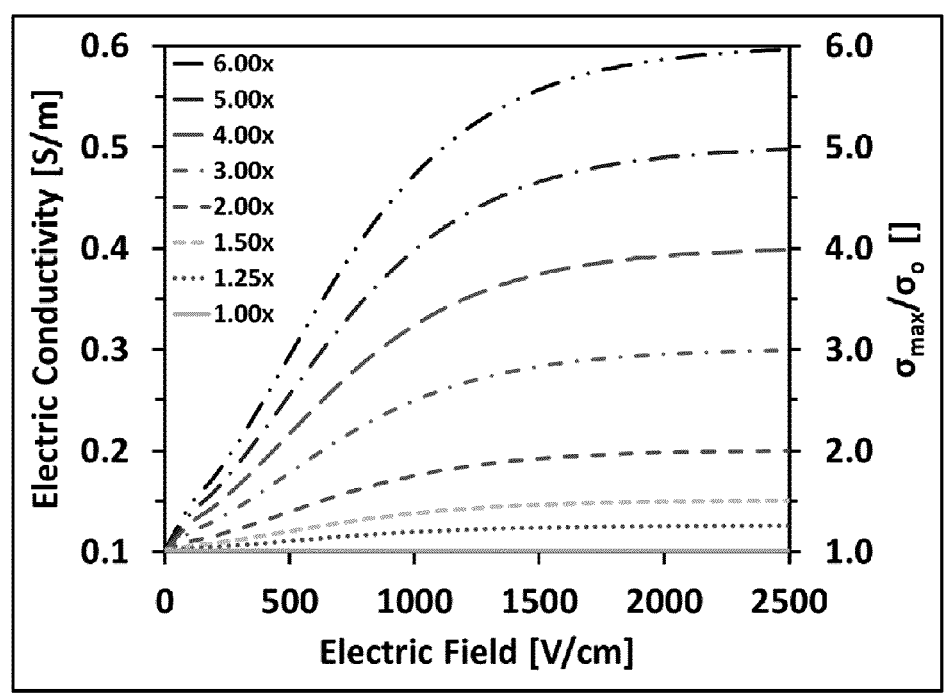
FIG. 5 is a graph of the asymmetrical Gompertz function showing tissue electric conductivity as a function of electric field.

The analyzed domain extends far enough from the area of interest (i.e. the area near the electrodes) that the electrically insulating boundaries at the edges of the domain do not significantly influence the results in the treatment zone. The physics-controlled finer mesh with ~100,000 elements was used. The numerical models have been adapted to account for a dynamic tissue conductivity that occurs as a result of electroporation, which is described by an asymmetrical Gompertz curve for renal porcine tissue (Neal et al., 2012):

$$\sigma(|E|)=\sigma_o+(\sigma_{max}-\sigma_o)\exp[A\cdot\exp[-B\cdot E]] \quad (2)$$

where $\sigma_o$ is the non-electroporated tissue conductivity and $\sigma_{max}$ is the maximum conductivity for thoroughly permeabilized cells, A and B are coefficients for the displacement and growth rate of the curve, respectively. Here, it is assumed that $\sigma_o$=0.1 S/m but this value can be scaled by a factor to match any other non-electroporated tissue conductivity or material as determined by a pre-treatment pulse. In this work the effect of the ratio of maximum conductivity to baseline conductivity in the resulting electric current was examined using the 50-μs pulse parameters (A=3.05271; B=0.00233) reported by Neal et al. (Neal et. al., 2012). The asymmetrical Gompertz function showing the tissue electric conductivity as a function of electric field is for example shown in FIG. 5.

The current density was integrated over the surface of the ground electrode to determine the total current delivered. A regression analysis on the resulting current was performed to determine the effect of the parameters investigated and their interactions using the NonlinearModelFit function in Wolfram Mathematica 8.0. Current data from the numerical simulations were fit to a mathematical expression that accounted for all possible interactions between the parameters:

$$I=\text{factor}\cdot[aW+bX+cY+dZ+e(W-\overline{W})(X-\overline{X})+f(W-\overline{W})(Y-\overline{Y})+g(W-\overline{W})(Z-\overline{Z})+h(X-\overline{X})(Y-\overline{Y})+i(X-\overline{X})(Z-\overline{Z})+j(Y-\overline{Y})(Z-\overline{Z})+k(W-\overline{W})(X-\overline{X})(Y-\overline{Y})+l(X-\overline{X})(Y-\overline{Y})(Z-\overline{Z})+m(W-\overline{W})(Y-\overline{Y})(Z-\overline{Z})+n(W-\overline{W})(X-\overline{X})(Z-\overline{Z})+o(W-\overline{W})(X-\overline{X})(Y-\overline{Y})(Z-\overline{Z})+p] \quad (3)$$

where I is the current in amps, W is the voltage-to-distance ratio [V/cm], X is the edge-to-edge distance [cm], Y is the exposure length [cm], and Z is the unitless ratio $\sigma_{max}/\sigma_o$. The $\overline{W}$, $\overline{X}$, $\overline{Y}$, and $\overline{Z}$ are means for each of their corresponding parameters (Table 1) and the coefficients (a, b, c, . . . , n, o, p) were determined from the regression analysis (Table 2).

Results.

A method to determine electric conductivity change following treatment based on current measurements and electrode configuration is provided. The best-fit statistical (numerical) model between the W, X, Y, and Z parameters resulted in Eqn. 3 with the coefficients in Table 2 ($R^2$=0.999646). Every coefficient and their interactions had statistical significant effects on the resulting current ($P<0.0001^*$). With this equation one can predict the current for any combination of the W, Y, X, Z parameters studied within their ranges (500 V/cm≤W≤3000 V/cm, 0.5 cm≤X≤2.5 cm, 0.5 cm≤Y≤3.0 cm, and 1.0≤Z≤6.0). Additionally, by using the linear results (Z=1), the baseline tissue conductivity can be extrapolated for any blunt-tip electrode configuration by delivering and measuring the current of a non-electroporating pre-treatment pulse. The techniques described in this specification could also be used to determine the conductivity of other materials, such as non-biological materials, or phantoms.

TABLE 2

Coefficients (P < 0.0001*) from the Least Square analysis using the NonlinearModelFit function in Mathematica.

| | ESTIMATE |
|---|---|
| a → | 0.00820 |
| b → | 7.18533 |
| c → | 5.80997 |
| d → | 3.73939 |

TABLE 2-continued

Coefficients (P < 0.0001*) from the Least Square analysis using the NonlinearModelFit function in Mathematica.

| | ESTIMATE |
|---|---|
| e → | 0.00459 |
| f → | 0.00390 |
| g → | 0.00271 |
| h → | 3.05537 |
| i → | 2.18763 |
| j → | 1.73269 |
| k → | 0.00201 |
| l → | 0.92272 |
| m → | 0.00129 |
| n → | 0.00152 |
| o → | 0.00067 |
| p → | −33.92640 |

Figure 6:
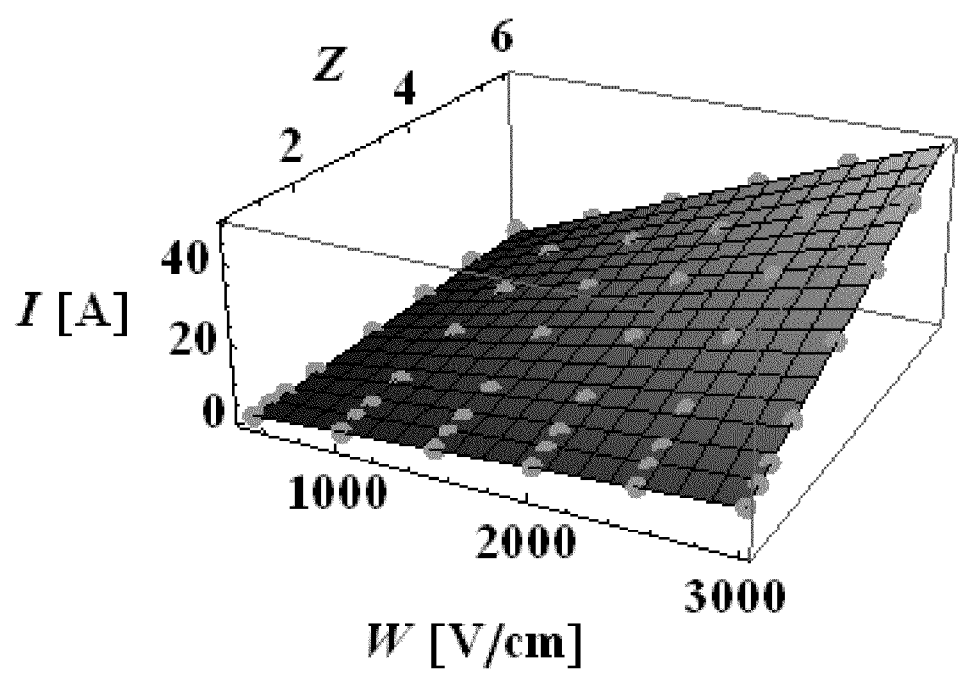
FIG. 6 is a graph showing a representative 3D plot of current [A] as a function of Z ($\sigma_{max}/\sigma_o$) and voltage-to-distance ratio (W) for a separation distance of 1.5 cm and an electrode exposure length of 2.0 cm as used by Ben-David et al.

FIG. 6 shows a representative case in which the effect of the W and Z are studied for electroporation-based therapies with 2.0 cm electrodes separated by 1.5 cm. The 3D plot corroborates the quality of the model which shows every data point from the numerical simulation (green spheres) being intersected by the best-fit statistical (numerical) model. This 3D plot also shows that when Z is kept constant, the current increases linearly with the voltage-to-distance ratio (W). Similarly, the current increases linearly with Z when the voltage-to-distance ratio is constant. However, for all the other scenarios there is a non-linear response in the current that becomes more drastic with simultaneous increases in W and Z.

Figure 7A:
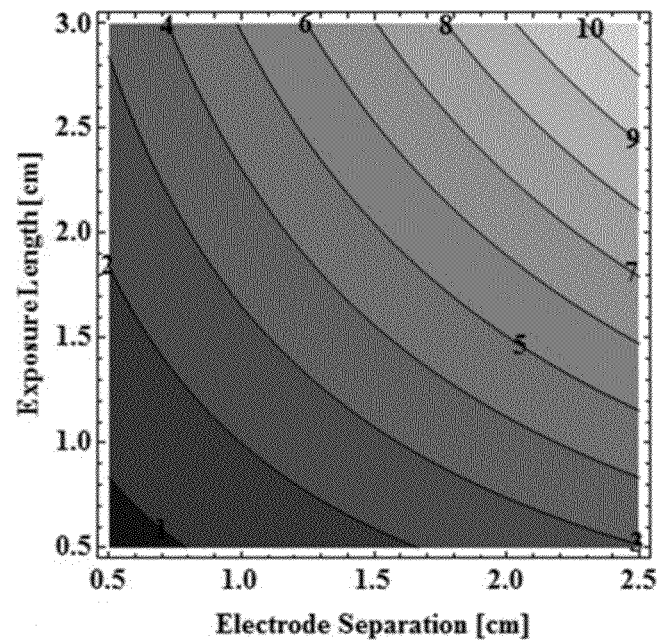
FIGS. 7A and 7B are graphs showing representative contour plots of current [A] as a function of electrode exposure and separation distance using 1500 V/cm for Z=1 (FIG. 7A) and Z=4 (FIG. 7B).
Figure 7B:
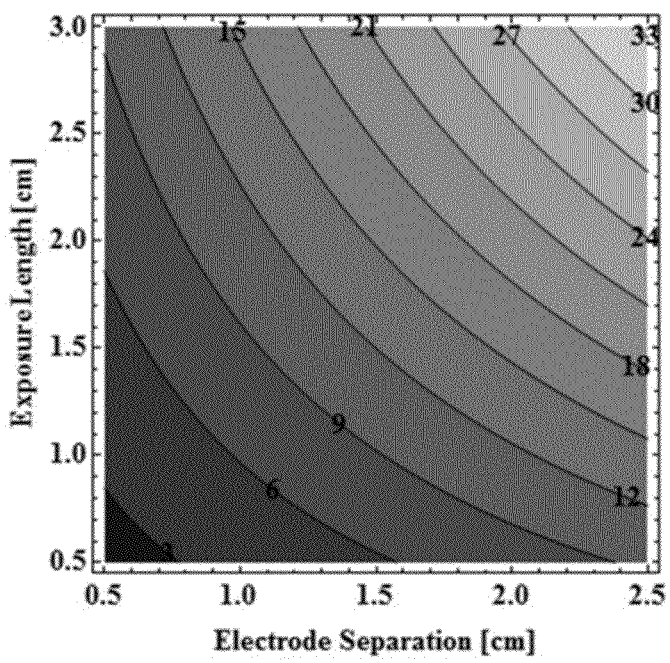

In order to fully understand the predictive capability of the statistical (numerical) model, two cases in which the current is presented as a function of the exposure length and electrode separation are provided. FIG. 7A shows the linear case (Z=1) in which the current can be scaled to predict any other combination of pulse parameters as long as the pulses do not achieve electroporation. For example, one can deliver a non-electroporation pulse (~50 V/cm) and measure current. The current can then be scaled to match one of the W values investigated in this study. By using Eqn. 3 and solving for the factor, the baseline electric conductivity of the tissue can be determined and used for treatment planning. FIG. 7B is the case in which the maximum electric conductivity was 0.4 S/m (Z=4) after electroporation. The trends are similar to the ones described in FIG. 5 in that if exposure length is constant, the current increases linearly with increasing electrode separation and vice versa. However, even though the conductivity within the treated region increases by a factor of 4, the current increases non-linearly only by a factor of 3. This can be seen by comparing the contours in FIG. 7A with those in FIG. 7B which consistently show that the curves are increased by a factor of 3.

Example 2

Determining the Relationship Between Blunt Tip Electrode Configuration and Resulting Current after IRE Treatment Model Assumptions:

Gompertz Conductivity: Pulse duration=50 μs, Ex-vivo kidney tissue

Baseline Conductivity: σ=0.1 S/m

Spherical Domain: diameter=10 cm

Applied Voltage: Voltage=1000 V
Parametric Study:
Total Combinations: 720 models
Maximum Conductivity: 1.0×, 1.25×, 1.5×, 2×, 3×, 4×, 5×, 6× the baseline
Edge-to-edge Distance: 5, 10, 15, 20, 25 mm
Electrode Exposure: 5, 10, 15, 20, 25, 30 mm
Electrode Radius: 0.5, 0.75, 1.0 mm The output of statistical analysis software (JMP 9.0) used to fit model and determine the coefficients for all parameter combinations is shown in the tables of FIGS. 8A and 8B and the plot of FIG. 8C.

Parameters of Best Fit for Dynamic Conductivity Changes Between 1×-6× the Baseline Conductivity ($R^2$=0.96):
a=−1.428057; (*Intercept Estimate*)
b=−0.168944; (*Gap Estimate*)
c=2.1250608; (*Radius Estimate*)
d=0.2101464; (*Exposure Estimate*)
e=1.1114726; (*Factor Estimate*)
f=−0.115352; (*Gap−Radius Estimate*)
g=−0.010131; (*Gap−Exposure Estimate*)
h=−0.067208; (*Gap−Factor*)
i=0.0822932; (*Radius−Exposure Estimate*)
j=0.4364513; (*Radius−Factor Estimate*)
k=0.0493234; (*Exposure−Factor Estimate*)
l=−0.006104; (*Gap−Radius−Exposure Estimate*)
m=0.0165237; (*Radius−Exposure−Factor Estimate*)*)
n=−0.003861; (*Gap−Exposure−Factor Estimate*)
o=−0.041303; (*Gap−Radius−Factor Estimate*)
p=−0.002042; (*Gap−Radius−Exposure−Factor Estimate*)

Analytical Function for Dynamic Conductivity Changes Between 1×-6× the Baseline Conductivity ($R^2$=0.96):
5 mm<gap=x<25 mm, 0.5 mm<radius=y<1.0 mm, 5 mm<exposure=z<30 mm, 1<factor=w<6

Default conductivity of 0.1 S/m and 1000 V which can be scaled for dynamic conductivities. The function is a linear combination of all iterations examined in the parametric study:

Current(w,x,y,z)=a+bx+cy+dz+ew+f(x+bb)(y+cc)+g(x+bb)(z+dd)+h(x+bb)(w+ee)+i(y+cc)(z+dd)+j(y+cc)(w+ee)+k(z+dd)(w+ee)+l(x+bb)(y+cc)+m(y+cc)(z+dd)(w+ee)+n(x+bb)(z+dd)(w+ee)+o(x+bb)(y+cc)(w+ee)+p(x+bb)(y+cc)(z+dd)(w+ee)

FIGS. 9A-9E show the representative (15 mm gap) correlation between current vs. exposure length and electrode radius for maximum conductivities (1×-6×, respectively).

FIGS. 10A and 10B are tables showing experimental validation of the code for determining the tissue/potato dynamic conductivity from in vitro measurements.

Determining the Relationship Between Blunt Tip Electrode Configuration and e-Field Distribution after IRE Treatment Model Assumptions:
Gompertz Conductivity: Pulse duration=50 μs, Ex-vivo kidney tissue
Baseline Conductivity: σ=0.1 S/m
Spherical Domain: diameter=10 cm
Electrode Radius: r=0.5 mm
Parametric Study:
Total Combinations: 1440 models
Maximum Conductivity: 1.0×, 1.25×, 1.5×, 2×, 3×, 4×, 5×, 6× the baseline
Edge-to-edge Distance: 5, 10, 15, 20, 25 mm
Electrode Exposure: 5, 10, 15, 20, 25, 30 mm
Voltage-to-distance Ratio: 500, 1000, 1500, 2000, 2500, 3000 V/cm Example 3

Comparison of analytical solutions with statistical (numerical) model to calculate current and explanation of procedure that results in 3D IRE volume.

Figure 11A:
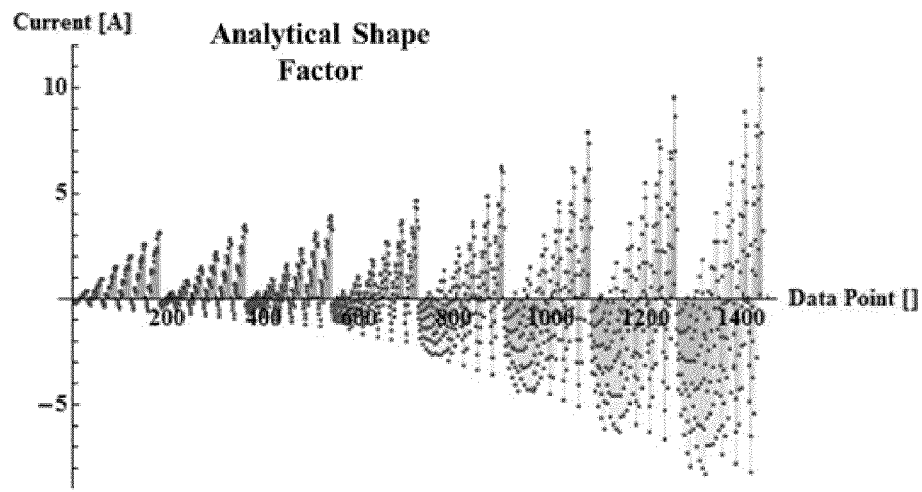
FIGS. 11A and 11B are graphs plotting residual current versus data point for analytical shape factor (FIG. 11A) and statistical (numerical) non-linear conductivity (FIG. 11B).
Figure 11B:
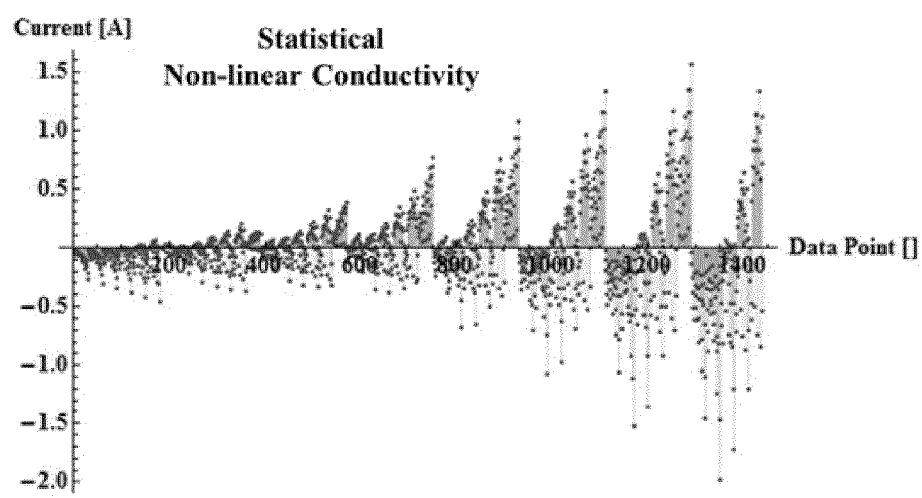

The process of backing-out the electrical conductivity using the analytical solutions and the one proposed in the "Towards a Predictive Model of Electroporation-Based Therapies using Pre-Pulse Electrical Measurements" abstract presented in the IEEE Engineering in Medicine and Biology Conference in Aug. 28, 2012 in San Diego, Calif. were compared. A method to determine the predictive power of the equations to calculate current is analyzing the residuals of the 1440 combinations of parameters examined. In the context of this specification, a residual is the difference between the predicted current and the actual current. As can be seen in FIGS. 11A and 11B with increasing non-linear change in conductivity due to electroporation and increasing applied electric field there is an increase in the residual for both cases. The main message though is that using the shape factor (analytical) method the maximum residual is 11.3502 A and with the statistical (numerical) model the maximum is 1.55583 A. This analysis suggests that the shape factor method may be inadequate to predict the non-linear changes in current that occur during electroporation and for reliable predictions the statistical (numerical) method may be better.

Figures 12A, 12B:
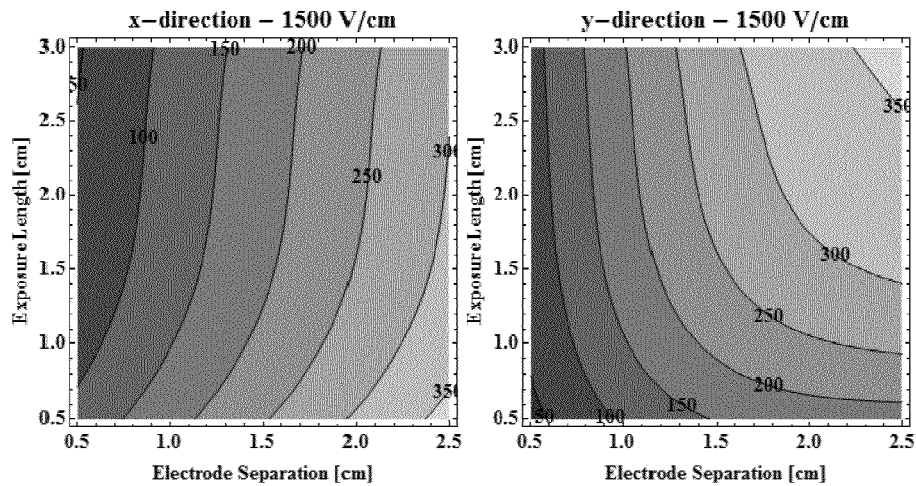
Figure 12C:
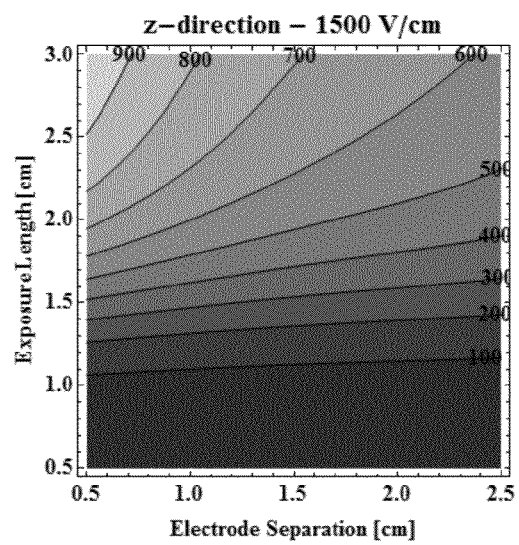

In terms of the prediction of the volume treated a representative method is to map out the electric field 5 cm in the directions along the (x,0,0), (0,y,0), and (0,0,z) axes from the origin. In addition, the electric field can be extracted along a line that starts at the origin and ends at 3 cm along each of the axes. These plots contain the information for determining the distances at which a particular IRE threshold occurs. In embodiments, 1440 different parameter combinations were simulated that resulted in data sets of 28,692 (x-direction), 20,538 (y-direction), 27,306 (z-direction), and 25,116 (xyz-direction) for homogeneous conductivity. Even though these simulations only include dynamic conductivity changes due to electroporation, it is believed that an identical analysis for simulations that also include the changes in conductivity due to temperature could also be performed. In this manner, it would be possible to determine irreversible electroporation thresholds as a function of temperature and electroporation. Manipulating these large data sets is challenging but it provides all the necessary information to study the effect of electrode separation, electrode length, dynamic conductivity factor, and voltage-to-distance ratio for any position along the described paths. In order to be able to manipulate the data and extract the distance for different IRE thresholds, the function NonlinearModelFit (Mathematica) was used in order to come up with analytical expressions that would closely match the electric field. A different function was used for each of the directions studied in the positive directions along the Cartesian coordinate system. The Micheilis Menten function was used along the x-direction ($R^2$=0.978978), the analytical solution to the Laplace equation along the y-direction ($R^2$=0.993262), and the Logistic equation in the z-direction ($R^2$=0.983204). Each of those functions was scaled by a 3rd order polynomial function that enabled the fit to incorporate the electrode separation and electrode exposure as well. Even though the described functions were used to fit the data from the numerical data, there might be other functions that are also appropriate and this will be explored further in order to use the most reliable fit. In FIGS. 12A-12C provided are representative contour plots of the electric field strength at 1.0 cm from the origin using an edge-to-edge voltage-to-distance ratio of 1500 V/cm assuming a z=1 which is the case for non-electroporated electrical conductivity. It is important to note that in this case the y and z data are starting from (0, 0, 0) and the x-data starts outside the external electrode-tissue boundary. One representative case is presented, but any of the 1440 parameters combinations that were disclosed in the conference proceeding could be plotted as well.

The following functions describe the electric field [V/cm] distributions along the x-axis ($E_x$), y-axis ($E_y$), and z-axis ($E_z$) as a function of voltage-to-distance (W), edge-to-edge separation between the electrodes (X), exposure length (Y), maximum conductivity to baseline conductivity (Z), and distance in the x-direction (xx), y-direction (yy), and z-direction (zz).

Micheilis Menten Equation (Electric Field in the x-Direction)

$$E_x(W,X,Y,Z,xx)=W*(a*\text{Exp}[-b \cdot xx]+c)*(dX^3+eX^2+fX+gY^3+hY^2+iY+j)+k$$

The coefficients for the NonlinearModelFit are given below:
a=−0.447392, b=8.98279, c=−0.0156167, d=−0.0654974, e=0.468234, f=−6.17716, g=0.326307, h=−2.33953, i=5.90586, j=−4.83018, k=9.44083

Laplace Equation (Electric Field in the y-Direction)

$$E_y(W, X, Y, Z, yy) = a + (X^3 + X^2 + bX + cY^3 + dY^2 + eY + f) * \left( h + \frac{(gWXZ)}{2} * \left( \frac{1}{\text{Log}\left[\frac{X+0.1}{0.05}\right]} \right) * \text{Abs}\left[ \frac{1}{i-yy-\frac{X}{2}-0.05} - \frac{1}{i \cdot yy + \frac{X}{2}+0.05} \right] \right)$$

The coefficients for the NonlinearModelFit are given below:
a=−56.6597, b=−42.9322, c=6.66389, d=−50.8391, e=141.263, f=138.934, g=0.00417123, h=0.184109

Logistic Equation (Electric Field in the z-Direction)

$$E_z(W, X, Y, Z, zz) = a + \frac{bWZ}{1+c \cdot \text{Exp}\left[d \cdot \left(\frac{2zz}{y}-e\right)\right]} \cdot (fX^3 + gX^2 + hX + i) \cdot (jY^3 + kY^2 + lY + m)$$

The coefficients for the NonlinearModelFit are given below:
a=49.0995, b=−0.00309563, c=1.39341, d=4.02546, e=1.24714, f=0.276404, g=−1.84076, h=4.93473, i=−9.13219, j=0.699588, k=−5.0242, l=12.8624, m=19.9113.

In order to visualize the predicted IRE shape the equation of an ellipsoid was used and the semi-axes were forced to intersect with the locations at which the IRE threshold wants to be examined. Therefore, the provided functions can be adjusted in real-time to display the IRE volume for any electric field threshold. This is important since different tissues have different IRE thresholds that depend on the temperature, dielectric properties of the tissue, the electrode configuration, and the pulse parameters used. Once again, even though the equation for an ellipsoid is used to represent the IRE volume, other functions may be evaluated that may also be appropriate to replicate the morphology of the zones of ablation being achieved experimentally such as the Cassini curve. A 1500 V/cm was used as the voltage-to-distance ratio, electrode exposure 2 cm, and electrode separation 1.5 cm to generate 3 different IRE zones using 1000 V/cm, 750 V/cm, and 500 V/cm as the IRE thresholds with z=1.

From the 3D plots representing the zones of ablation shown in FIGS. 13A-13C it can be seen that if the IRE threshold is reduced from 1000 V/cm to either 750 V/cm or 500 V/cm, the volume becomes larger. This is representative of how different tissues may have different thresholds and this code may provide the ability to simulate the fields in a broad/generic manner that can then be applied to any tissue. Incorporating the xyz-data that was extracted from the parametric study will help modify the "roundness" of the current depictions of the zone of IRE ablation in order to more realistically replicate the experimental results. However, to the best of the inventors' knowledge there is no such adaptable code currently available to provide a 3D IRE volume as a function of measured current, electrode length, electrode exposure, applied voltage-to-distance ratio, and customizable electric field threshold so it is believed that this will greatly help the medical community in planning and verifying the clinical treatments of patients being treated with the IRE technology.

Example 4

Specific Conductivity

Specific conductivity can be important in embodiments for treatment planning of irreversible electroporation (IRE). For many applications, especially when treating tumors in the brain, the volume (area) of IRE should be predicted to maximize the ablation of the tumorous tissue while minimizing the damage to surrounding healthy tissue. The specific electrical conductivity of tissue during an irreversible electroporation (IRE) procedure allows the physicians to: determine the current threshold; minimize the electric current dose; decrease the Joule heating; and reduce damage to surrounding healthy tissue. To measure the specific conductivity of tissue prior to an IRE procedure the physician typically performs one or more of the following: establishes the electrode geometry (shape factor); determines the physical dimensions of the tissue; applies a small excitation AC voltage signal (1 to 10 mV); measures the AC current response; calculates the specific conductivity ($\sigma$) using results from the prior steps. This procedure tends to not generate tissue damage (low amplitude AC signals) and will supply the physician (software) with the required information to optimize IRE treatment planning, especially in sensitive organs like the brain which is susceptible to high electrical currents and temperatures. Thus, the IRE procedure is well monitored and can also serve as a feedback system in between series of pulses and even after the treatment to evaluate the area of ablation.

Special Cases for Electrode Geometry
Nomenclature (Units in Brackets):
$V_e$=voltage on the hot electrode (the highest voltage), [V]
G=electroporation voltage gradient (required for electroporation), [V/m]
$R_1$=radius of electrode with highest voltage (inner radius), [m]
$R_2$=radius at which the outer electrodes are arranged (outer radius), [m]
i=total current, [A]
L=length of cylindrical electrode, [m]
A=area of plate electrode, [$m^2$]
$\sigma$=electrical conductivity of tissue, [S/m]
$\rho$=density
c=heat capacity Case 1

Electrical conduction between a two-cylinder (needle) arrangement of length L in an infinite medium (tissue). It is important to note that this formulation is most accurate when $L \gg R_1, R_2$ and $L \gg w$. The electrical conductivity can be calculated from, $$\sigma = \frac{i \cdot S}{V_e}$$

where the shape factor (S) corresponding to the electrode dimensions and configuration is given by, $$\frac{2 \cdot \pi \cdot L}{\cosh^{-1}\left(\frac{4 \cdot w^2 - (2 \cdot R_1)^2 - (2 \cdot R_2)^2}{8 \cdot R_1 \cdot R_2}\right)}$$

Case 2

Cylindrical arrangement in which the central electrode is a cylinder (needle) with radius $R_1$ and the outer electrodes are arranged in a cylindrical shell with a shell radius of $R_2$ (not the radius of the electrodes). The voltage on the central electrode is $V_e$. The voltage distribution in the tissue may be determined as a function of radius, r:

$$V = V_e \frac{\ln\frac{r}{R_2}}{\ln\frac{R_1}{R_2}}$$

The required voltage on the central electrode to achieve IRE:

$$V_e = GR_2 \ln\frac{R_2}{R_1}$$

The required current on the central electrode:

$$i = \frac{2\pi L \sigma V_e}{\ln\frac{R_2}{R_1}}$$

The specific conductivity ($\sigma$) of the tissue can be calculated since the voltage signal ($V_e$) and the current responses (i) are known.

Explanation of Electrical Concepts.

By using the bipolar electrode described previously in US Patent Application Publication No. 2010/0030211 A1, one can apply a small excitation AC voltage signal (for example from about 1 to 10 mV), $$V(t) = V_0 \sin(\omega t)$$

where V(t) is the potential at time t, $V_0$ is the amplitude of the excitation signal and $\omega$ is the frequency in radians/s. The reason for using a small excitation signal is to get a response that is pseudo-linear since in this manner the value for the impedance can be determined indicating the ability of a system (tissue) to resist the flow of electrical current. The measured AC current (response) that is generated by the excitation signal is described by $$I(t) = I_0 \sin(\omega t + \theta)$$

where I(t) is the response signal, $I_0$ is the amplitude of the response ($I_0 \neq V_0$) and $\theta$ is the phase shift of the signal. The impedance (Z) of the system (tissue) is described by, $$Z = (V(t))/(I(t)) = (V_0 \sin(\omega t))/(I_0 \sin(\omega t + \theta)) = Z_0 (\sin(\omega t))/(\sin(\omega t + \theta))$$

It is important to note that the measurement of the response is at the same excitation frequency as the AC voltage signal to prevent interfering signals that could compromise the results. The magnitude of the impedance $|Z_0|$ is the electrical resistance of the tissue. The electrical resistivity ($\Omega$m) can be determined from the resistance and the physical dimensions of the tissue in addition to the electrode geometry (shape factor). The reciprocal of the electrical resistivity is the electrical conductivity (S/m). Therefore, after deriving the electrical resistivity from the methods described above, the conductivity may be determined.

As described in U.S. Patent Application No. 61/694,144 the analytical solution (Table 4) assumes that the length of the electrodes is much larger than the electrode radius or separation distance between the electrodes. Additionally, the analytical solution is not capable of capturing the non-linear electrical response of the tissue during electroporation procedures. The proposed statistical algorithm (Table 3) is preferably used in order to capture the response in treatments that are being conducted clinically and show how the analytical overestimates the baseline and maximum current that uses the experimental data.

TABLE 3

Determination of conductivity using the statistical model and in vivo data from pre-pulse and IRE pulses in canine kidney tissue using identical electrode configuration that the experimental one described below.

| | Current [A] | Voltage [V] | Volt-2-Dist [V/cm] | Conductivity [S/m] | Z = $\sigma_{max}/\sigma_{min}$ |
|---|---|---|---|---|---|
| Pre-Pulse | 0.258 | 48 | 53 | 0.365 | — |
| IRE-Pulse | 20.6 | 1758 | 1953 | 1.037 | 2.841 |
| IRE-Pulse | 23.7 | 1758 | 1953 | 1.212 | 3.320 |
| IRE-Pulse | 23.6 | 1758 | 1953 | 1.207 | 3.305 |
| Avg. IRE | 22.6 | 1758 | 1953 | 1.150 | 3.150 |
| IRE-Pulse | 10.4 | 1259 | 1399 | 0.727 | 1.990 |
| IRE-Pulse | 11.1 | 1257 | 1397 | 0.789 | 2.162 |
| IRE-Pulse | 11 | 1257 | 1397 | 0.781 | 2.138 |
| Avg. IRE | 10.8 | 1257 | 1397 | 0.763 | 2.090 |
| Pre-Pulse | 0.343 | 73.3 | 52 | 0.341 | — |
| IRE-Pulse | 23.6 | 2262 | 1616 | 1.007 | 2.952 |
| IRE-Pulse | 24.3 | 2262 | 1616 | 1.041 | 3.051 |
| IRE-Pulse | 25.4 | 2262 | 1616 | 1.094 | 3.207 |
| Avg. IRE | 24.5 | 2262 | 1616 | 1.050 | 3.080 |

TABLE 4

Determination of conductivity using the analytical model and in vivo data from pre-pulse and IRE pulses in canine kidney tissue using identical electrode configuration than the experimental one described below. Assumption: Length >> radius, Length >> width, 2 cylindrical electrodes in an infinite medium.

| | Current [A] | Voltage [V] | Volt-2-Dist [V/cm] | Shape Factor [m] | Conductivity [S/m] |
|---|---|---|---|---|---|
| Pre-Pulse | 0.258 | 48 | 53 | 0.01050 | 0.512 |
| IRE-Pulse | 20.6 | 1758 | 1953 | 0.01050 | 1.116 |
| IRE-Pulse | 23.7 | 1758 | 1953 | 0.01050 | 1.284 |
| IRE-Pulse | 23.6 | 1758 | 1953 | 0.01050 | 1.279 |

TABLE 4-continued

Determination of conductivity using the analytical model and in vivo data from pre-pulse and IRE pulses in canine kidney tissue using identical electrode configuration than the experimental one described below. Assumption: Length >> radius, Length >> width, 2 cylindrical electrodes in an infinite medium.

|  | Current [A] | Voltage [V] | Volt-2-Dist [V/cm] | Shape Factor [m] | Conductivity [S/m] |
|---|---|---|---|---|---|
| Avg. IRE | 22.6 | 1758 | 1953 | 0.01050 | 1.225 |
| IRE-Pulse | 10.4 | 1259 | 1399 | 0.01050 | 0.787 |
| IRE-Pulse | 11.1 | 1257 | 1397 | 0.01050 | 0.841 |
| IRE-Pulse | 11 | 1257 | 1397 | 0.01050 | 0.834 |
| Avg. IRE | 10.8 | 1257 | 1397 | 0.01050 | 0.819 |
| Pre-Pulse | 0.343 | 73.3 | 52 | 0.00924 | 0.506 |
| IRE-Pulse | 23.6 | 2262 | 1616 | 0.00924 | 1.129 |
| IRE-Pulse | 24.3 | 2262 | 1616 | 0.00924 | 1.163 |
| IRE-Pulse | 25.4 | 2262 | 1616 | 0.00924 | 1.215 |
| Avg. IRE | 24.5 | 2262 | 1616 | 0.00924 | 1.172 |

Example 5

In Vivo Experiments

1) Animals

IRE ablations were performed in canine kidneys in a procedure approved by the local animal ethics committee. Male canines weighing approximately 30 kg were premedicated with acetylpromazine (0.1 mg/kg), atropine (0.05 mg/kg), and morphine (0.2 mg/kg) prior to general anesthesia induced with propofol (6 mg/kg, then 0.5 mg/kg/min) and maintained with inhaled isofluorane (1-2%). Anesthetic depth was monitored by bispectral index monitoring (Covidien, Dublin, Ireland) of EEG brain activity. After ensuring adequate anesthesia, a midline incision was made and mesenchymal tissue was maneuvered to access the kidney. Pancuronium was delivered intravenously to mitigate electrically mediated muscle contraction, with an initial dose of 0.2 mg/kg, and adjusted if contractions increased.

2) Experimental Procedure

Two modified 18 gauge needle electrodes (1.0 mm diameter and 1.0 cm in exposure) were inserted as pairs into the superior, middle, or inferior lobe of the kidney, with lobes being randomly selected. A BTX ECM830 pulse generator (Harvard Apparatus, Cambridge, Mass.) was used to deliver an initial 100 µs pre-pulse of 50 V/cm voltage-to-distance ratio (center-to-center) between the electrodes to get an initial current able to be used to determine baseline conductivity. Electrical current was measured with a Tektronix TCP305 electromagnetic induction current probe connected to a TCPA300 amplifier (both Tektronix, Beaverton, Oreg.). A Protek DS0-2090 USB computer-interface oscilloscope provided current measurements on a laptop using the included DSO-2090 software (both GS Instruments, Incheon, Korea). A schematic of the experimental setup can be found in FIG. 14A. Following the pre-pulse, a series of 100 pulses, each 100 µs long, at a rate of 1 pulse per second was delivered, reversing polarity after 50 pulses. A five second pause was encountered after pulses 10 and 50 to save data. A schematic diagram showing dimension labeling conventions is shown in FIG. 14B. Representative current waveforms from a pre-pulse and experimental pulse can be found in FIGS. 14C and 14D, respectively. Electrode exposure lengths were set to 1 cm for all trials. The separation distance between electrodes and applied voltage may be found in Table 5. After completing pulse delivery, the electrodes were removed. Two additional ablations were performed in the remaining lobes before repeating the procedure on the contralateral kidney, resulting in a total of three ablations per kidney and six per canine.

TABLE 5

KIDNEY EXPERIMENT PROTOCOLS IN CANINE SUBJECTS

| Setup | Separation, cm | Voltage, V | Voltage-Distance Ratio, V/cm | n |
|---|---|---|---|---|
| 1 | 1 | 1250 | 1250 | 4 |
| 2 | 1 | 1750 | 1750 | 4 |
| 3 | 1.5 | 2250 | 1500 | 6 |

3) Kidney Segmentation and 3D Reconstruction

Numerical models provide an advantageous platform for predicting electroporation treatment effects by simulating electric field, electrical conductivity, and temperature distributions. By understanding the electric field distribution, one can apply an effective lethal electric field threshold for IRE, $E_{IRE}$, to predict ablation lesion dimensions under varying pulse protocols (electrode arrangements and applied voltages). However, in order to do so, these models should first be calibrated with experimental data. Here, the numerical simulation algorithm developed from porcine kidneys was expanded that accounts for conductivity changes using an asymmetrical sigmoid function (R. E. Neal, 2nd, et al., "Experimental characterization and numerical modeling of tissue electrical conductivity during pulsed electric fields for irreversible electroporation treatment planning," IEEE Trans Biomed Eng., vol. 59, pp. 1076-85. Epub 2012 Jan. 6, 2012 ("R. E. Neal, $2^{nd}$, et al., 2012")). The model is calibrated to the experimental lesions to determine an effective electric field threshold under the three experimental setups used. In addition, static and linear conductivity functions are also correlated to the lesion dimensions. The three functions are used to evaluate which numerical technique will result in better accuracy in matching lesion shapes and resulting current from actual IRE ablations in mammalian tissue, particularly for kidney.

The imaging-based computational model domains were constructed from a magnetic resonance imaging (MRI) scan of a kidney from a canine subject of similar size to those in the study. The scans were scaled by 1.21 times in all directions to better match the experimental kidney dimensions while maintaining the anatomical characteristics. Mimics 14.1 image analysis software (Materialise, Leuven, BG) was used to segment the kidney geometry from the surrounding tissues. The kidney was traced in each of the two-dimensional (2D) MRI axial slices, which were then integrated into a three-dimensional (3D) solid representation of the kidney volume which was refined and exported to 3-matic version 6.1 (Materialise, Leuven, BG) to generate a volumetric mesh compatible with Comsol Multiphysics finite element modeling software (Comsol Multiphysics, v.4.2a, Stockholm, Sweden).

Electrodes were simulated as paired cylinders, each 1 cm long and 1 mm in diameter, and separated by 1 or 1.5 cm to represent the two experimental conditions. The pairs were inserted into the 3D kidney mesh in two configurations, representing both experimental approaches that used either the superior/inferior (vertical) or middle (horizontal) lobe of the kidney, both with tips 1.5 cm deep. The finite element model simulated the electric field distribution in the kidney, which was used to determine cell death EIRE by correlating the electric field values with the average in vivo lesion height and width dimensions.

4) Electric Field Distribution and Lethal $E_{IRE}$ Determination

The electric field distribution is determined according to $$-\nabla \cdot (\sigma(|E|)\nabla \phi) = 0 \quad (1)$$

where $\sigma$ is the electrical conductivity of the tissue, E is the electric field in V/cm, and $\phi$ is the electrical potential. Tissue-electrode boundaries for the cathode and anode were defined as $\phi = V_o$ and ground, respectively. The remaining boundaries were treated as electrically insulating, $d\phi/dn=0$, since the kidneys were isolated from the surrounding mesenchymal tissue during the experimental procedures. The current density was integrated over a mid-plane parallel to both electrodes to determine simulated electric current.

The model was solved for the vertical and horizontal electrode configurations, each considering three electrical conductivity tissue responses. These responses included a homogeneous static conductivity ($\sigma_0$) as well as two that accounted for electroporation based conductivity changes in tissue that result from cell membrane permeabilization. The dynamic models are based on a relationship between a minimum baseline and a maximum conductivity. The static conductivity model was used to determine the baseline conductivity, $\sigma_0$, by matching simulated electrical current with the pre-pulse experimental data, where the field strength should be below that able to permeabilize any cells in the tissue. The maximum conductivity, $\sigma_{max}$, occurs when the number of cells electroporated in the tissue has saturated, and the cellular membranes no longer restrict the extent of interstitial electrolyte mobility. The statistical model discussed in (P. A. Garcia, et al., "Towards a predictive model of electroporation-based therapies using pre-pulse electrical measurements," Conf Proc IEEE Eng Med Biol Soc, vol. 2012, pp. 2575-8, 2012 ("P. A. Garcia, et al., 2012")) was used to predict $\sigma_{max}$ from previously characterized tissue response to pre-pulse cm and electrical data.

The $\sigma_0$ and $\sigma_{max}$ values provide the required parameters to define the electric field-dependent conductivity, $\sigma(|E|)$, of renal tissue in vivo. One model assumed a linear relationship that grew between the minimum and maximum conductivities over a range from 200 to 2000 V/cm, $\sigma_L(|E|)$, and the second used an asymmetrical sigmoid Gompertz curve, $\sigma_S(|E|)$, derived from the work described in (R. E. Neal, 2nd, et al., 2012) using the equation:

$$\sigma_S(|E|) = \sigma_0 + (\sigma_{max} - \sigma_0) \cdot \exp[-A \cdot \exp(-B \cdot E)] \quad (2)$$

where A and B are unitless coefficients that vary with pulse length, t(s). This function was fit using curve parameters for a 100 μs long pulse, where A=3.053 and B=0.00233 (R. E. Neal, $2^{nd}$, et al., 2012)

The electric field distribution along a width and height projection based at the midpoint length of the electrodes was used to determine the electric field magnitude that matched experimental lesion dimensions. This was performed for all three conductivity scenarios in all three experimental protocol setups in order to determine which model best matched the IRE ablations, providing the optimum conductivity modeling technique for mammalian tissue.

5) Results

In Vivo Experiments

Electrical Currents.

All animals survived the procedures without adverse event until euthanasia. Electrical pre-pulse currents were 0.258±0.036 A (mean±SD) for the 1 cm electrode separation trials and 0.343±0.050 A for the 1.5 cm separation trials. Electrical currents from the trials for pulses 1-10, 40-50, and 90-100 are reported in Table 6. Although currents are typically reported to increase with consecutive pulses, there is no statistically significant correlation between pulse number and measured current. Therefore, all numerical calibrations to match electrical current and determine $\sigma_{max}$ used the average current from all captured pulses for each experimental setup.

TABLE 6

EXPERIMENTAL ELECTRIC CURRENTS TO CALIBRATE NUMERICAL MODELS

| Setup | Separation, cm | Average Delivered Voltage, V | Pulse Number | Average Electric Current, A* |
|---|---|---|---|---|
| Pre 1 | 1 | 48 | 1750 | 0.258 (0.036) |
| Pre 2 | 1.5 | 73 | 1250 | 0.343 (0.050) |
| 1 | 1 | 1258 | 1-10 | 10.4 (1.7) |
|  |  |  | 40-50 | 11.1 (1.1) |
|  |  |  | 90-100 | 11.0 (1.7) |
| 2 | 2 | 1758 | 1-10 | 20.6 (3.2) |
|  |  |  | 40-50 | 23.7 (5.1) |
|  |  |  | 90-100 | 23.6 (3.8) |
| 3 | 1.5 | 2262 | 1-10 | 23.6 (1.47) |
|  |  |  | 40-50 | 24.3 (3.25) |
|  |  |  | 90-100 | 25.4 (3.27) |

*Currents given as "average (standard deviation)"

6) Determination of Dynamic Conductivity Function

Pre-pulse electrical current was used to calculate the baseline conductivity, $\sigma_0$, used in the static numerical simulation. In addition, the baseline and maximum, a $\sigma_{max}$, electrical conductivities required for generating the asymmetrical sigmoid and linear dynamic conductivity functions were calculated according to the procedure outlined in (P. A. Garcia, et al., 2012) and are provided in Table 7. The ratio between these conductivities was calculated and demonstrates an increase in conductivity between 2.09 and 3.15 times, consistent with values determined in the literature for other organs (N. Payselj, et al., "The course of tissue permeabilization studied on a mathematical model of a subcutaneous tumor in small animals," IEEE Trans Biomed Eng, vol. 52, pp. 1373-81, August 2005).

TABLE 7

BASELINE AND MAXIMUM ELECTRIC CONDUCTIVITIES

| Setup | Gap, cm | V/d Ratio, V/cm | $\sigma_0$ | $\sigma_{max}$ | $\sigma_{max}/\sigma_0$ |
|---|---|---|---|---|---|
| 1 | 1 | 1250 | 0.365 | 0.763 | 2.09 |
| 2 | 1 | 1750 | 0.365 | 1.150 | 3.15 |
| 3 | 1.5 | 1500 | 0.341 | 1.050 | 3.08 |

Example 6

How to Use the Ratio of Maximum Conductivity to Baseline Conductivity in Modifying the Electric Field Distribution and Thus the Cassini Oval Equation Irreversible electroporation (IRE) is a promising new method for the focal ablation of undesirable tissue and tumors. The minimally invasive procedure involves placing electrodes into the region of interest and delivering a series of low energy electric pulses to induce irrecoverable structural changes in cell membranes, thus achieving tissue death. To achieve IRE, the electric field in the region of interest needs to be above a critical threshold, which is dependent on a variety of conditions such as the physical properties of the tissue, electrode geometry and pulse parameters. Additionally, the electric conductivity of the tissue changes as a result of the pulses, redistributing the electric field and thus the treatment area. The effect of a dynamic conductivity around the electrodes where the highest electric fields are generated was investigated in order to better predict the IRE treatment for clinical use.

The electric field distribution associated with the electric pulse is given by solving the governing Laplace equation, $\nabla \cdot (\sigma \nabla \phi) = 0$, where $\sigma$ is the tissue electrical conductivity (baseline 0.2 S/m) and $\phi$ the electrical potential (3000 V). The dynamic changes in electrical conductivity due to electroporation were modeled with the flc2hs Heaviside function within the finite element modeling software used in the study (Comsol Multiphysics 3.5a, Stockholm, Sweden). The dynamic conductivity factor ranged between 2.0-7.0 times the baseline value in the regions exceeding 3000 V/cm. The total electrical current, volumes, and lesion shapes from the IRE treatment were evaluated.

Figures 15A, 15B:
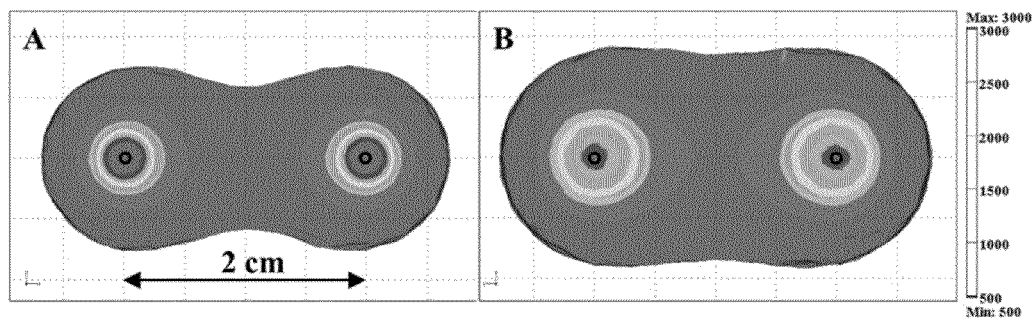
FIGS. 15A and 15B are electric field [V/cm] isocontours for non-electroporated tissue (FIG. 15A) and electroporated tissue (FIG. 15B) maps assuming a maximum conductivity to baseline conductivity ratio of 7.0×.

FIGS. 15A and 15B display the electric field distributions for the non-electroporated (baseline conductivity) and electroporated (maximum/baseline conductivity) maps, respectively. The electric field from using the baseline conductivity resulted in a "peanut" shape distribution (FIG. 15A). By incorporating the conductivity ratio between a $\sigma_{max}/\sigma_0$, there is a redistribution of the electric field and thus the volumes, currents and lesion shapes are modified as well. The electric field distribution for a 7.0× factor (FIG. 15B), shows a more gradual dissipation of the electric field and a rounder predicted IRE lesion.

A method to predict IRE lesions and incorporate the dynamic changes in conductivity due to electroporation around the electrodes is presented in this example. This procedure provides additional tools to better approximate the electric field distributions in tissue and thus help to generate more reliable IRE treatment planning for clinical use using Finite Element Analysis (FEA) models.

Specifically in order to adapt the Cassini Oval to match experimental lesions or electric field distributions the following procedure should be used:

In IRE treatments, the electric field distribution is the primary factor for dictating defect formation and the resulting volume of treated tissue (J. F. Edd and R. V. Davalos, "Mathematical modeling of irreversible electroporation for treatment planning," Technol Cancer Res Treat, vol. 6, pp. 275-286, 2007; D. Sel, et al., "Sequential finite element model of tissue electropermeabilization," IEEE Trans Biomed Eng, vol. 52, pp. 816-27, May 2005; S. Mahnic-Kalamiza, et al., "Educational application for visualization and analysis of electric field strength in multiple electrode electroporation," BMC Med Educ, vol. 12, p. 102, 2012 ("S. Mahnic-Kalamiza, et al., 2012")). The electric field is influenced by both the geometry and positioning of the electrodes as well as the dielectric tissue properties. Additionally, altered membrane permeability due to electroporation influences the tissue conductivity in a non-linear manner. Therefore numerical techniques are preferably used to account for different electrode configurations and incorporate tissue-specific functions relating the electrical conductivity to the electric field distribution (i.e. extent of electroporation). The inventors are currently using imaging-based computational models for IRE treatment planning that use the physical properties of the tissue and patient-specific 3D anatomical reconstructions to generate electric field distributions (P. A. Garcia, et al., "Non-thermal irreversible electroporation (N-TIRE) and adjuvant fractionated radiotherapeutic multimodal therapy for intracranial malignant glioma in a canine patient," Technol Cancer Res Treat, vol. 10, pp. 73-83, 2011 ("P. A. Garcia, et al, 2011")).

Oftentimes in clinical practice, there is need to rapidly visualize the estimated zone of ablation without relying in complex and time consuming numerical simulations. As an alternative, analytical solutions are powerful techniques that provide valuable insight and offer the ability to rapidly visualize electric field distributions (S. Mahnic-Kalamiza, et al., 2012). However, these analytical solutions assume infinitely long electrodes which are not the case in clinical practice and do not incorporate the non-linear changes in tissue conductivity due to electroporation. Therefore, there is a need for simple, quick, and accurate methods to provide physicians with predicted IRE zones of ablation during surgery when one of the pulse parameters needs to be adjusted. To this end, the inventors have adapted the Cassini curve in an effort to provide researchers and physicians with a graphical representation of IRE zones of ablation, for example, in in vivo porcine liver. The goal of this work is to provide a correlation between experimentally produced zones of ablations in in vivo porcine liver tissue with the corresponding IRE pulse parameters and electrode configuration. These Cassini curves are calibrated to experimental IRE ablations, and incorporate the dynamic changes in tissue conductivity, a limitation of the analytical approach.

Figures 16A, 16B:
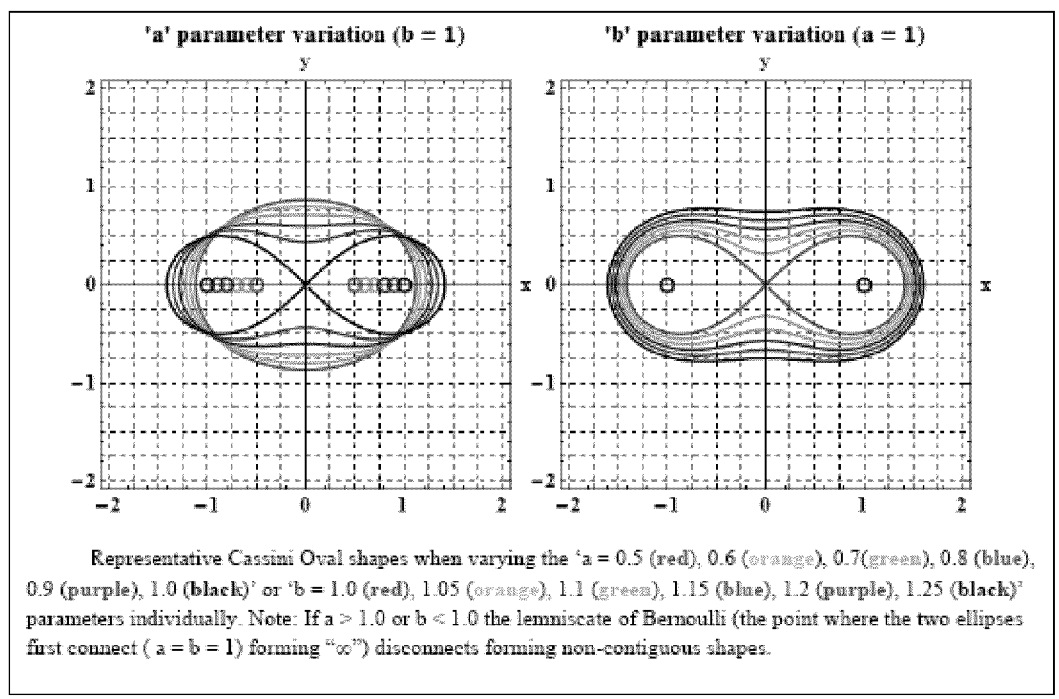
FIGS. 16A and 16B are representative Cassini Oval shapes when varying the 'a=0.5 (red), 0.6 (orange), 0.7 (green), 0.8 (blue), 0.9 (purple), 1.0 (black)' or 'b=1.0 (red), 1.05 (orange), 1.1 (green), 1.15 (blue), 1.2 (purple), 1.25 (black)' parameters individually. Note: If a>1.0 or b<1.0 the lemniscate of Bernoulli (the point where the two ellipses first connect (a=b=1) forming "∞") disconnects forming non-contiguous shapes.

The Cassini oval is a plane curve that derives its set of values based on the distance of any given point, a, from the fixed location of two foci, $q_1$ and $q_2$, located at $(x_1, y_1)$ and $(x_2, y_2)$. The equation is similar to that of an ellipse, except that it is based on the product of distances from the foci, rather than the sum. This makes the equation for such an oval $$[(x_1-a)^2+(y_1-a)^2] \cdot [(x_2-a)^2+(y_2-a)^2]=b^4 \qquad (3)$$

where $b^4$ is a scaling factor to determine the value at any given point. For incorporation of this equation into shapes that mimic the electric field distribution, it is assumed that the two foci were equidistantly located on the x-axis at $(\pm x, 0)$. The flexibility of the Cassini curve is crucial since it allows for fitting a wide range of shapes by adjusting the 'a' and/or 'b' parameters from Equation 3 simultaneously and fitting them to the experimental lesion dimensions or the locations at which a particular electric field value results from the computational simulations. The new approach in this analysis is that it is not assumed that the parameter 'a' is related to the separation distance between the electrodes used in IRE treatments for example but will be a second parameter to match the width/depth of any distribution thus allowing for more flexibility between the shapes achieved with the Cassini Oval as can be seen in FIGS. 16A and 16B.

The in vivo experimental data in porcine liver was provided from published studies performed at the Applied Radiology Laboratory of Hadassah Hebrew University Medical Center (P. A. Garcia, et al., 2011). All experiments were performed with Institutional Animal Care and Use Committee approval from the Hebrew University Medical Center. The treatments were performed with a two-needle electrode configuration, 1.5 cm center-to-center separation, 2.0 cm electrode exposure, and an applied voltage of 2250 V. In this paper we only evaluate the effect of pulse number and pulse duration on the resulting 'a' and 'b' parameters required to fit the IRE zones of ablation with the Cassini curve. The NonlinearModelFit function in Wolfram Mathematica 9 was used to determine the 'a' and 'b' parameters (average±standard deviation) for each pulse parameter resulting in three curves for each condition. This same technique can be used to fit the 'a' and 'b' parameters to match the electric field shape at any particular electric field value as well thus providing an avenue to capture the shape for any IRE lesion independent of the tissue or patient.

Figure 17:
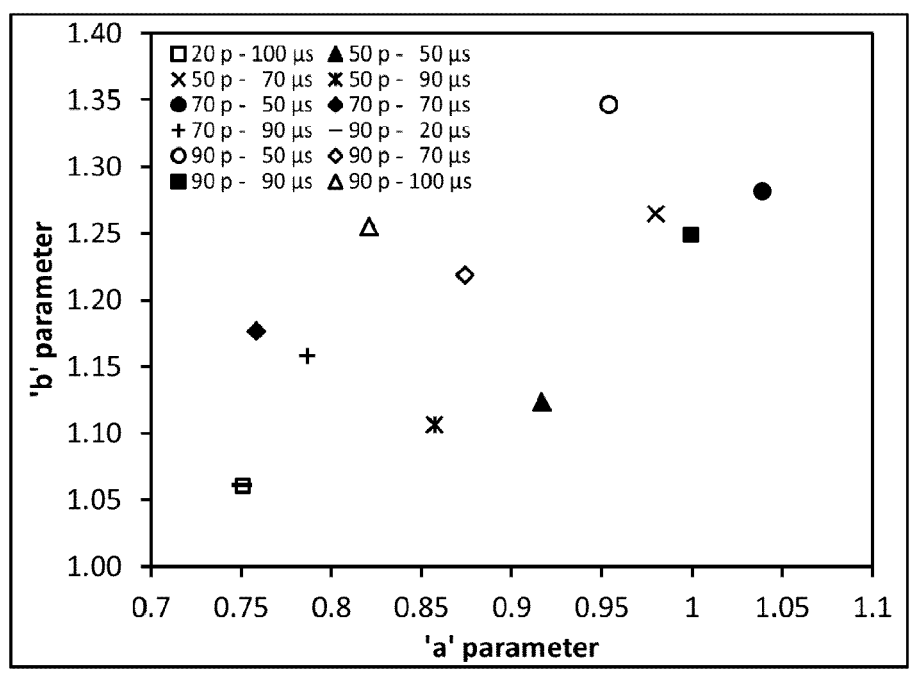
FIG. 17 is a graph showing NonlinearModelFit results for the 'a' and 'b' parameters used to generate the Cassini curves that represent the experimental IRE zones of ablation in porcine liver.

The NonlinearModelFit results for the 'a' and 'b' parameters to generate the Cassini curves are provided in FIG. 17. The 'a' parameter ranged from 0.75-1.04 and the 'b' from 1.06-1.35 for the average IRE zones of ablation in the in vivo porcine liver. From these data it can be seen that each pulse parameter used results in a unique 'a' and 'b' combination except for the twenty 100-μs pulses and ninety 20-μs pulses which overlap since they had identical IRE ablations. Therefore, consideration should be given to pulse length and total number of pulses when planning treatments to ensure maximum accuracy when using Cassini curves to rapidly predict treatment zones.

Figure 18:
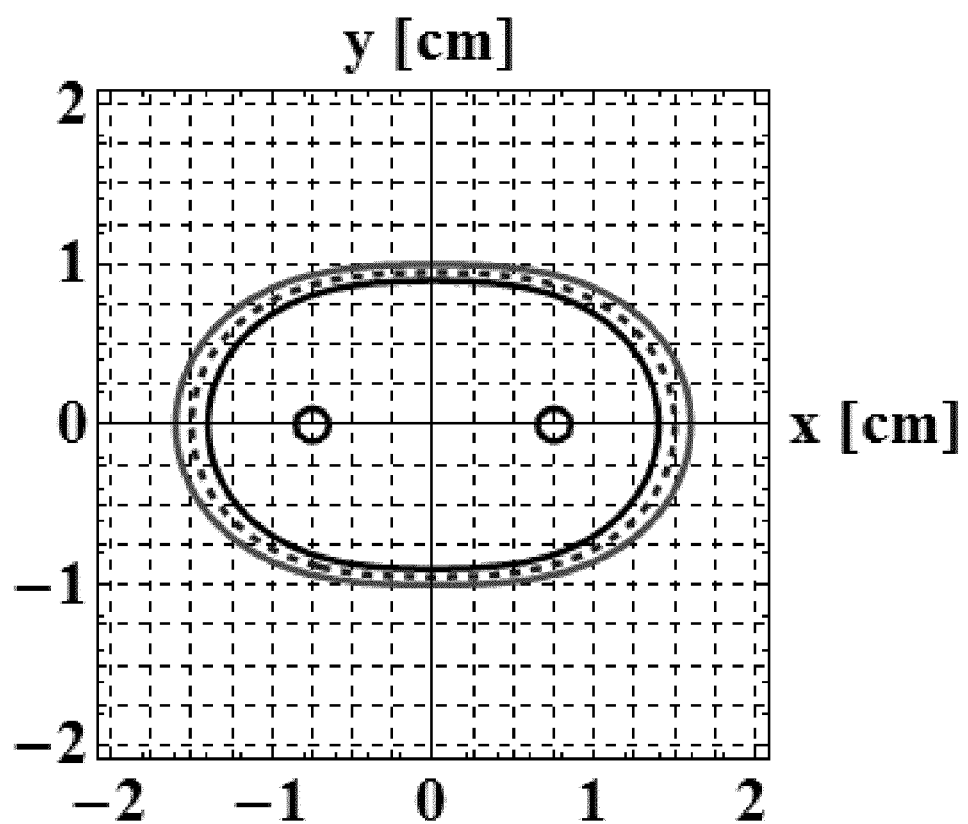
FIG. 18 shows Cassini curves from a ninety 100-μs pulse IRE treatment that represent the average zone of ablation (blue dashed), +SD (red solid), and –SD (black solid) according to a=0.821±0.062 and b=1.256±0.079.

FIG. 18 provides a representation of the average IRE zone of ablation and also includes the experimentally achieved standard deviations. This Cassini curve is the most clinically relevant as ninety 100-μs pulses is the recommended setting by the manufacturer that is currently being used by physicians to treat several types of cancer. The Cassini curves in FIG. 18 were generated with a=0.821±0.062 and b=1.256±0.079 that corresponded to IRE ablations that were 3.0±0.2 cm in width and 1.9±0.1 cm in depth (P. A. Garcia, et al., 2011). The results suggest that the Cassini curve is a viable method to represent experimentally achieved IRE zones of ablation. These curves can be used to provide physicians with simple, quick, and accurate prediction of IRE treatments. The parameters generated in this study were achieved from porcine liver ablations data. Therefore, future work needs to determine the parameters for other tissues and/or tumors. Cassini curve parameters should be re-calibrated if the pulse parameters or electrode configuration (i.e. separation or exposure) deviate from the typical protocols in Ben-David et al. Additionally, there is a need to calibrate these Cassini curves to electric and temperature distributions in order to take advantage of the relatively simple curves in representing simulated solutions that account for other pulse parameters and electrode configuration including different electrode separations, diameter, exposure, and voltages. A method to represent IRE zones of ablation in a computationally efficient manner and based on experimental data is thus presented. Such methods can be used to predict IRE ablation in liver in order to provide physicians with an immediate tool for treatment planning.

Figure 19:
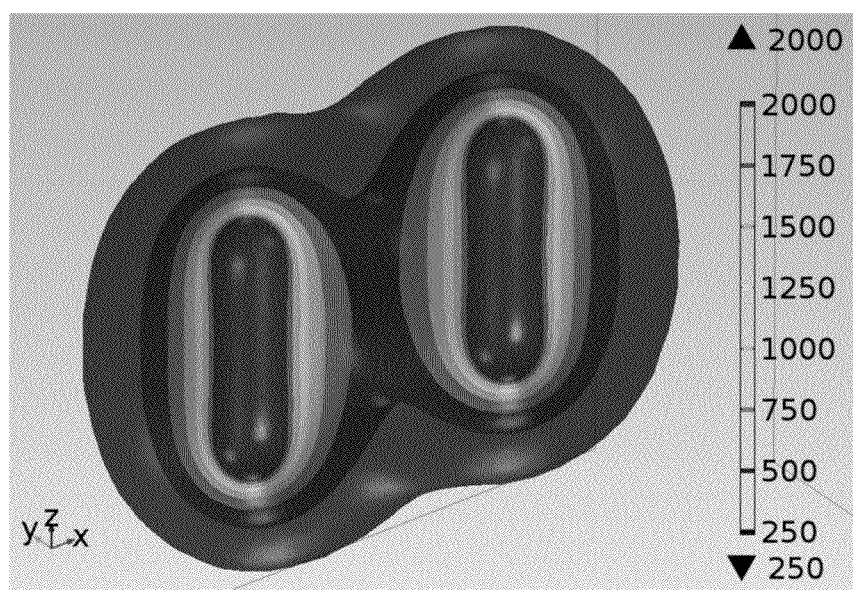
FIG. 19 is a representation of the Finite Element Analysis (FEA) model for a 3D Electric Field [V/cm] Distribution in Non-Electroporated (Baseline) Tissue with 1.5-cm Electrodes at a Separation of 2.0 cm and with 3000 V applied.

FIG. 19 is a representation of the 3D Electric Field [V/cm] Distribution in Non-Electroporated (Baseline) Tissue with 1.5-cm Electrodes at a Separation of 2.0 cm and 3000 V applied.

Figure 20A:
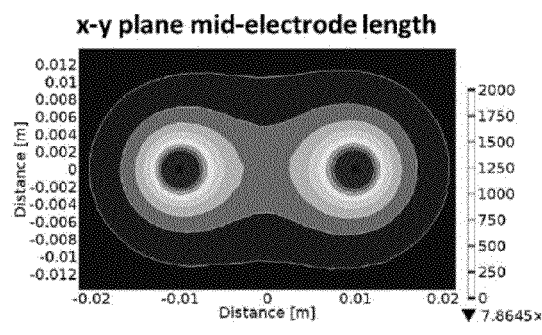
Figure 20B:
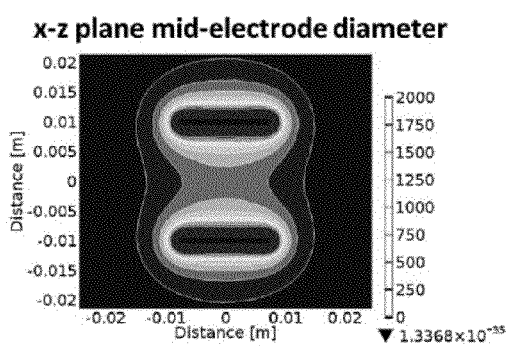
Figure 20C:
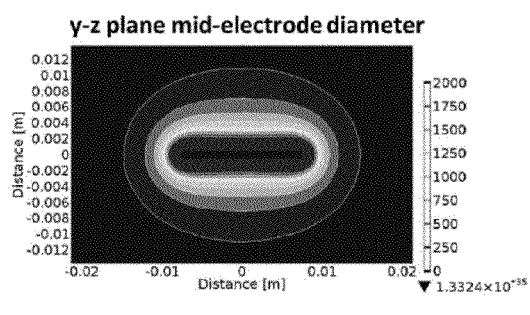
Figure 20D:
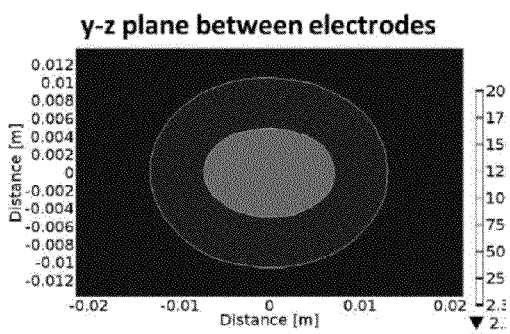

FIGS. 20A-D are representations of the Electric Field [V/cm] Distributions from the 3D Non-Electroporated (Baseline) Models with 1.5-cm Electrodes at a Separation of 2.0 cm and 3000 V (cross-sections), wherein FIG. 20A is a representation of the x-y plane mid-electrode length, FIG. 20B is a representation of the x-z plane mid-electrode diameter, FIG. 20C is a representation of the y-z plane mid electrode diameter, and FIG. 20D is a representation of the y-z plane between electrodes.

Figure 21:
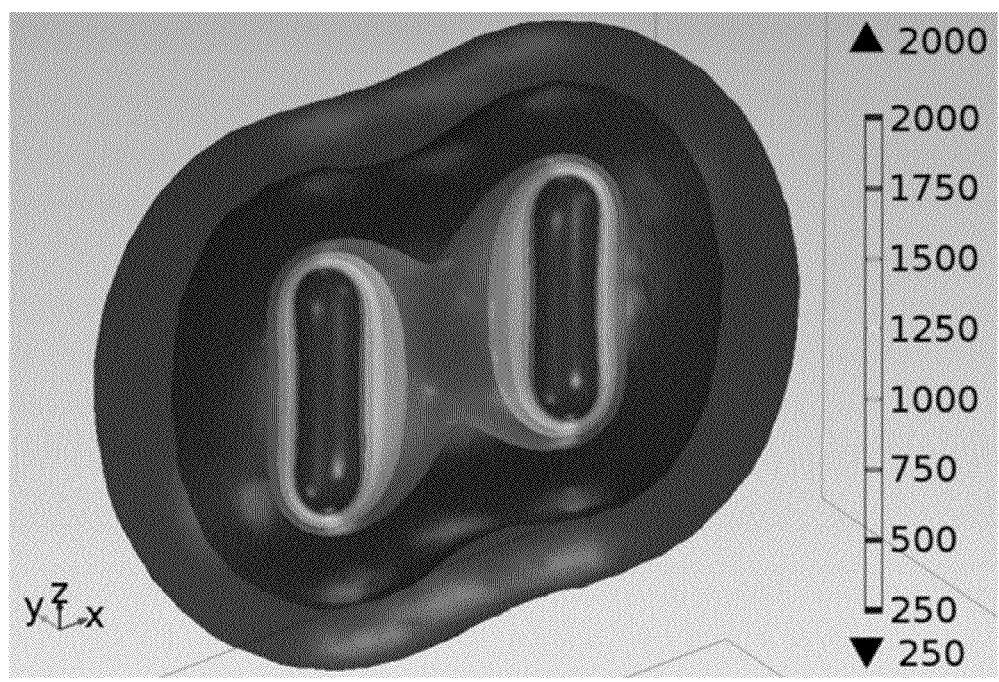
FIG. 21 is a representation of the Finite Element Analysis (FEA) model for a 3D Electric Field [V/cm] Distribution in Electroporated Tissue with 1.5-cm Electrodes at a Separation of 2.0 cm and 3000 V applied assuming $\sigma_{max}/\sigma_0$=3.6.

FIG. 21 is a representation of the 3D Electric Field [V/cm] Distribution in Electroporated Tissue with 1.5-cm Electrodes at a Separation of 2.0 cm and 3000 V applied assuming $\sigma_{max}/\sigma_0=3.6$.

Figure 22A:
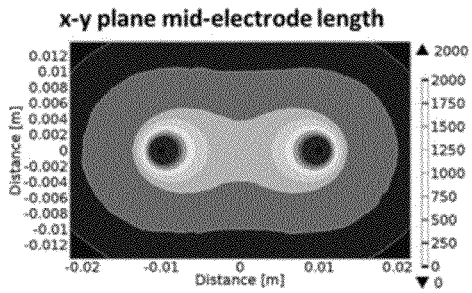
Figure 22B:
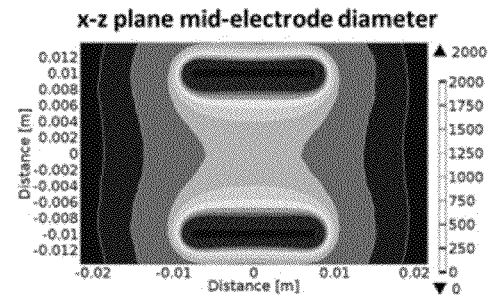
Figure 22C:
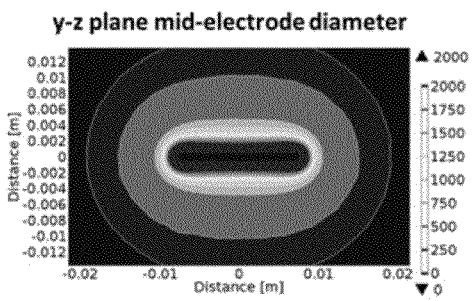
Figure 22D:
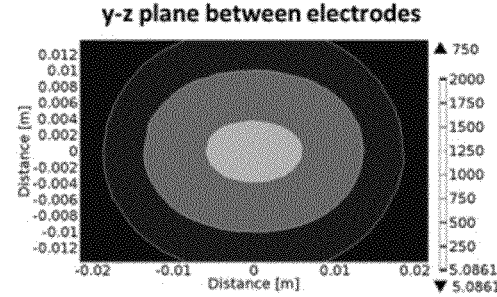

FIGS. 22A-22D are representations of the Electric Field [V/cm] Distributions from the 3D Electroporated Models with 1.5-cm Electrodes at a Separation of 2.0 cm and 3000 V (cross-sections) assuming a $\sigma_{max}/\sigma_0=3.6$, wherein FIG. 22A is a representation of the x-y plane mid-electrode length, FIG. 22B is a representation of the x-z plane mid-electrode diameter, FIG. 22C is a representation of the y-z plane mid electrode diameter, and FIG. 22D is a representation of the y-z plane between electrodes.

Example 7

The Cassini Oval Equation

In mathematics, a Cassini oval is a set (or locus) of points in the plane such that each point p on the oval bears a special relation to two other, fixed points $q_1$ and $q_2$: the product of the distance from p to $q_1$ and the distance from p to $q_2$ is constant. That is, if the function dist(x,y) is defined to be the distance from a point x to a point y, then all points p on a Cassini oval satisfy the equation:

$$\text{dist}(q_1,p) \times \text{dist}(q_2,p) = b^2 \qquad (2)$$

where b is a constant.

Nevertheless, in embodiments the 'b' parameter can be modified to manipulate the shape of the Cassini curve and illustrate the desired electric field distribution. Therefore, the 'b' is a variable parameter that is determined based on the specific location (distance) of a particular electric field threshold to be displayed.

The points $q_1$ and $q_2$ are called the foci of the oval.

Suppose $q_1$ is the point (a,0), and $q_2$ is the point (−a,0). Then the points on the curve satisfy the equation:

$$((x-a)^2+y^2)((x+a)^2+y^2)=b^4 \qquad (3)$$

The Equivalent Polar Equation is:

$$r^4 - 2a^2r^2 \cos 2\theta = b^4 - a^4 \qquad (4)$$

The shape of the oval depends on the ratio b/a. When b/a is greater than 1, the locus is a single, connected loop. When b/a is less than 1, the locus comprises two disconnected loops. When b/a is equal to 1, the locus is a lemniscate of Bernoulli.

The Cassini equation provides a very efficient algorithm for plotting the boundary line of the treatment zone that was created between two probes on grid 200. By taking pairs of probes for each firing sequence, the first probe is set as qi being the point (a,0) and the second probe is set as $q_2$ being the point (−a,0). This original Cassini oval formulation was revised by modifying the assumption of the 'a' parameter being related to the position of the electrodes. In the revised formulation the 'a' is a variable parameter that is adjusted depending on the width and length of the Cassini oval in order to intercept the zone of ablation in the x- and y-directions.

In summary, the 'a' and 'b' variable parameters should be determined in order to have the ability to generate a Cassini curve that could fit the shape of any electric field isocontour. Specifically from the electric field simulations or experimental irreversible electroporation zones of ablation the user should determine the distance along the x-axis and y-axis that the Cassini curve should intersect.

For example in the case of a Finite Element Analysis (FEA) simulation using two 1-mm in diameter electrodes, separated by a center-to-center distance of 2.0 cm, 1.5 cm in exposure, and an applied voltage of 3000 V to one electrode and ground to the other electrode the distances from the point in between the electrodes to a specific electric field contour is given below (Table 8 for the baseline (non-electroporated) and $\sigma_{max}/\sigma_0 = 3.6$ (electroporated) models.

TABLE 8

| E-field [V/cm] | Baseline $(p_{1x}, 0)$ [cm] | Baseline $(0, p_{2y})$ [cm] | $\sigma_{max}/\sigma_0 = 3.6$ $(p_{3x}, 0)$ [cm] | $\sigma_{max}/\sigma_0 = 3.6$ $(0, p_{4y})$ [cm] |
|---|---|---|---|---|
| 300 | 1.97 | 0.92 | 2.38 | 1.39 |
| 400 | 1.81 | 0.69 | 2.17 | 1.18 |
| 500 | 1.70 | 0.49 | 1.99 | 1.01 |

Using the 500 V/cm electric field isocontour as an example it can be determined that the Cassini oval using the baseline model will intersect the points (1.70,0) and (0,0.49) and the model using $\sigma_{max}/\sigma_0=3.6$ will intersect the point (1.99,0) and (0,1.01). Using the two points that will be intersected by the Cassini oval of each specific model type (non-electroporated vs. electroporated) allows for determination of the 'a' and 'b' variable parameter and still satisfy the mathematical condition outlined above in the first paragraph of this section by way of least square fits such as the NonlinearModelFit function in Mathematica or via interpolation tables as the one presented below.

The interpolation method involves assuming values for the 'a' parameter from 0.00 cm to 3.00 cm in steps of 0.01 cm and calculating the 'b' parameter using the specific points from the previous paragraph. The distance and steps were arbitrarily chosen and can vary depending on the specific Cassini oval that is being developed. In the case of Table 9 the point p1x=(1.70 cm, 0 cm) and the point p2y=(0 cm, 0.49 cm) and the corresponding distances to either q1 (−a,0) or q2 (a,0) are calculated.

TABLE 9

| 'a' | d(q1, p1x) = d1 | d(q2, p1x) = d2 | d1*d2 | d(q1, p2y) = d3 | d(q2, p2y) = d4 | d3*d4 | d1*d2/d3*d4 |
|---|---|---|---|---|---|---|---|
| 1.04 | 0.66 | 2.74 | 1.808 | 1.150 | 1.150 | 1.322 | 1.37 |
| 1.05 | 0.65 | 2.75 | 1.788 | 1.159 | 1.159 | 1.343 | 1.33 |
| 1.06 | 0.64 | 2.76 | 1.766 | 1.168 | 1.168 | 1.364 | 1.30 |
| 1.07 | 0.63 | 2.77 | 1.745 | 1.177 | 1.177 | 1.385 | 1.26 |
| 1.08 | 0.62 | 2.78 | 1.724 | 1.186 | 1.186 | 1.407 | 1.23 |
| 1.09 | 0.61 | 2.79 | 1.702 | 1.195 | 1.195 | 1.428 | 1.19 |
| 1.1 | 0.60 | 2.80 | 1.680 | 1.204 | 1.204 | 1.450 | 1.16 |
| 1.11 | 0.59 | 2.81 | 1.658 | 1.213 | 1.213 | 1.472 | 1.13 |
| 1.12 | 0.58 | 2.82 | 1.636 | 1.222 | 1.222 | 1.495 | 1.09 |
| 1.13 | 0.57 | 2.83 | 1.613 | 1.232 | 1.232 | 1.517 | 1.06 |
| 1.14 | 0.56 | 2.84 | 1.590 | 1.241 | 1.241 | 1.540 | 1.03 |
| 1.15 | 0.55 | 2.85 | 1.568 | 1.250 | 1.250 | 1.563 | 1.00 |
| 1.16 | 0.54 | 2.86 | 1.544 | 1.259 | 1.259 | 1.586 | 0.97 |
| 1.17 | 0.53 | 2.87 | 1.521 | 1.268 | 1.268 | 1.609 | 0.95 |
| 1.18 | 0.52 | 2.88 | 1.498 | 1.278 | 1.278 | 1.633 | 0.92 |
| 1.19 | 0.51 | 2.89 | 1.474 | 1.287 | 1.287 | 1.656 | 0.89 |
| 1.2 | 0.50 | 2.90 | 1.450 | 1.296 | 1.296 | 1.680 | 0.86 |
| 1.21 | 0.49 | 2.91 | 1.426 | 1.305 | 1.305 | 1.704 | 0.84 |
| 1.22 | 0.48 | 2.92 | 1.402 | 1.315 | 1.315 | 1.729 | 0.81 |
| 1.23 | 0.47 | 2.93 | 1.377 | 1.324 | 1.324 | 1.753 | 0.79 |
| 1.24 | 0.46 | 2.94 | 1.352 | 1.333 | 1.333 | 1.778 | 0.76 |

In the baseline case analyzed above when the variable parameter 'a' was 1.15 cm the calculated $b^2$ were 1.568 and 1.563 for the d1*d2 and d3*d4, respectively. The last column calculates the ratio of both $b^2$ values in order to determine the location at which they are the same (or closest) which happens when (d1*d2)/(d3*d4)=1.00.

Once it is determined that 'a'=1.15 cm provides the closest ratio to one, the average of the d1*d2 (1.568) and d3*d4 (1.563) quantities is calculated and used to determine the corresponding 'b' parameter by taking the square root as shown in the equation below.

$$b = \sqrt{\frac{(d1*d2) + (d3*d4)}{2}} = \sqrt{\frac{1.568 + 1.563}{2}} = \sqrt{1.5655} = 1.2512 \qquad (5)$$

Once the 'a' and 'b' parameters are determined then any plotting software can be used to illustrate the Cassini curve in Cartesian coordinates using the modified equation $$y = \pm\sqrt{-a^2 - x^2 \pm \sqrt{b^4 + 4a^2 x^2}} \qquad (6)$$

The steps outlined in the previous paragraphs just above can also be used to determine the 'a' and 'b' parameters using the same methodology and with points p3x=(1.99 cm, 0 cm) and p4y=(0 cm, 1.01 cm) and results in 'a'=1.21 cm and 'b'=1.578 cm as the Cassini parameters for the electroporated model when $\sigma_{max}/\sigma_0=3.6$.

TABLE 10

| 'a' | d(q1, p3x) = d5 | d(q2, p3x) = d6 | d5*d6 | d(q1, p4y) = d7 | d(q2, p4y) = d8 | d7*d8 | d5*d6/d7*d8 |
|---|---|---|---|---|---|---|---|
| 1.1  | 0.89 | 3.09 | 2.750 | 1.493 | 1.493 | 2.230 | 1.23 |
| 1.11 | 0.88 | 3.10 | 2.728 | 1.501 | 1.501 | 2.252 | 1.21 |
| 1.12 | 0.87 | 3.11 | 2.706 | 1.508 | 1.508 | 2.275 | 1.19 |
| 1.13 | 0.86 | 3.12 | 2.683 | 1.516 | 1.516 | 2.297 | 1.17 |
| 1.14 | 0.85 | 3.13 | 2.661 | 1.523 | 1.523 | 2.320 | 1.15 |
| 1.15 | 0.84 | 3.14 | 2.638 | 1.531 | 1.531 | 2.343 | 1.13 |
| 1.16 | 0.83 | 3.15 | 2.615 | 1.538 | 1.538 | 2.366 | 1.11 |
| 1.17 | 0.82 | 3.16 | 2.591 | 1.546 | 1.546 | 2.389 | 1.08 |
| 1.18 | 0.81 | 3.17 | 2.568 | 1.553 | 1.553 | 2.413 | 1.06 |
| 1.19 | 0.80 | 3.18 | 2.544 | 1.561 | 1.561 | 2.436 | 1.04 |
| 1.2  | 0.79 | 3.19 | 2.520 | 1.568 | 1.568 | 2.460 | 1.02 |
| 1.21 | 0.78 | 3.20 | 2.496 | 1.576 | 1.576 | 2.484 | 1.00 |
| 1.22 | 0.77 | 3.21 | 2.472 | 1.584 | 1.584 | 2.509 | 0.99 |
| 1.23 | 0.76 | 3.22 | 2.447 | 1.592 | 1.592 | 2.533 | 0.97 |
| 1.24 | 0.75 | 3.23 | 2.423 | 1.599 | 1.599 | 2.558 | 0.95 |
| 1.25 | 0.74 | 3.24 | 2.398 | 1.607 | 1.607 | 2.583 | 0.93 |
| 1.26 | 0.73 | 3.25 | 2.373 | 1.615 | 1.615 | 2.608 | 0.91 |
| 1.27 | 0.72 | 3.26 | 2.347 | 1.623 | 1.623 | 2.633 | 0.89 |
| 1.28 | 0.71 | 3.27 | 2.322 | 1.630 | 1.630 | 2.659 | 0.87 |
| 1.29 | 0.70 | 3.28 | 2.296 | 1.638 | 1.638 | 2.684 | 0.86 |
| 1.3  | 0.69 | 3.29 | 2.270 | 1.646 | 1.646 | 2.710 | 0.84 |

Figure 23:
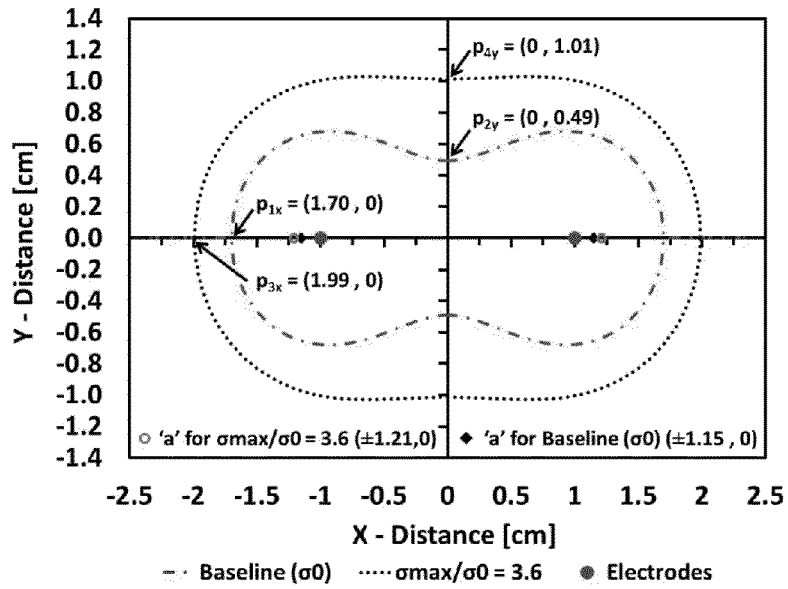
FIG. 23 is a representative Cassini curve representing zones of ablation derived using the pre-pulse procedure to determine the ratio of maximum conductivity to baseline conductivity. For comparison purposes the baseline electric field isocontour is also presented in which no electroporation is taken into account.

In FIG. 23, it can be seen that with the implementation of the pre-pulse concept to determine the ratio of maximum conductivity to baseline conductivity one can derive a Cassini curve representing zones of ablation. In this case the 500 V/cm isocontour was specified but this technique could be used for any other isocontour that perhaps could represent the lethal IRE threshold for any other tissue/tumor type.

The polar equation for the Cassini curve could also be used because since it provides an alternate method for computation. The current Cartesian coordinate algorithm can work equally as well by using the polar equation of the Cassini curve. By solving for $r^2$ from eq. (4) above, the following polar equation was developed:

$$r^2 = a^2 \cos(2*theta) +/- \sqrt{b^4 - a^4 \sin^2(2*theta)} \quad (5)$$

and the 'a' and 'b' parameters should be determined as previously described in this application.

The present invention has been described with reference to particular embodiments having various features. In light of the disclosure provided, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A system for estimating a target ablation zone for a medical treatment device that applies electrical treatment energy through a plurality of electrodes defining a target treatment area, the system comprising:
   a memory;
   a display device;
   a processor coupled to the memory and the display device; and
   a treatment planning module stored in the memory and executable by the processor, the treatment planning module adapted to:
      receive a baseline electrical flow characteristic (EFC) in response to delivery of a test signal to tissue of a subject to be treated;
      determine, based on the baseline EFC, a second EFC representing an expected EFC during delivery of the electrical treatment energy to the target treatment area;
      estimate the target ablation zone for display in the display device based on the second EFC.

2. The system of claim 1, wherein the baseline EFC includes an electrical conductivity.

3. The system of claim 1, wherein:
   the second EFC includes a maximum conductivity expected during the delivery of the electrical treatment energy to the target treatment area;
   the treatment planning module estimates the target ablation zone based on the ratio of the second EFC to the baseline EFC.

4. The system of claim 1, wherein the treatment planning module determines the second EFC based on W, X and Y, in which:
   W=voltage to distance ratio;
   X=edge to edge distance between electrodes;
   Y=exposure length of electrode.

5. The system of claim 1, wherein the treatment planning module estimates the target ablation zone based on a set of predetermined ablation zones according to different W, X, and Y values.

6. The system of claim 5, wherein the treatment planning module estimates the target ablation zone by curve fitting:
- a mathematical function of x values of the ablation volume as a function of W, X, and Y;
- a mathematical function of y values of the ablation volume as a function of W, X, and Y; and
- a mathematical function of z values of the ablation volume as a function of W, X, and Y.

7. The system of claim 1, wherein the treatment planning module is adapted to measure actual maximum tissue conductivity based on either:
- (i) delivery of IRE pulses during the delivery of the electrical treatment energy; or
- (ii) delivery of non-electroporating pulses after the delivery of the electrical treatment energy.

8. The system of claim 7, wherein the treatment planning module is adapted to provide for outcome confirmation of treatment of the subject.

9. A method for estimating a target ablation zone for a medical treatment device that applies electrical treatment energy through a plurality of electrodes defining a target treatment area, the method comprising:
- determining a baseline electrical flow characteristic (EFC) in response to delivery of a test signal to tissue of a subject to be treated;
- determining, based on the baseline EFC, a second EFC representing an expected EFC during delivery of the electrical treatment energy to the target treatment area;
- estimating the target ablation zone for display in the display device based on the second EFC.

10. The method of claim 9, wherein the step of determining a baseline EFC includes determining an electrical conductivity.

11. The method of claim 9, wherein:
- the step of determining a second EFC includes determining an expected maximum electrical conductivity during delivery of the electrical treatment energy to the target treatment area;
- the step of estimating includes estimating the target ablation zone based on the ratio of the second EFC to the baseline EFC.

12. The method of claim 9, wherein the step of determining the second EFC is based on W, X and Y, in which:
- W=voltage to distance ratio;
- X=edge to edge distance between electrodes;
- Y=exposure length of electrode.

13. The method of claim 9 comprising estimating the target ablation zone based on a set of predetermined ablation zones according to different W, X and Y values.

14. The method of claim 13 comprising estimating the target ablation zone by curve fitting:
- a mathematical function of x values of the ablation volume as a function of W, X and Y;
- a mathematical function of y values of the ablation volume as a function of W, X and Y; and
- a mathematical function of z values of the ablation volume as a function of W, X and Y.

15. The method of claim 9 comprising measuring actual maximum tissue conductivity by either:
- (i) delivering IRE pulses during the delivery of the electrical treatment energy; or
- (ii) delivering non-electroporating pulses after the delivery of the electrical treatment energy.

16. The method of claim 15 comprising performing outcome confirmation of treatment of the subject.

* * * * *